United States Patent
Nagasaka et al.

(10) Patent No.: US 9,861,472 B2
(45) Date of Patent: Jan. 9, 2018

(54) INTRAOCULAR LENS INSERTION DEVICE AND INTRAOCULAR LENS INSERTION SYSTEM

(71) Applicant: NIDEK CO., LTD., Aichi (JP)

(72) Inventors: Shinji Nagasaka, Toyota (JP); Akiyoshi Natsume, Okazaki (JP); Takanori Inoue, Toyokawa (JP)

(73) Assignee: NIDEK CO., LTD., Aichi (JP)

( * ) Notice: Subject to any disclaimer, the term of this patent is extended or adjusted under 35 U.S.C. 154(b) by 260 days.

(21) Appl. No.: 14/797,835

(22) Filed: Jul. 13, 2015

(65) Prior Publication Data
US 2016/0015562 A1    Jan. 21, 2016

(30) Foreign Application Priority Data

Jul. 14, 2014 (JP) .................................. 2014-144132

(51) Int. Cl.
 *A61F 2/16* (2006.01)
(52) U.S. Cl.
 CPC ............ *A61F 2/1678* (2013.01); *A61F 2/167* (2013.01); *A61F 2002/1681* (2013.01)
(58) Field of Classification Search
 CPC . A61F 2/167; A61F 2/1678; A61F 2002/1681
 See application file for complete search history.

(56) References Cited

U.S. PATENT DOCUMENTS

| | | | |
|---|---|---|---|
| 2004/0243141 A1 | 12/2004 | Brown | |
| 2009/0234366 A1* | 9/2009 | Tsai | ............ A61F 2/1648 606/107 |
| 2012/0221102 A1 | 8/2012 | Suzuki | |
| 2015/0327992 A1* | 11/2015 | Wagner | ............ A61F 2/1678 606/107 |

FOREIGN PATENT DOCUMENTS

| | | |
|---|---|---|
| JP | 2004351196 A2 | 12/2004 |
| WO | 2011048631 A1 | 4/2011 |
| WO | 2013038688 | 3/2013 |

OTHER PUBLICATIONS

Extended European Search Report dated Nov. 25, 2015 for the corresponding European Patent Application No. 15176516.1.

* cited by examiner

*Primary Examiner* — Ashley Fishback
(74) *Attorney, Agent, or Firm* — Rankin, Hill & Clark LLP

(57) ABSTRACT

An intraocular lens insertion device includes: a plunger that extrudes a deformable intraocular lens into an eye along an extrusion axis, the deformable intraocular lens including an optical part and one or a plurality of support parts extending outward from a periphery of the optical part; an installation part in which the intraocular lens is installed in a state where at least one support part is placed closer to a proximal end side of the extrusion axis than the optical part; and an off-axis movement part that presses the support part of the intraocular lens installed in the installation part from a direction different from the extrusion axis to deform and move the support part.

17 Claims, 22 Drawing Sheets

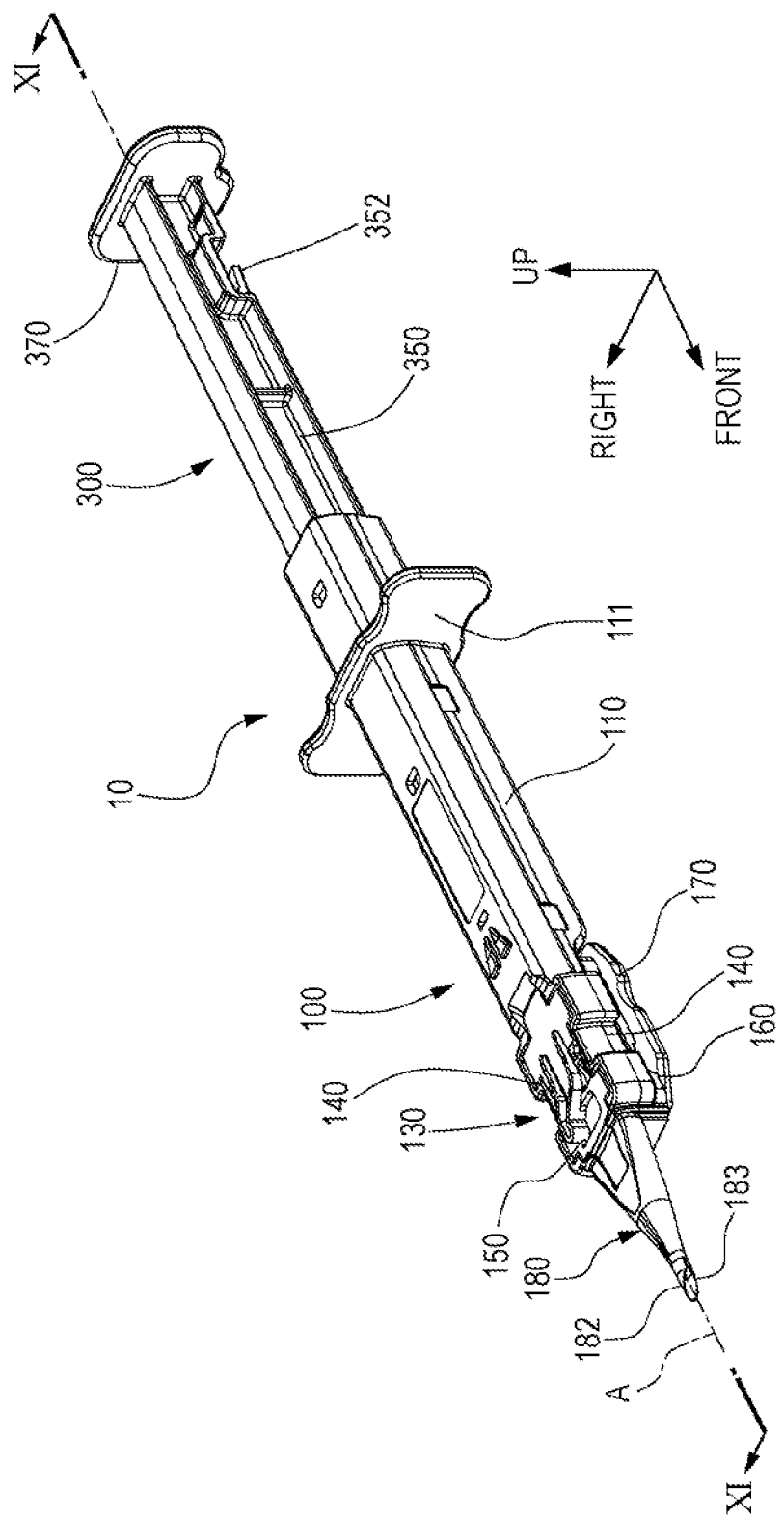

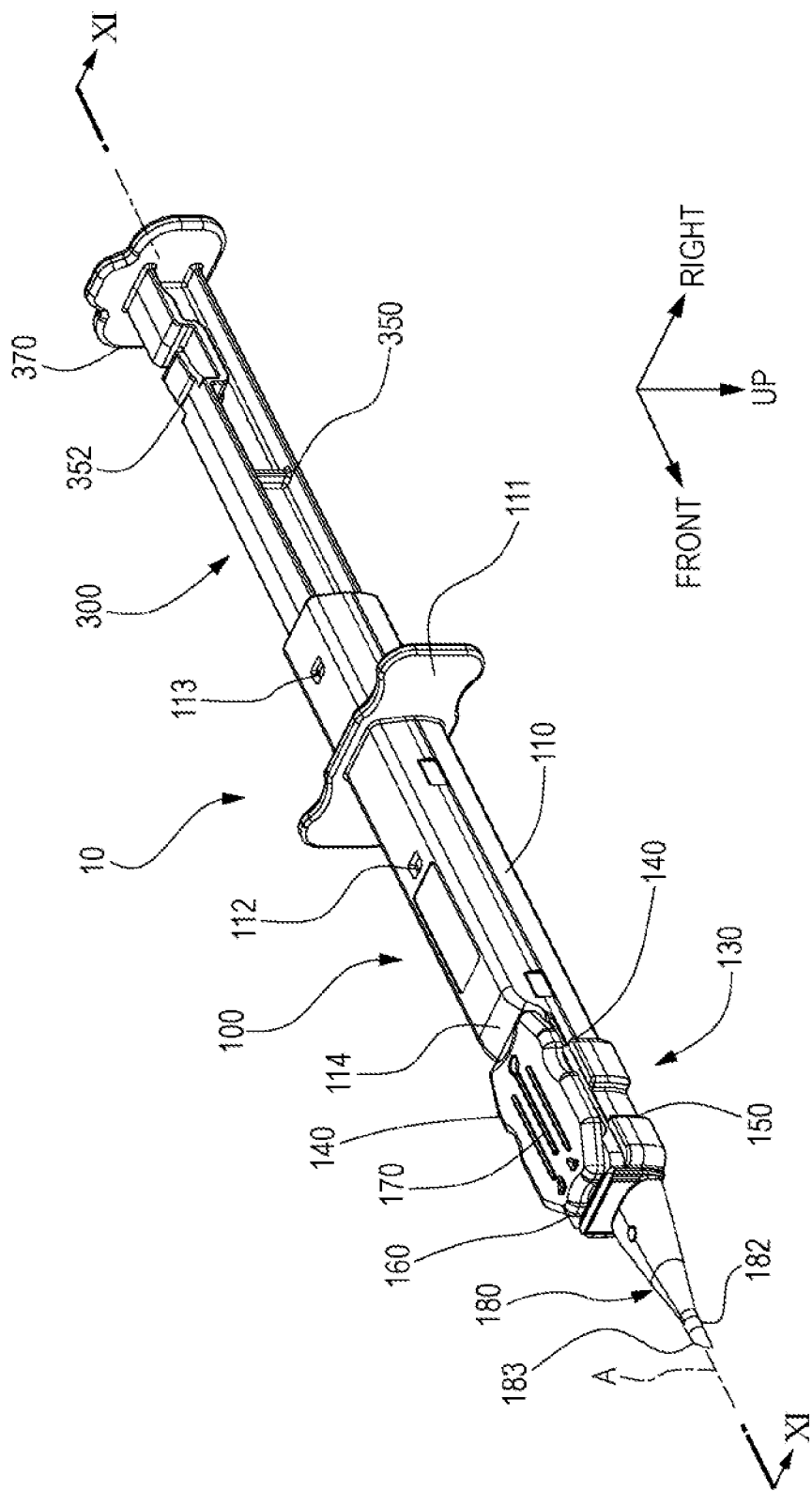

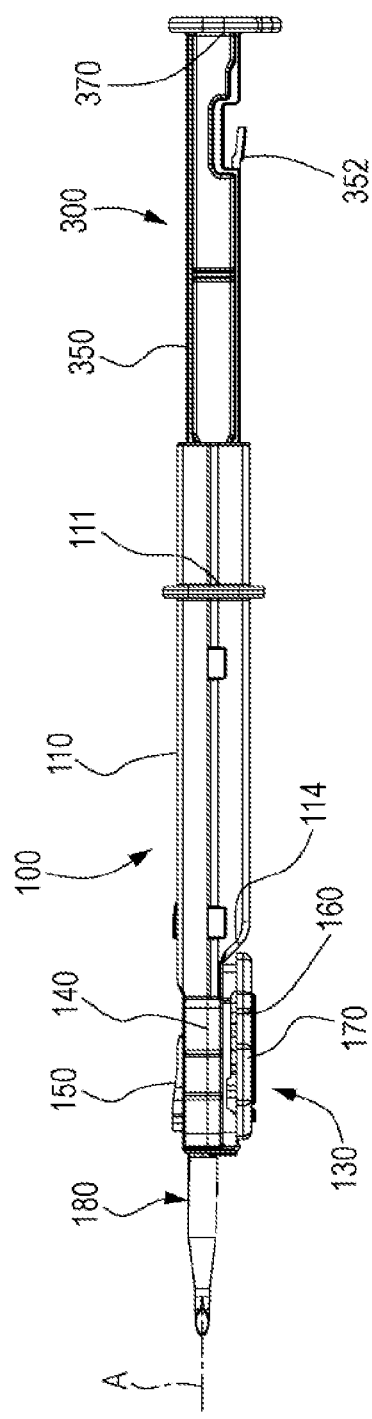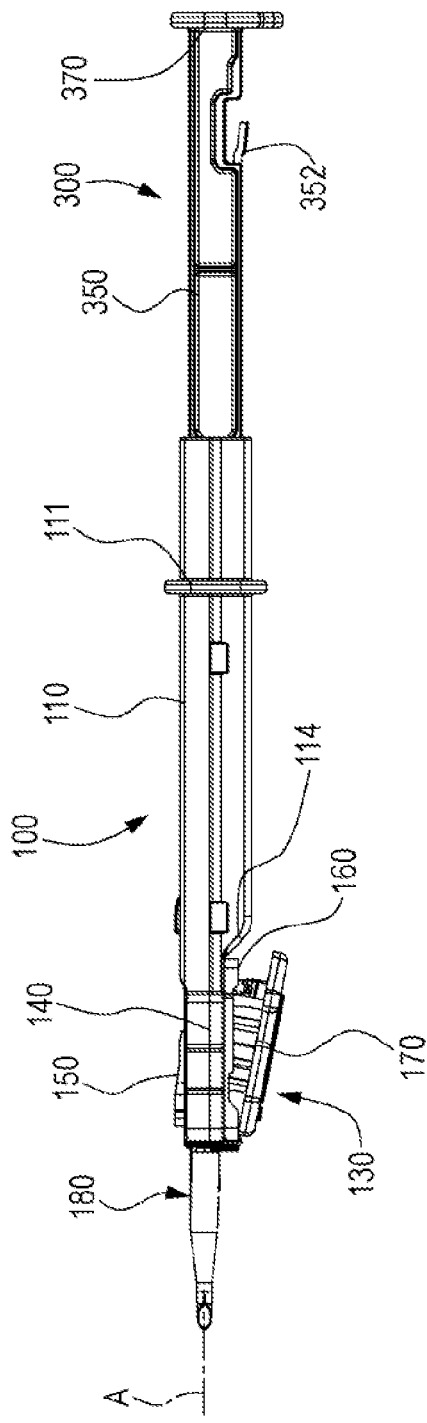

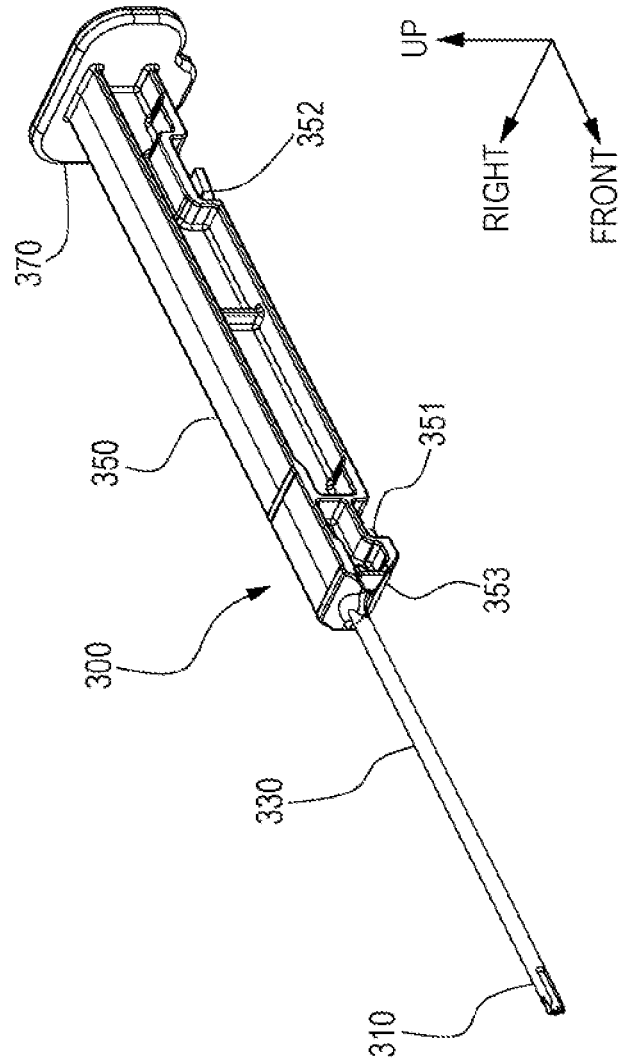

INTRAOCULAR LENS INSERTION DEVICE AND INTRAOCULAR LENS INSERTION SYSTEM

CROSS-REFERENCE TO RELATED APPLICATION

This application claims priority from Japanese Patent Application No. 2014-144132 filed with the Japan Patent Office on Jul. 14, 2014, the entire content of which is hereby incorporated by reference.

BACKGROUND

1. Technical Field

An embodiment of the present disclosure relates to an intraocular lens insertion device and intraocular lens insertion system that insert an intraocular lens into the eye.

2. Description of the Related Art

A method for inserting an intraocular lens instead of the crystalline lens after removing the crystalline lens has been commonly used as one of cataract surgery methods. The intraocular lens is inserted into the eye of a patient through an incision in the eye. In a widely used method, a soft intraocular lens is used to reduce the size of the incision. The intraocular lens is folded small with an intraocular lens insertion device, and inserted into the eye. A widely used soft intraocular lens includes an optical part that provides the diopter scale of the patient's eye and a support part that supports the optical part in the eye.

In a known intraocular lens insertion device for inserting a soft intraocular lens into the eye, the support part of the intraocular lens is bent and part of the support part is placed above an optical surface of the optical part of the intraocular lens. The optical part is then deformed and inserted into the eye (see JP-A-2004-351196). Moreover, in another known intraocular lens insertion device, the support part of the intraocular lens is bent and sandwiched between a proximal end of the optical part of the intraocular lens and a distal end of an extrusion member. The support part is pressed by the extrusion member while being sandwiched between the optical part and the extrusion member, so that the entire intraocular lens is extruded (see WO 2011/048631).

SUMMARY

An intraocular lens insertion device includes: a plunger that extrudes a deformable intraocular lens into an eye along an extrusion axis, the deformable intraocular lens including an optical part and one or a plurality of support parts extending outward from a periphery of the optical part; an installation part in which the intraocular lens is installed in a state where at least one support part is placed closer to a proximal end side of the extrusion axis than the optical part; and an off-axis movement part that presses the support part of the intraocular lens installed in the installation part from a direction different from the extrusion axis to deform and move the support part.

An intraocular lens insertion system includes: deformable means for refracting a light beam including an optical part and one or a plurality of support parts extending outward from a periphery of the optical part means for extruding the deformable means for refracting into an eye along an extrusion axis; means for installing the deformable means for refracting in a state where at least one support part is placed closer to a proximal end side of the extrusion axis than the optical part; and means for pressing the support part of the installed deformable means for refracting from a direction different from the extrusion axis to deform and move the support part.

BRIEF DESCRIPTION OF THE DRAWINGS

FIG. 1 is a perspective view of an intraocular lens insertion device of an embodiment as viewed from obliquely above;

FIG. 2 is a perspective view of the intraocular lens insertion device of FIG. 1 as viewed from obliquely below;

FIGS. 3A and 3B are left side views of the intraocular lens insertion device of FIG. 1, in which FIG. 3A illustrates a state of the intraocular lens insertion device after a setting part is pressed in, and FIG. 3B illustrates a state of the intraocular lens insertion device before the setting part is pressed in;

FIGS. 6A and 6B illustrate the top plate part of the intraocular lens insertion device of FIG. 1, in which FIG. 6A is a perspective view of the top plate part as viewed from obliquely below, and FIG. 6B is a bottom view of the top plate part;

FIGS. 8A and 8B are partial sectional view taken along line XI-XI in FIG. 1, in which FIG. 8A illustrates a state of the intraocular lens insertion device after the setting part is pressed in, and FIG. 8B illustrates a state of the intraocular lens insertion device before the setting part is pressed in;

FIG. 9 is a perspective view of a plunger of the intraocular lens insertion device of FIG. 1 as viewed from obliquely above;

FIGS. 10A to 10E are partial views mainly illustrating a distal end portion of the plunger of FIG. 9, in which FIG. 10A is a front view, FIG. 10B is a plan view, FIG. 10C is a left side view, FIG. 10D is a right side view, and FIG. 10E is a bottom view;

FIGS. 11A and 11B illustrate an intraocular lens used in the embodiment, in which FIG. 11A is a plan view, and FIG. 11B is a left side view;

DESCRIPTION OF THE EMBODIMENTS

Figure 4:
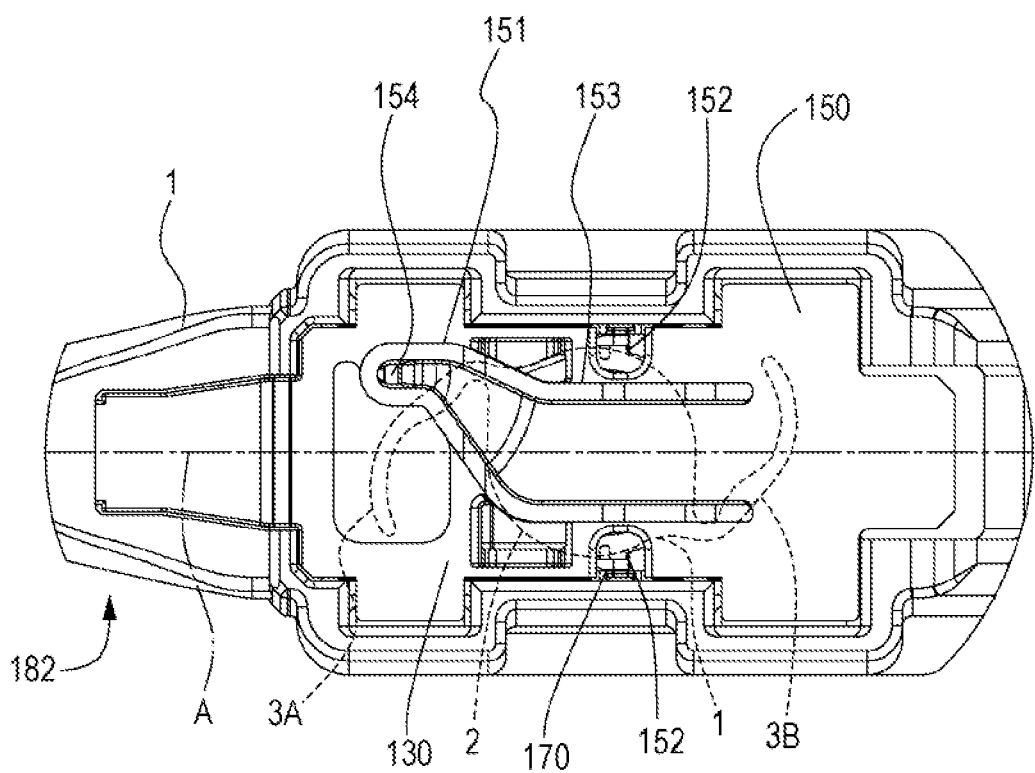
FIG. 4 is a partial view (plan view) of the intraocular lens insertion device of FIG. 1, and mainly illustrates a top plate part.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

If a support part is not suitably bent, a problem may arise in inserting an intraocular lens. For example, the support part may be damaged during the extrusion of the intraocular lens. Moreover, if the support part is not suitably bent, the support part may be restored in an unintended direction in the eye. If the support part is restored in the unintended direction, an operator moves the support part in the eye with tweezers and the like. Hence, the number of processes of surgery increases.

An object of the present disclosure is to provide an intraocular lens insertion device and intraocular lens insertion system that can suitably fold and eject an intraocular lens.

An intraocular lens insertion device and an intraocular lens insertion system according an embodiment of the present disclosure have the following configurations:

(1) An intraocular lens insertion device that advances a rod-like plunger along an extrusion axis to insert, into the eye, a deformable intraocular lens having an optical part and one or a plurality of support parts extending outward from the periphery of the optical part is characterized by an installation part where the intraocular lens is installed in a state where at least one support part is placed closer to a proximal end side than the optical part, and an off-axis movement part that is a member different from the plunger and presses the support part of the intraocular lens installed in the installation part from a direction different from the extrusion axis to deform and move the support part.

(2) An intraocular lens insertion system that advances a rod-like plunger along an extrusion axis to insert, into the eye, a preloaded deformable intraocular lens having an optical part and one or a plurality of support parts extending outward from the periphery of the optical part is characterized by an installation part where the intraocular lens is installed in a state where at least one support part is placed closer to a proximal end side than the optical part, and an off-axis movement part that is a member different from the plunger and presses the support part of the intraocular lens installed in the installation part from a direction different from the extrusion axis to deform and move the support part.

(3) An intraocular lens insertion device that inserts, into the eye, a deformable intraocular lens having an optical part and one or a plurality of support parts extending outward from the periphery of the optical part is characterized by an installation part where the intraocular lens is installed, a movement part that deforms the support part mounted in the installation part to move the support part in a direction approaching the optical part, and a deformation suppression part that suppresses deformation of at least part of the support part deformed by the movement part.

(4) An intraocular lens insertion system that inserts, into the eye, a deformable intraocular lens disposed in advance in the system and having an optical part and one or a plurality of support parts extending outward from the periphery of the optical part is characterized by an installation part where the intraocular lens is installed, a movement part that deforms the support part mounted in the installation part to move the support part in a direction approaching the optical part, and a deformation suppression part that suppresses deformation of at least part of the support part deformed by the movement part.

(5) An intraocular lens insertion device that advances a rod-like plunger along an extrusion axis in a cylindrical main body to insert, into the eye, a deformable intraocular lens having an optical part and one or a plurality of loop-shaped support parts extending outward from the periphery of the optical part is characterized in that the main body has an installation part where the intraocular lens is installed in a state where the support part is oriented in a predetermined direction, and an injection port for injecting a viscoelastic substance into the installation part, and that when the intraocular lens is installed in the installation part, the injection port is located outward of an outer surface of the loop-shaped support part.

(6) An intraocular lens insertion system that advances a rod-like plunger along an extrusion axis in a cylindrical main body to insert, into the eye, a preloaded deformable intraocular lens having an optical part and one or a plurality of loop-shaped support parts extending outward from the periphery of the optical part is characterized in that the main body has an installation part where the intraocular lens is installed in a state where the support part is oriented in a predetermined direction, and an injection port for injecting a viscoelastic substance into the installation part, and that when the intraocular lens is installed in the installation part, the injection port is located outward of an outer surface of the loop-shaped support part.

(7) An intraocular lens insertion device that advances a rod-like plunger along an extrusion axis in a cylindrical main body having a nozzle part at its distal end to insert, into the eye, a deformable intraocular lens having an optical part with optical surfaces that refract light and one or a plurality of support parts extending outward from the periphery of the optical part includes a tapered part provided closer to a proximal end side than the nozzle part and having an inner wall tapered toward the nozzle part, an optical part installation part provided closer to the proximal end side than the tapered part in which the optical part before being extruded by the plunger is installed, and a passage part provided between the tapered part and the optical part installation part in which a passage with a width larger than that of the optical part is formed from the optical part installation part toward the tapered part, and is characterized in that a passage wall, which faces one optical surface of the optical part, of the passage part has a distorted part that is distorted in a concave shape toward a direction away from the extrusion axis as viewed from the direction of the extrusion axis, and that the amount of distortion of the distorted part increases progressively from the proximal end side toward a distal end side.

(8) An intraocular lens insertion system that advances a rod-like plunger along an extrusion axis in a cylindrical main body having a nozzle at its distal end to insert, into the eye, a preloaded deformable intraocular lens having an optical part with optical surfaces that refract light and one or a plurality of support parts extending outward from the periphery of the optical part includes a tapered part provided closer to a proximal end side than the nozzle and having an inner wall tapered toward the nozzle, an optical part installation part provided closer to the proximal end side than the tapered part in which the optical part before being extruded by the plunger is installed, and a passage part provided between the tapered part and the optical part installation part in which a passage with a width larger than that of the optical part is formed from the optical part installation part toward the tapered part, and is characterized in that a passage wall, which faces one optical surface of the optical part, of the passage part has a distorted part that is distorted in a concave shape toward a direction away from the extrusion axis as viewed from the direction of the extrusion axis, and that the amount of distortion of the distorted part increases progressively from the proximal end side toward a distal end side.

(9) An intraocular lens insertion device that advances a rod-like plunger along an extrusion axis to insert, into the eye, a deformable intraocular lens having an optical part and one or a plurality of loop-shaped support parts extending outward from the periphery of the optical part includes an installation part where the intraocular lens to be extruded by the plunder is oriented in a predetermined direction, and a linear movement part that moves linearly in a direction parallel to the extrusion axis to move the support part in a direction approaching the optical part, and is characterized in that an end portion on the distal end side of the linear movement part is placed offset in a direction where a proximal end of the support part of the intraocular lens installed in the installation part is located with respect to the extrusion axis.

(10) An intraocular lens insertion system that advances a rod-like plunger along an extrusion axis to insert, into the eye, a preloaded deformable intraocular lens having an optical part and one or a plurality of loop-shaped support parts extending outward from the periphery of the optical part includes an installation part where the intraocular lens to be extruded by the plunger is oriented in a predetermined direction, and a linear movement part that moves linearly in a direction parallel to the extrusion axis to move the support part in a direction approaching the optical part, and is characterized in that an end portion on a distal end side of the linear movement part is placed offset in a direction where a proximal end of the support part of the intraocular lens installed in the installation part is located as viewed from a distal end side of the extrusion axis.

(11) An intraocular lens insertion device that advances a rod-like plunger along an extrusion axis to insert, into the eye, a deformable intraocular lens having an optical part that refracts light and one or a plurality of loop-shaped support parts extending outward from the periphery of the optical part includes a passage part through which the intraocular lens whose support part has been bent toward the direction of the optical part passes by being pressed by the plunger, and abutment parts, at least provided at right and left positions, which are away from the extrusion axis, of the passage part to abut against different points on a side surface of the optical part passing over the passage, and is characterized in that the abutment parts are formed such that stresses from the right and left directions to give to the intraocular lens are different between the right and left sides of the intraocular lens.

(12) An intraocular lens insertion system that advances a rod-like plunger along an extrusion axis to insert, into the eye, a preloaded deformable intraocular lens having an optical part that refracts light and one or a plurality of loop-shaped support parts extending outward from the periphery of the optical part includes a passage part through which the intraocular lens whose support part has been bent toward the direction of the optical part passes by being pressed by the plunger, and abutment parts, at least provided at right and left positions, which are away from the extrusion axis, of the passage part to abut against different points on a side surface of the optical part passing over the passage, and is characterized in that the abutment parts are formed such that stresses from the right and left directions to give to the intraocular lens are different between the right and left sides of the intraocular lens.

(13) An intraocular lens insertion device that advances a rod-like plunger along an extrusion axis to insert, into the eye, a deformable intraocular lens having an optical part that refracts light and one or a plurality of support parts extending outward from the periphery of the optical part includes an optical part installation part where the optical part is installed, a positioning part that positions at least any of the one or plurality of support parts extending from the optical part at a position displaced from a central plane passing the center in the thickness direction of the optical part installed in the optical part installation part and being perpendicular to an optical axis of the optical part, a movement part that moves the support part positioned by the positioning part in a direction approaching the optical part, and a movement guide part, provided between the positioning part and the optical part installation part, to come into contact with the support part in the middle of the movement of the support part by the movement part and accordingly guide the movement of the support part by the movement part, and is characterized in that the movement guide part guides the movement of the support part while maintaining the distance between the support part and the central plane constant, or guides the movement of the support part in such a manner as that the support part approaches the central plane as the support part approaches the optical part installation part.

(14) An intraocular lens insertion device that advances a rod-like plunger along an extrusion axis to insert, into the eye, a deformable intraocular lens having an optical part and one or a plurality of support parts extending outward from the periphery of the optical part includes an optical part installation part where the optical part is installed, and a positioning part that supports the support part lifting the support part up from an installation surface of the optical part installation part to support the support part at a position higher than the installation surface in a state where the optical part is installed in the optical part installation part, and is characterized by a movement guide part formed extending from the positioning part toward a distal end of the intraocular lens insertion device to maintain by a predetermined distance, or sequentially reduce, the height position of the support part supported lifted up by the positioning part along the extrusion axis.

(15) An intraocular lens insertion system that advances a rod-like plunger along an extrusion axis to insert, into the eye, a preloaded deformable intraocular lens having an optical part that refracts light and one or a plurality of support parts extending outward from the periphery of the optical part includes an optical part installation part where the optical part is installed, a positioning part that positions at least any of the one or plurality of support parts extending from the optical part at a position displaced from a central plane passing the center in the thickness direction of the optical part installed in the optical part installation part and being perpendicular to an optical axis of the optical part, a movement part that moves the support part positioned by the positioning part in a direction approaching the optical part, and a movement guide part, provided between the positioning part and the optical part installation part, to come into contact with the support part in the middle of the movement of the support part by the movement part and accordingly guide the movement of the support part by the movement part, and is characterized in that the movement guide part guides the movement of the support part while maintaining the distance between the support part and the central plane constant, or guides the movement of the support part in such a manner as that the support part approaches the central plane as the support part approaches the optical part installation part.

These intraocular lens insertion devices and intraocular lens insertion systems can easily eject an intraocular lens.

One of typical embodiments in the present disclosure will be described below with reference to the drawings. In the following description, the direction of a nozzle part 182 of a main body 100 (the lower left side on the paper of FIG. 1) is referred to as a distal end direction (front side), and the direction of a pressing part 370 of a plunger (i.e., means for extruding) 300 (the upper right side on the paper of FIG. 1) is referred to as a proximal end direction (rear side). Moreover, the upper side, lower side, obliquely lower right side, and obliquely upper left side on the paper of FIG. 1 are respectively are referred to as the upper, lower, right and left sides of an intraocular lens insertion device 10.

<1-1. Overall Configuration>

The overall configuration of the intraocular lens insertion device 10 of the embodiment will be described with reference to FIGS. 1, 2, 3A, and 3B. The intraocular lens insertion device 10 of the embodiment is used to send a deformable intraocular lens (i.e., deformable means for refracting) 1 into the eye. The intraocular lens insertion device 10 includes the main body 100 and the plunger 300. The main body 100 has a cylindrical shape, and includes a deformation member for folding the intraocular lens 1 (see FIGS. 11A and 11B and the like) small. The plunger 300 is a rod-like shape, and extrudes the intraocular lens 1 into the eye of a patient along an extrusion axis A.

The plunger 300 is attached to the main body 100. The plunger 300 is movable in the front-back direction with respect to the main body 100. The plunger 300 is pressed toward the distal end while being in abutment with the intraocular lens 1 disposed in the main body 100. Accordingly, the intraocular lens 1 is discharged into the patient's eye.

The state of the intraocular lens insertion device 10 of the embodiment can be switched between an insertion state when the intraocular lens 1 is inserted into the eye and a storage state when the intraocular lens insertion device 10 is transferred and stored. In the insertion state, a setting part 170 (described in detail below) is close to the main body 100 (see FIG. 3A). In the storage state, the setting part 170 is away from the main body 100 (see FIG. 3B).

The main body 100 and the plunger 300 of the embodiment are made of a resin material. The intraocular lens insertion device 10 may be formed by molding, cutting by shaving resin, or the like. Since the intraocular lens insertion device 10 is made of the resin material, the intraocular lens insertion device 10 can be easily discarded after use. Moreover, since the intraocular lens insertion device 10 is made of the resin material, the manufacturing cost of the intraocular lens insertion device 10 can be reduced. Thus, the intraocular lens insertion device 10 can be provided to a user at a moderate price.

In the embodiment, a lubricant coating process is performed on an inner wall of the cylindrical main body 100 to extrude the adhesive and soft intraocular lens 1. Moreover, the intraocular lens insertion device 10 of the embodiment is formed to be colorless transparent or colorless translucent. Therefore, the user can easily recognize visually, from the outside of the intraocular lens insertion device 10, the deformed state of the intraocular lens 1 disposed into the intraocular lens insertion device 10.

<1-2. Main Body>

The main body 100 includes a main body cylindrical part 110, an installation part 130, and an insertion part 180. The main body cylindrical part 110 is placed at the proximal end of the main body 100. The main body cylindrical part 110 has a cylindrical shape extending in the distal end direction (front-back direction). The installation part 130 where the intraocular lens 1 is disposed is connected to the distal end of the main body cylindrical part 110. The insertion part 180 is connected to the distal end of the installation part 130. The insertion part 180 has a tapered outer shape and an internal space so that the intraocular lens 1 is deformed into a small piece. A through hole is formed in the main body 100. The through hole extends from the proximal end of the main body cylindrical part 110 toward the distal end of the insertion part 180.

The main body 100 of the embodiment is manufactured by coupling a plurality of members. More specifically, a member formed by integrally molding the main body cylindrical part 110, a right and left wall part 140, a holding part 160, and the insertion part 180 is coupled to the setting part 170 and a top plate part 150 as separate members. Each member will be described below.

<1-2-1. Main Body Cylindrical Part>

The main body cylindrical part 110 includes an overhanging part 111, a front engagement part 112, a rear engagement part 113, and a front inclined part 114. The main body cylindrical part 110 is formed such that its transverse section has a substantially rectangular shape. The overhanging part 111 to be gripped by the user with the fingers is connected to an outer wall of the main body cylindrical part 110, the outer wall being slightly closer to the distal end side than the proximal end. The overhanging part 111 is a plate-shaped member, and sticks out from the outer wall of the main body cylindrical part 110 in a direction substantially orthogonal to the extrusion axis A. The area of a portion which overhangs in the right-left direction in the overhanging part 111 is larger than the area of a portion which overhangs in the up-down direction in the overhanging part 111.

The main body cylindrical part 110 includes the front engagement part 112 and the rear engagement part 113 on the outer wall on the bottom face side. The rear engagement part 113 is formed between the proximal end of the main body cylindrical part 110 and the overhanging part 111. The rear engagement part 113 is a hole for engaging with a front blade part 351 (described later with reference to FIG. 9) of the plunger 300. The front engagement part 112 is formed between the distal end of the main body cylindrical part 110 and the overhanging part 111. The front engagement part 112 has a hole with the same opening area as that of the hole of the rear engagement part 113.

The front inclined part 114 is formed at the distal end of the lower outer wall of the main body cylindrical part 110. The front inclined part 114 is formed by inclining frontward a wall portion forming the main body cylindrical part 110.

When the main body cylindrical part 110 is viewed in the direction of the distal end and the proximal end, the hollow area of the distal end of the main body cylindrical part 110 is made smaller by the front inclined part 114 than the hollow area of the proximal end of the main body cylindrical part 110. The front inclined part 114 serves as an advance regulation member that regulates the advance of the plunger 300. When the front inclined part 114 abuts against an inclined surface 353 (see FIG. 9) provided substantially in the center of the plunger 30 in the front-back direction, the advance of the plunger 300 stops.

<1-2-2. Installation Part>

The installation part 130 includes the right and left wall part 140, the top plate part 150, the holding part 160, and the setting part 170. The intraocular lens 1 is disposed in the installation part (i.e., means for installing) 130 in a state where at least one support part 3 is placed closer to the proximal end than the optical part 2.

<Right and Left Wall Part>

The right and left wall part 140 is connected to the distal end of the main body cylindrical part 110. The right and left wall part 140 includes a right wall and a left wall. The right wall extends from a right end of the distal end of the main body cylindrical part 110 to the distal end direction. The left wall extends from a left end of the distal end of the main body cylindrical part 110 to the distal end direction. The right and left walls extend parallel to each other. The right and left walls are orthogonal to a horizontal plane including the extrusion axis A. The right and left walls are formed such that the distance therebetween is made smaller than the maximum outside shape of the intraocular lens 1 and slightly larger than the diameter of the optical part 2 of the intraocular lens 1.

<Top Plate Part>

The top plate part 150 is a member having a substantially flat plate shape. The top plate part 150 is connected to an upper end of the distal end of the main body cylindrical part 110, an upper end of the right and left wall part 140, and an upper end of the proximal end of the insertion part 180 (described later in detail). An opening above the extrusion axis A, which is formed by the main body cylindrical part 110, the right and left wall part 140, and the insertion part 180, is covered with the top plate part 150. Therefore, a surface of the top plate part 150, which faces the direction of the extrusion axis A (a surface facing an optical surface of the optical part 2), serves as an inner wall surface (inner surface) of the cylindrical main body 100. The other surface of the top plate part 150 serves as an outer wall surface (outer surface) of the main body 100. Specifically, the inner wall surface of the top plate part 150 serves as an inner wall surface of a passage part 132 (see FIG. 7). The passage part 132 is a passage for allowing the intraocular lens 1 to pass from an optical part installation part 131 (see FIG. 7) to a tapered part 181 (see FIG. 7).

<Top Plate Part/Outer Wall Surface>

The outer wall surface side of the top plate part 150 will be described with reference to FIG. 4. FIG. 4 is an explanatory schematic view when the top plate part 150 is viewed from above. A dotted line of FIG. 4 is the contour of the intraocular lens 1. The dotted line indicates the position of the intraocular lens 1 in a state of the intraocular lens insertion device 10 (the insertion state) where the intraocular lens 1 can be extruded by the plunger 300. An injection part 151 and movement regulating holes 152 are formed on the outer wall surface of the top plate part 150.

The injection part 151 includes a needle guide part 153 and an injection port 154. In the embodiment, part of the outer wall of the top plate part 150 is protruded outward (upward) to form the rib-shaped needle guide part 153. The needle guide part 153 is formed to have an inverted V shape whose vertex of the bend is located in the distal end direction of the extrusion axis A. An outward protruding portion of the needle guide part 153 is formed such that the height of the protruding portion is progressively increased toward the distal end. The injection port 154 is formed at an inner vertex portion of the inverted V shape. The injection port 154 is formed by forming a hole penetrating an outer surface and inner surface of the top plate part 150. The injection port 154 has an opening are through which an injection needle for injecting a lubricant, such as a viscoelastic substance, into the installation part 130 can pass. When the needle guide part 153 is provided, the shape of the needle guide part 153 may be changed as appropriate. For example, the needle guide part 153 may have a ring shape instead of a V-shape. Moreover, instead of the rib shape, the needle guide part 153 may be formed by depressing part of the outer wall of the top plate part 150. In this case, a stepped portion formed by the depression serves as the needle guide part 153.

The top plate part 150 further includes the pair of movement regulating holes 152. The pair of movement regulating holes 152 is provided at positions substantially in the middle of the top plate part 150 in the front-back direction and at the right and left ends of the top plate part 150. When the intraocular lens insertion device 10 is accommodated in a casing (not illustrated), movement regulating protrusions provided to the casing penetrate the movement regulating holes 152 of the top plate part 150. Therefore, the movement regulating protrusions provided to the casing and the movement regulating holes 152 of the top plate part 150 are fitted to each other to regulate the movement of the intraocular lens insertion device 10 accommodated in the casing.

In the embodiment, the pair of movement regulating holes 152 is formed on both sides of the inverted V shaped protruding portion forming the needle guide part 153. Therefore, the inverted V shaped protruding portion serving as the needle guide part 153 is formed between the movement regulating holes 152 and the injection port 154. In other words, the needle guide part 153 is formed to intersect with a straight line connecting each movement regulating hole 152 and the injection port 154 (blocking a space between each movement regulating hole 152 and the injection port 154). Therefore, in the intraocular lens insertion device 10 of the embodiment, the needle guide part 153 can prevent the misinsertion of the injection needle into the movement regulating hole 152.

In the embodiment, when the intraocular lens insertion device 10 upon insertion (in the insertion state) is viewed from above, the injection port 154 is formed outward of a front support part 3A (in other words, on the opposite side to the optical part 2 side with respect to the front support part 3A). This will be described in more detail. Assume that a straight line passing the center of the optical part 2 and the proximal end of the front support part 3A is a first straight line. Furthermore, assume that a straight line passing the center of the optical part 2 and being parallel to the extrusion axis A is a second straight line. In this case, the injection port 154 is formed in a region surrounded by the first and second straight lines on the outer side of the front support part 3A. Moreover, the injection port 154 is formed closer to the proximal end side than the tapered part 181 (described in detail below) where a tapered inner wall is formed. Specifically, the injection port 154 is provided in an area of the passage part 132 (see FIG. 7) for allowing the intraocular lens 1 installed in the installation part 130 to pass through to the insertion part 180 (see FIGS. 1, 2, 3A, 3B, and the like). Therefore, the viscoelastic substance injected from the injection port 154 is simultaneously filled in the intraocular lens 1 installed in the installation part 130 and the area where the intraocular lens 1 advances.

<Top Plate Part/Inner Wall Surface>

Figure 5:
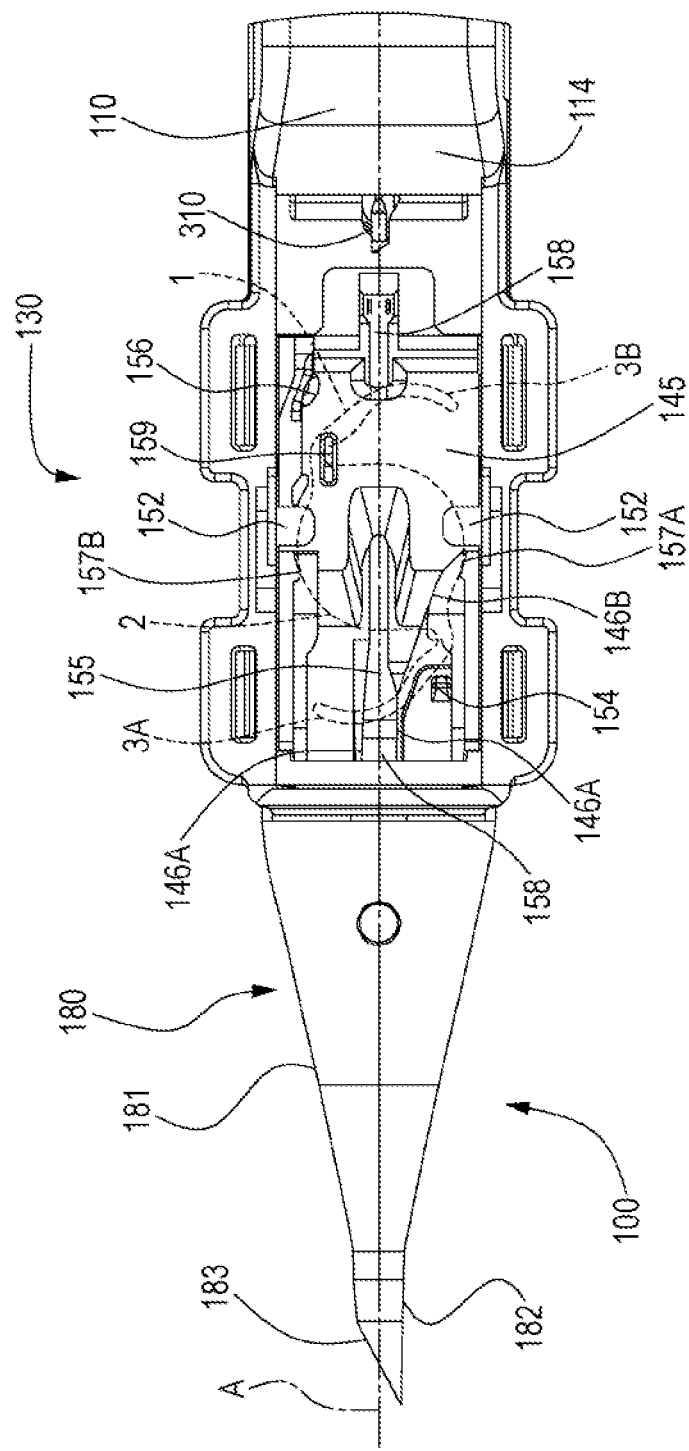
FIG. 5 is a partial view (bottom view) of the intraocular lens insertion device of FIG. 1, mainly illustrates an insertion part and an installation part, and omits the setting part and a holding part.
Figure 6A:
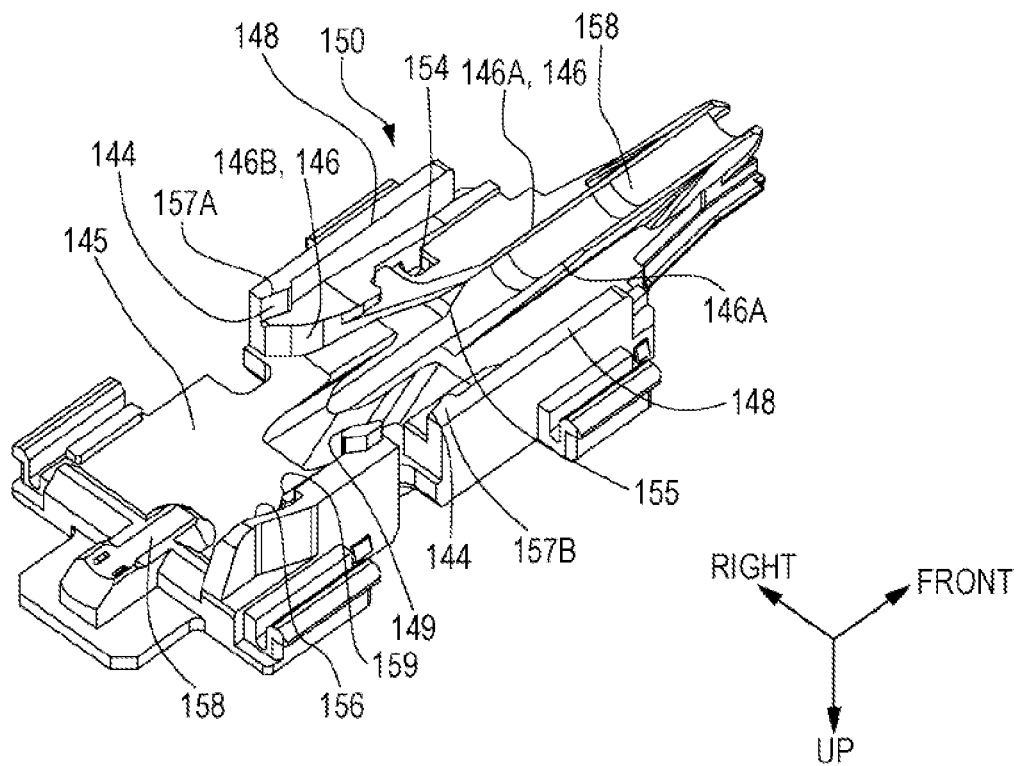
Figure 6B:
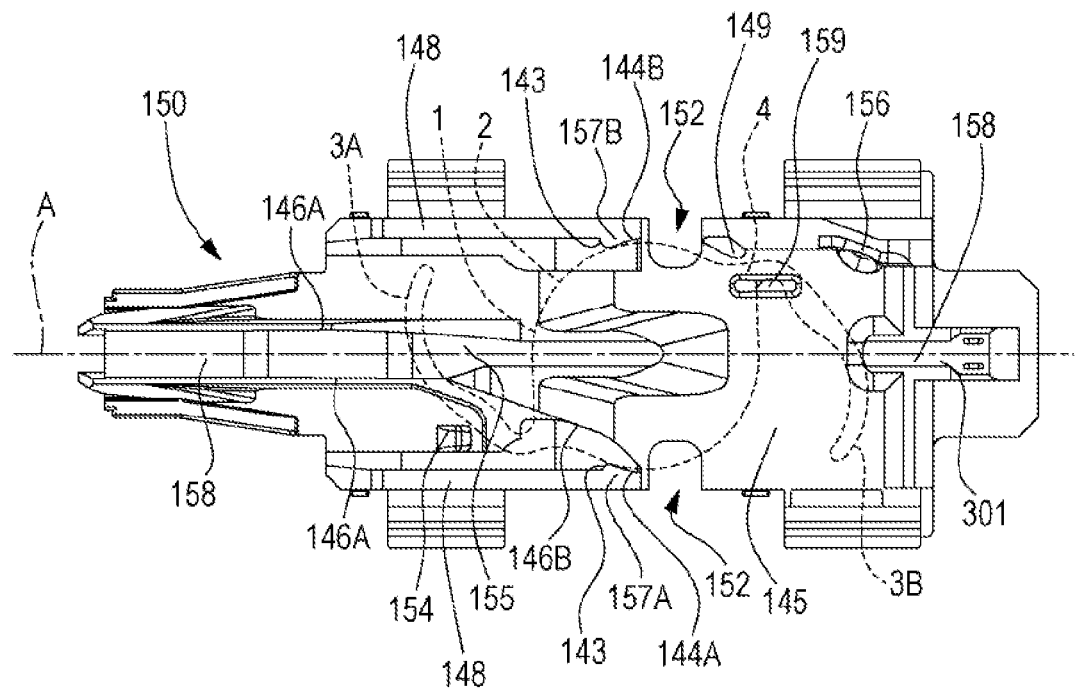

The inner wall surface of the top plate part 150 will be described with reference to FIGS. 5, 6A, and 6B. FIG. 5 is an explanatory view of the top plate part 150 as viewed from below in a state where the holding part 160 and the setting part 170 are removed from the intraocular lens insertion device 10. FIGS. 6A and 6B illustrate components of the top plate part 150 removed from the main body 100 for explaining the top plate part 150. FIG. 6A is a perspective view of the top plate part 150 as viewed from obliquely left behind. FIG. 6B is a bottom view of the top plate part 150. The front side on the paper of FIGS. 6A and 6B is the down side upon the start of insertion. Moreover, dotted lines of FIGS. 5 and 6B are the contour of the intraocular lens 1. The dotted line indicates the position of the intraocular lens 1 in the state (the insertion state) of the intraocular lens insertion device 10 where the extrusion with the plunger 300 is possible.

The inner wall surface of the top plate part 150 includes a deformation guide part 146, a sideward deformation suppression part 149, a stress generation part 156, abutment parts 157A and 157B, an axial alignment groove 158, an upward deformation suppression part 159, and an upward depressed part 145. The deformation guide part 146 includes parallel guide surfaces 146A and an inclined guide surface 146B.

In the embodiment, the inner wall surface of the top plate part 150 is formed unevenly. The uneven surface is asymmetric with respect to the right-left direction. Plate-shaped right and left plates 148 protruding downward are connected to right and left ends on the inner wall surface of the top plate part 150. The distance between the right and left plate 148 on the right side and the right and left plate 148 on the left side is smaller than the maximum diameter of the intraocular lens 1 and slightly larger than the diameter of the optical part 2.

The upward depressed part 145 is provided on the proximal end side of the inner wall surface of the top plate part 150. The upward depressed part 145 is formed in such a manner as to provide a space above a first contact part 175A and a first contact part 175B (see FIG. 7) of the setting part 170 (see FIGS. 8A, 8B, and the like) in a state where the setting part 170 is pressed in. The inner wall surface of the top plate part 150 is depressed upward to form the upward depressed part 145. Although the details will be described below, in the embodiment, when the setting part 170 is pressed in and the intraocular lens 1 is deformed and positioned, a rear support part 3B of the intraocular lens 1 is located in the upward depressed part 145.

The sideward deformation suppression part 149 is formed at a left end portion (a lower right end portion in FIG. 6A and an upper end portion in FIG. 6B) of the inner wall surface of the top plate part 150. As illustrated in FIG. 6B, the sideward deformation suppression part 149 is formed at a position facing an outer surface of a root portion 4 of the rear support part 3B of the intraocular lens 1 when the setting part 170 is pressed in. A surface facing to the right is formed on the sideward deformation suppression part 149. The sideward deformation suppression part 149 of the embodiment suppresses leftward deformation of the rear support part 3B (specifically the root portion 4). The surface, which faces to the right, of the sideward deformation suppression part 149 has a tapered shape facing slightly downward. In other words, the sideward deformation suppression part 149 is formed in such a manner as to suppress the large deformation of the intraocular lens 1 due to an interference between the sideward deformation suppression part 149 and an end portion of the intraocular lens 1 upon the movement of the intraocular lens 1 in the direction of the extrusion axis A.

The axial alignment groove 158 is provided on the inner wall surface of the top plate part 150 to prevent the axial misalignment of an extrusion member 310 and an extrusion rod 330 (see FIG. 9) of the plunger 300 that is advancing. The axial alignment groove 158 is formed by curving the inner wall surface upward. The axial alignment groove 158 is formed to have a curved shape corresponding to the shape of a transverse section of the extrusion rod 330 of the plunger 300. The axial alignment groove 158 is formed to extend a center portion of the inner wall surface substantially parallel to the extrusion axis A (in the front-back direction).

The axial alignment groove 158 is separated into the distal end side of the upward depressed part 145 and the rear end side of the upward depressed part 145. The upward deformation suppression part 159 is formed in the depressed area of the upward depressed part 145. The upward deformation suppression part 159 is located above the position of the root portion 4 of the rear support part 3B of the intraocular lens 1 when the setting part 170 is pressed in. The upward deformation suppression part 159 is formed on the left side of the axial alignment groove 158 (in the upper side of FIG. 6B) when the top plate part 150 is viewed from the proximal end direction. The stress generation part (i.e., means for providing) 156 is provided at a position interfering with an off-axis movement part (i.e., means for pressing) 177 (see FIG. 7) described below. When the off-axis movement part 177 moves upward, the off-axis movement part 177 comes into contact with the stress generation part 156 to be deformed, and presses the rear support part 3B forward. The details will be described below. Moreover, the abutment parts 157A and 157B will be also described below in detail.

The upward deformation suppression part 159 is formed protruding downward from the depressed surface of the upward depressed part 145. A substantially flat surface that is in abutment with the intraocular lens 1 is formed at a lower end of the upward deformation suppression part 159 protruding downward. The substantially flat surface of the upward deformation suppression part 159 has a substantially rectangular shape having a longitudinal direction along the distal end direction (front-back direction) as viewed from below. The upward deformation suppression part 159 of the embodiment prevents the amount of upward deformation of the rear support part 3B from becoming larger than a planned amount.

The deformation guide part 146 includes the parallel guide surfaces 146A and the inclined guide surface 146B. The deformation guide part 146 may be formed by depressing or protruding the inner wall of the main body 100. In the embodiment, the deformation guide part 146 is formed by protruding part of the wall surface of the top plate part 150 downwardly. Therefore, the deformation guide part 146 is formed in a simple method. The parallel guide surfaces 146A are provided on right and left ends of the curved axial alignment groove 158. Each of the two parallel guide surfaces 146A provided on the right and left ends of the axial alignment groove 158 has a curved shape being a downward convex. The two parallel guide surfaces 146A extend in the direction parallel to the extrusion axis A (the front-back direction).

A distal end of the inclined guide surface 146B is connected to a proximal end of the right parallel guide surface 146A. The inclined guide surface 146B is formed by depressing the inner wall surface of the top plate part 150 upwardly. The inclined guide surface 146B includes a guide slope facing the proximal end direction. The guide slope is a smooth slope that comes closer to the extrusion axis A toward the distal end side. The inclined guide surface 146B is formed in such a manner as to increase the amount of depression progressively toward the proximal end direction. The amount of depression of the inclined guide surface 146B at its proximal end is set to substantially the same as the amount of depression of the upward depressed part 145. Therefore, the proximal end of a depressed bottom surface forming the inclined guide surface 146B is smoothly connected to a distal end of a depressed bottom surface of the upward depressed part 145.

The guide slope of the inclined guide surface 146B is formed in such a manner as to reduce the width of the slope in the up-down direction progressively toward the distal end. The movement regulating holes 152 that penetrate the outer and inner wall surfaces are provided at the right and left ends of the inner wall surface of the top plate part 150. The proximal end of the inclined guide surface 146B is positioned slightly closer to the distal end side than the movement regulating holes 152. Therefore, when the intraocular lens insertion device 10 upon extrusion is viewed from above, the proximal end of the inclined guide surface 146B is positioned substantially above the right and left ends of the optical part 2. Moreover, when the intraocular lens insertion device 10 upon extrusion is viewed from above, the proximal end of the axial alignment groove 158 on the distal end side is positioned above the center of the optical part 2. The deformation guide part 146 (including the parallel guide surfaces 146A and the inclined guide surface 146B in the embodiment) guides the deformation and movement of the front support part 3A upon the tacking of the front support part 3A. Consequently, the front support part 3A can be bent into a predetermined shape. Here, "tacking" indicates to deform and move at least one of the front support part 3A and the rear support part 3B to a position facing the optical surface of the optical part 2 to put the front support part 3A and/or the rear support part 3B and the optical part 2 in a state where they are laid over one another.

<Abutment Part>

The abutment parts 157A and 157B are formed at both proximal ends of the right and left plates 148 provided at the right and left ends of the top plate part 150. The abutment part 157A is provided on the right side. The abutment part 157B is provided on the left side to face the abutment part 157A. The abutment part 157B provided on the left side is positioned on a side where the root portion 4 of the rear support part 3B is located with respect to the extrusion axis A. The two abutment parts 157A and 157B prevent the occurrence of deformation failure in the intraocular lens 1 due to the influence of the restoring force of the bent support part 3. The shapes of the abutment parts 157A and 157B are substantially symmetric with respect to the axial alignment groove 158. In the embodiment, the abutment parts 157A and 157B have substantially the same shape. However, the abutment part 157B is slightly larger than the abutment part 157A. Therefore, stresses given by the two abutment parts 157A and 157B to the intraocular lens 1 are different from each other. In other words, the stress given by the abutment part 157B to the intraocular lens 1 from the left side where the root portion 4 of the rear support part 3B is located is larger than the stress given by the abutment part 157A to the intraocular lens 1 from the opposite side. Hence, the rotation of the intraocular lens 1 counterclockwise in FIG. 6B due to the influence of the restoring force of the bent (tacked) rear support part 3B is prevented by the abutment parts 157A and 157B. The shapes of the two abutment parts 157A and 157B may be different from each other.

Figure 19A:
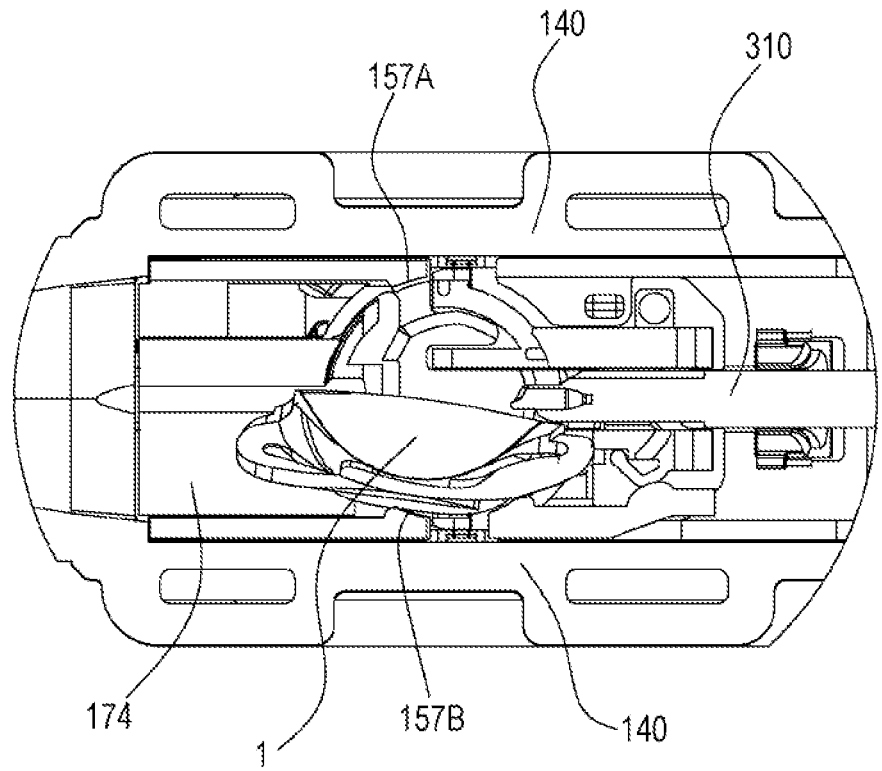
FIGS. 19A and 19B are explanatory schematic views for explaining abutment parts.
Figure 19B:
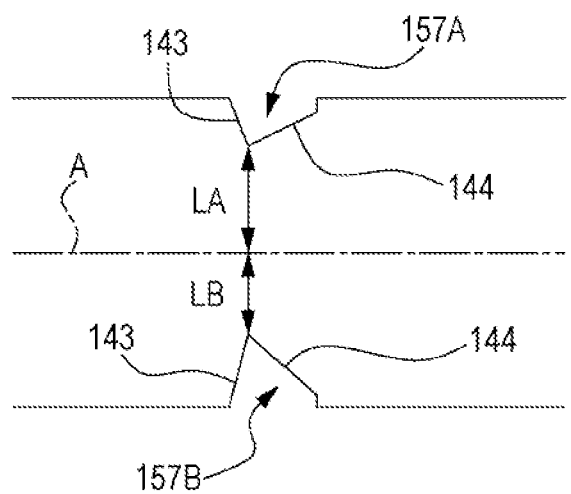

The abutment parts 157A and 157B each include an escape slope 143 facing the distal end direction and a slope 144 (144A, 144B) facing the proximal end direction (see also FIG. 19B). The slope 144 is inclined to be closer to the extrusion axis A toward the distal end. In other words, the distance in the right-left direction (the direction horizontally orthogonal to the extrusion axis A) between the slope 144 (144A) of the right abutment part 157A and the slope 144 (144B) of the left abutment part 157B is gradually reduced toward the distal end side. A distal end of the escape slope 143 is connected to a proximal end of a surface, which faces the axial alignment groove 158, of the right and left plate 148. A distal end of the slope 144 is connected to a proximal end of the escape slope 143. A proximal end of the slope 144 serves as a proximal end portion of the right and left plate 148. The connected portion between the proximal end of the escape slope 143 and the distal end of the slope 144 is formed into a curved surface. The two abutment parts 157A and 157B are positioned respectively on the right and left sides of the extrusion axis A on the same plane orthogonal to the extrusion axis A. In other words, the two abutment parts 157A and 157B are formed at the same position in the axial direction of the extrusion axis A.

As illustrated in FIG. 6B, when the intraocular lens insertion device 10 upon insertion is viewed from below, the distance between the extrusion axis A and the distal end of the slope 144 of the abutment part 157B is shorter than the distance between the extrusion axis A and the distal end of the slope 144 of the abutment part 157A. Therefore, the stress given by the abutment part 157B to the intraocular lens 1 from the left side is larger than the stress given by the abutment part 157A to the intraocular lens 1 from the opposite side (right side). In the embodiment, the sizes of the two abutment parts 157A and 157B and the distances between the two abutment parts 157A and 157B and the extrusion axis A are different from each other. However, by changing at least any of the shapes, sizes, distances from the extrusion axis A, materials, states of the surfaces of the slopes 144 (for example, the grading of the surfaces of the slopes 144, the states of projections and depressions, and materials to be attached to the surfaces of the slopes 144) of the two abutment parts 157A and 157B, the stresses given to the intraocular lens 1 from the two abutment parts 157A and 157B can be discriminated. Incidentally, the shapes of the two abutment parts 157A and 157B include the angle of the slope 144 with respect to the extrusion axis A.

Moreover, the distance of a straight line connecting the distal end of the right slope 144 (144A) to the distal end of the left slope 144 (144B) is slightly smaller than the diameter of the optical part 2 of the intraocular lens 1. On the other hand, the distance of a straight line connecting the proximal end of the right slope 144 (144A) to the proximal end of the left slope 144 (144B) is slightly larger than the diameter of the optical part 2 of the intraocular lens 1. The angle of intersection of the slope 144 with respect to a plane orthogonal to the extrusion axis A is larger than the angle of intersection of the escape slope 143 with respect to the plane orthogonal to the extrusion axis A. Moreover, the slope 144 is formed to curve slightly outward.

<Holding Part>

Figure 7:
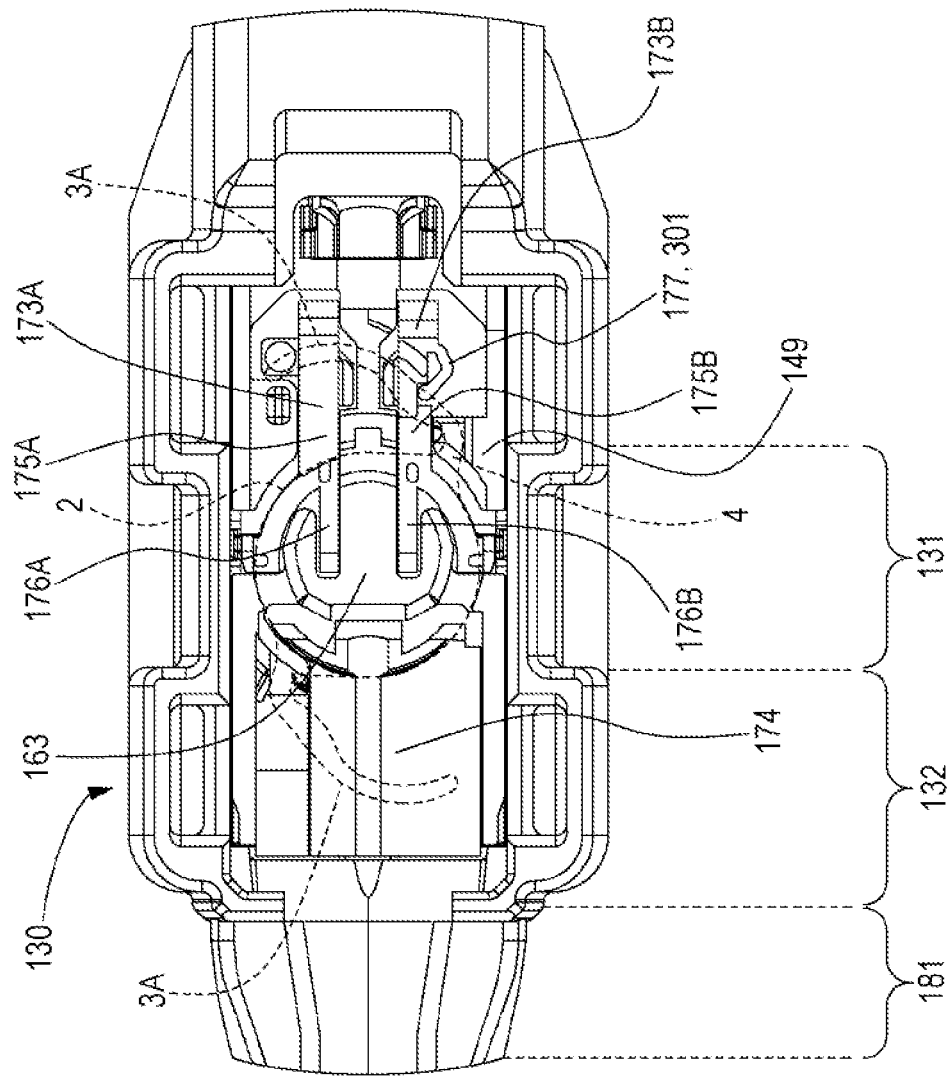
FIG. 7 is a partial view of the intraocular lens insertion device of FIG. 1, mainly illustrates the installation part, and omits the top plate part.
Figure 8A:
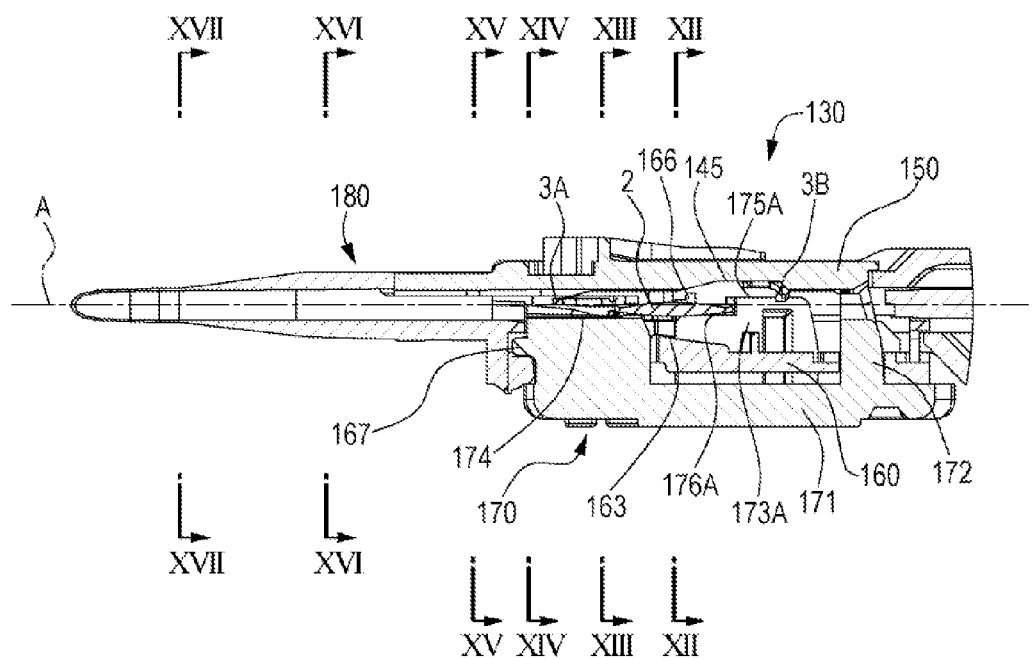
Figure 8B:
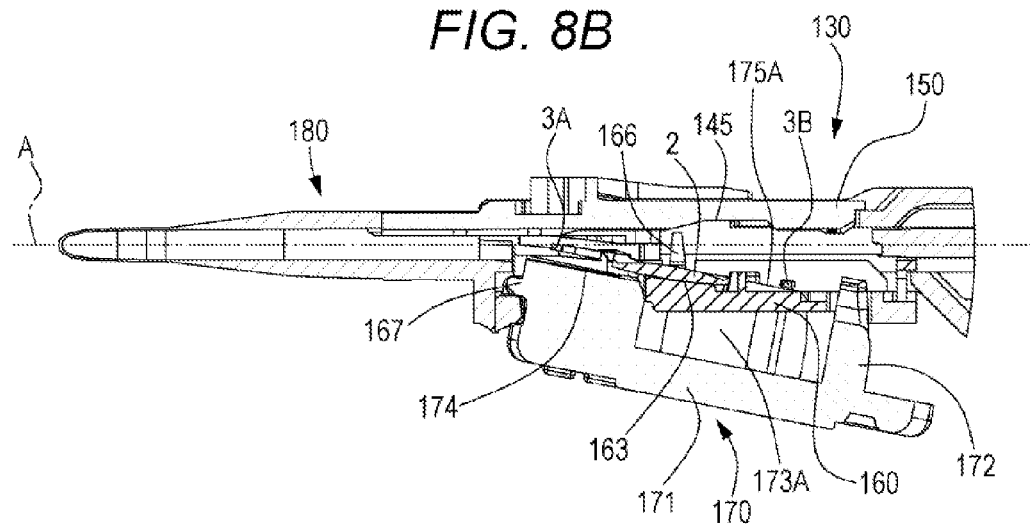

The holding part 160 will be described. The holding part 160 holds the intraocular lens 1 while the intraocular lens insertion device 10 is in the storage state. As illustrated in FIGS. 3A and 3B, the holding part 160 is connected to the lower end of the right and left wall part 140. As illustrated in FIGS. 8A and 8B, the holding part 160 includes an intraocular lens storage part 163 and a holding protruding part 166. The intraocular lens storage part 163 and the holding protruding part 166 are formed on a substantially plate-shaped base. The base has a through hole that allows the first contact part 175A, the first contact part 175B, a second contact part 176A, and a second contact part 176B (see FIG. 7) of the setting part 170 described below to move in the up-down direction.

The intraocular lens storage part 163 comes into contact with the bottom face of the optical part 2 of the intraocular lens 1 and holds the intraocular lens 1 when the intraocular lens insertion device 10 is in the storage state. Specifically, the intraocular lens storage part 163 of the embodiment holds the optical part 2 at a position away from the extrusion axis A. The holding protruding part 166 is bent upon the manufacture of the intraocular lens insertion device 10. A distal end portion of the bent holding protruding part 166 is located above an optical surface 2A of the intraocular lens 1 and regulates the upward movement of the intraocular lens 1.

<Setting Part>

The setting part 170 moves the intraocular lens 1 held by the holding part 160 to a standby position where the intraocular lens 1 can be extruded by the extrusion member 310, and positions the intraocular lens 1 at the standby position. As illustrated in FIG. 7, in a state where the intraocular lens 1 is positioned at the standby position, the optical part 2 of the intraocular lens 1 is installed in the optical part installation part 131 of the installation part 130 (see FIGS. 1, 2, 3A and 3B). When the extrusion member 310 is pressed toward the distal end side, the intraocular lens 1 passes through the passage part 132 to move to the tapered part 181, and is discharged into the eye from a bevel part 183 (see FIGS. 12A to 12E) of the insertion part 180. The width in the right-left direction (a direction perpendicular to the extrusion axis A and parallel to the optical surface of the optical part 2) of the passage part 132 is formed to be larger than the width in the right-left direction of the optical part 2. The tapered part 181 includes the inner wall tapered toward the distal end side. In other words, the cross-sectional area of the tapered part 181 in the direction perpendicular to the extrusion axis A is progressively reduced toward the distal end side. The optical part 2 is discharged from the bevel part 183 in a state of being completely bent by the tapered part 181.

The setting part 170 includes a base part 171 (see FIGS. 8A and 8B), a rotation support base 172 (see FIGS. 8A and 8B), a right protruding part 173A (see FIGS. 7, 8A and 8B), a left protruding part 173B (see FIG. 7), a distorted part 174 (see FIGS. 7, 8A, 8B, and 21A to 21F), and a pivot part 167 (see FIGS. 8A and 8B). The base part 171 is a plate-shaped member, and includes an inner wall surface facing the holding part 160 and an outer wall surface facing outward (downward). The rotation support base 172 is formed at a position slightly closer to the distal end side than the proximal end, on an inner wall surface of the setting part 170. The rotation support base 172 has a shape protruding upward from the base part 171. The right protruding part 173A and the left protruding part 173B are formed on the distal end side of the rotation support base 172 of the base part 171. The right protruding part 173A and the left protruding part 173B have a shape protruding upward from the base part 171.

As illustrated in FIG. 7, the right protruding part 173A is formed on the right side of the center line in the front-back direction passing the center of the base part 171. The right protruding part 173A includes the first contact part 175A and the second contact part 176A at its upper end portion. The second contact part 176A is formed closer to the distal end side than the first contact part 175A. The left protruding part 173B is formed on the left side of the center line in the front-back direction passing the center of the base part 171. The left protruding part 173B includes the off-axis movement part 177, the first contact part 175B, and the second contact part 176B at its upper end portion. The first contact part 175B is positioned closer to the distal end side than the off-axis movement part 177. The second contact part 176B is positioned closer to the distal end side than the first contact part 175B. Although the details will be described below, the first contact parts 175A and 175B move (are mobile) upward together with the base part 171 to position the rear support part 3B at the standby position. The second contact parts 176A and 176B move (are mobile) upward together with the base part 171 to move the optical part 2 held by the holding part 160 to the standby position and position the optical part 2 at the standby position.

As illustrated in FIG. 8A, the height of portions (parts of the upper end portions), which come into contact with the rear support part 3B, of the first contact parts 175A and 175B (only 175A is illustrated in FIGS. 8A and 8B) is different from the height of portions (parts of the upper end portions), which come into contact with the optical part 2, of the second contact parts 176A and 176B (only 176A is illustrated in FIGS. 8A and 8B). In other words, when a plane passing the center in the thickness direction of the optical part 2 and being perpendicular to the optical axis of the optical part 2 is a central plane P (see FIG. 13A) of the intraocular lens 1, the portions, which come into contact with the rear support part 3B, of the first contact parts 175A and 175B are displaced in a direction intersecting with the central plane P from the portions, which come into contact with the optical part 2, of the second contact parts 176A and 176B. Therefore, when the intraocular lens 1 is positioned at the standby position by the setting part 170, the rear support part 3B is held at the position displaced from the central plane P of the intraocular lens 1. The second contact parts 176A and 176B move the optical part 2 onto the extrusion axis A. In other words, the upper surfaces of the second contact parts 176A and 176B serve as mounting surfaces on which the optical part 2 at the standby position is mounted. The off-axis movement part 177 is a member different from the plunger 300. The off-axis movement part 177 deforms with the upward movement (moving action) of the setting part 170, and presses the rear support part 3B from a direction different from the extrusion axis A. Consequently, the off-axis movement part 177 deforms and moves the rear support part 3B. In other words, the off-axis movement part 177 deforms and moves the support part 3 (the rear support part 3B) of the intraocular lens 1 installed in the installation part 130 by pressing the support part 3 from the direction different from the extrusion axis A.

The distorted part 174 is formed on a passage wall of the passage part 132, the passage wall facing one optical surface (an optical surface facing downward in the embodiment) of the optical part 2 (i.e., a passage wall on an inner lower side of the passage part 132). The details will be described below with reference to FIGS. 21A to 21F. The distorted part 174 is distorted in a concave shape toward a direction away from the extrusion axis A (downward in the embodiment) as viewed from the direction of the extrusion axis A. Furthermore, the distorted part 174 of the embodiment has an increasingly larger amount of distortion (curvature) toward the distal end side. In other words, the radius of curvature of the concave distorted surface of the distorted part 174 is progressively reduced toward the distal end side. The optical part 2 slides over the distorted surface of the distorted part 174, and accordingly bends gradually due to the action of surface tension of the viscoelastic substance. Therefore, the optical part 2 is prevented from being bent sharply in the tapered part 181. Thus, the possibility of deformation failure of the intraocular lens 1 is reduced.

As illustrated in FIGS. 8A and 8B, the pivot part 167 is a protruding member that protrudes from an end on the distal end side of the base part 171 further toward the distal end side. The pivot part 167 fits into a groove or hole provided in the vicinity of a distal end portion of the installation part 130 (see FIGS. 1, 2, 3A, and 3B) in such a manner as to have an appropriate clearance in between with the groove or hole. The base part 171 can rotate about the axis of rotation traversing the pivot part 167 in the right-left direction with respect to the main body 100.

<1-2-3. Insertion Part>

As illustrated in FIGS. 12A to 12E, the insertion part 180 includes the tapered part 181 and the nozzle part 182. A rear end of the insertion part 180 is connected to the distal end of the installation part 130. As described above, the tapered part 181 has a shape tapered toward the distal end. Moreover, the tapered part 181 is formed to have the shape of a substantially elliptic transverse section. Since the tapered part 181 has a tapered shape, the distance between the extrusion axis A and the inner wall of the tapered part 181 is progressively reduced toward the distal end. A distal end of the tapered part 181 is connected to the nozzle part 182.

The shape of a transverse section of the nozzle part 182 is substantially circular. The bevel part 183 is formed on the distal end side of the nozzle part 182. The bevel part 183 forms an opening inclining toward the left side with respect to a plane orthogonal to the extrusion axis A. Moreover, the opening of the nozzle part 182 has the opening diameter that allows the extrusion member 310 and the extrusion rod 330 of the plunger 300 to pass through. The bevel part 183 of the intraocular lens insertion device 10 of the embodiment has a shape obtained by cutting a proximal end of the opening end face forming the bevel part 183 in the proximal end direction of the extrusion axis A. The shape on the proximal end side of the bevel part 183 is formed into a shape cut in the proximal end direction, so that the outer diameter of the transverse section of the nozzle part 182 can be deformed into a smaller diameter when the nozzle part 182 is inserted into an incision of the patient's eye. Therefore, the nozzle part 182 can be easily inserted into the incision of the patient's eye.

<1-3. Plunger>

The plunger 300 of the embodiment will be described with reference to FIGS. 9 and 10A to 10E. The plunger 300 of the embodiment includes the extrusion member 310, the extrusion rod 330, a shaft base 350, and the pressing part 370. The plunger 300 of the embodiment serves also as a movement part 301 for moving (i.e., tacking) the support part 3 of the intraocular lens 1 in a direction approaching the optical part 2. The movement part 301 deforms the support part 3 of the intraocular lens 1 installed in the installation part 130 to move the support part 3 in the direction approaching the optical part 2. The movement part 301 includes a linear movement part (i.e., means for moving) 313 (described below).

The pressing part 370 is formed at a proximal end of the plunger 300. The pressing part 370 is a plate-shaped member extending in a direction orthogonal to the extrusion axis A. The pressing part 370 has a convex shape whose lower end portion protrudes downward as viewed from the proximal end side of the extrusion axis A. When the user presses out the plunger 300, a finger of the user is brought into abutment with the pressing part 370.

The rod-like shaft base 350 extending in the distal end direction of the extrusion axis A (the front-back direction) is connected to the distal end side of the pressing part 370. The shaft base 350 substantially as a whole is formed to have a substantially H shaped transverse section. The shaft base 350 includes the front blade part 351 and a rear blade part 352. The front blade part 351 and the rear blade part 352 both have a blade shape, and are both formed on the bottom face side of the shaft base 350. Moreover, the front blade part 351 is provided on a distal end side of the shaft base 350. The rear blade part 352 is provided on a proximal end side of the shaft base 350.

The front engagement part 112 or rear engagement part 113 (see FIG. 2) of the main body 100 is engaged with the front blade part 351, and accordingly the plunger 300 is locked with the main body 100. Consequently, the backward movement of the plunger 300 is prevented or suppressed while the plunger 300 is positioned.

In the intraocular lens insertion device 10 of the embodiment, the position of the plunger 300 in a case where the rear engagement part 113 is engaged with the front blade part 351 is an initial position to start the forward press of the intraocular lens 1. Similarly, the position of the plunger 300 in a case where the front engagement part 112 is engaged with the front blade part 351 is a standby position to start the insertion of the intraocular lens 1 into the patient's eye.

At the initial position, a distal end of the plunger 300 is placed slightly closer to the distal end side than a proximal end of the installation part 130. At the standby position, the distal end of the plunger 300 is placed substantially at the midpoint of the length of the insertion part 180. At the initial position, the plunger 300 is not in contact with the intraocular lens 1 disposed in the installation part 130.

The shaft base 350 having a substantially H-shaped transverse section is inserted into the main body 100 having a substantially rectangular transverse section. As a result, the rotation of the plunger 300 in the circumferential direction of the extrusion axis A with respect to the main body 100 is prevented.

The extrusion rod 330 is connected to the distal end of the shaft base 350. The extrusion rod 330 is a rod-like member extending in the axial direction of the extrusion axis A. The extrusion rod 330 substantially as a whole is formed to have a transverse section of a substantially circular shape. The length of the shaft base 350 is substantially the same as the length from the proximal end of the installation part 130 to the distal end of the insertion part 180. Moreover, the thickness of the extrusion rod 330 is set in such a manner as that the extrusion rod 330 can pass through the opening of the nozzle part 182 at the distal end of the main body 100.

The extrusion member 310 is connected to a distal end of the extrusion rod 330. As illustrated in FIGS. 10A to 10E, the extrusion member 310 includes a shaft rod 311 and a distal end part 312. The shaft rod 311 is placed on a proximal end side of the extrusion member 310. The distal end part 312 is placed on the distal end side of the extrusion member 310.

The thicknesses of the shaft rod 311 and the distal end part 312 are set in such a manner as that the shaft rod 311 and the distal end part 312 can pass through the opening of the nozzle part 182 at the distal end of the main body 100. In other words, the cross-sectional area of the extrusion member 310 in the direction perpendicular to the extrusion axis A is set in such a manner as that the extrusion member 310 can pass through the nozzle part 182.

The distal end part 312 includes the linear movement part 313, an optical part contact part 314, a protruding part 315, a lower end protrusion 316, a distal end inclined surface 317, a right depressed part 318, and a left depressed part 319. The linear movement part 313 is formed on an upper side of a distal end of the distal end part 312. The optical part contact part 314 is formed on a lower side of the distal end of the distal end part 312.

Figure 10A:
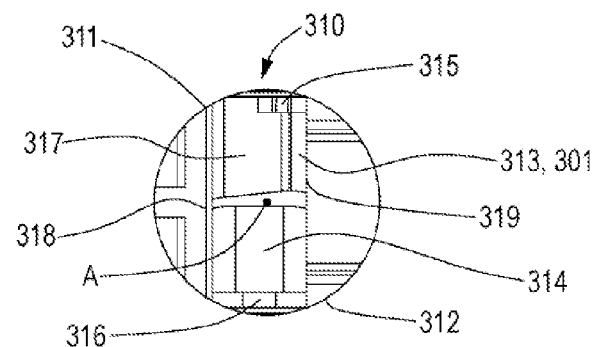
Figure 10B:
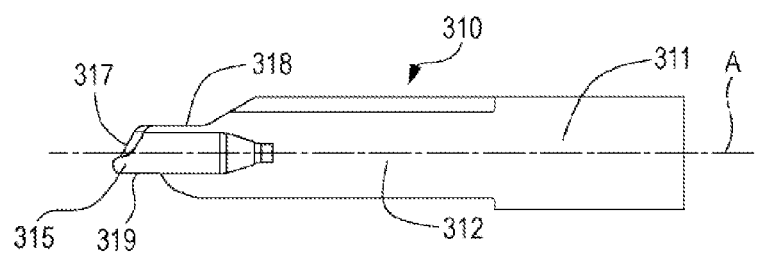
Figure 10C:
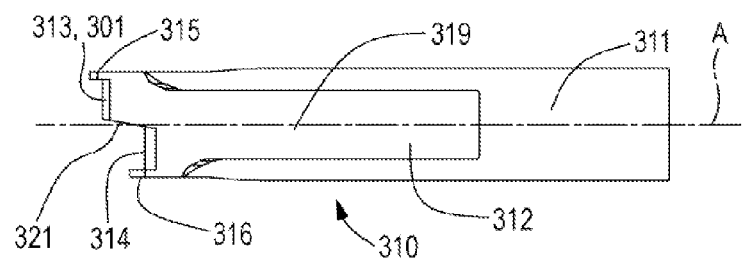
Figure 10D:
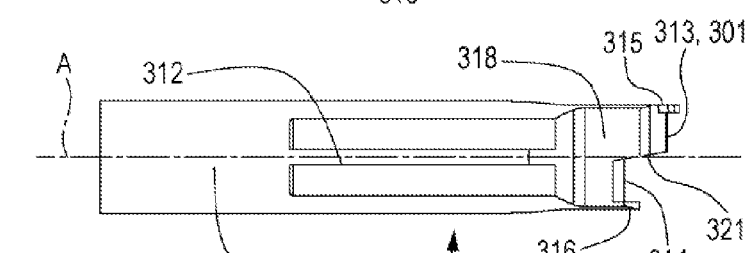
Figure 10E:
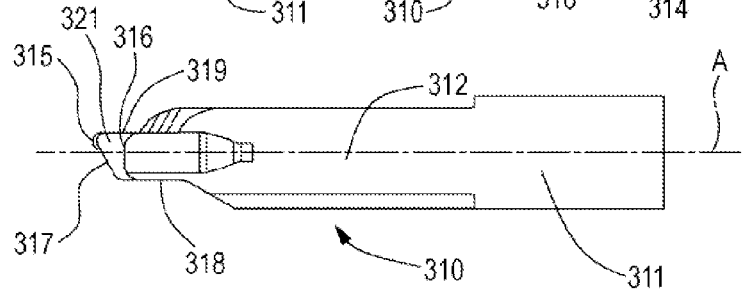

As illustrated in FIG. 10A, the front of the distal end part 312 as viewed from the distal end side of the extrusion axis A includes an area of the optical part contact part 314 and an area of the linear movement part 313. Therefore, the user can tack the rear support part 3B and press out the optical part 2 by simply pressing out the plunger 300. Moreover, as viewed from the distal end side of the extrusion axis A, the width of the optical part contact part 314 in the right-left direction is larger than the width of the linear movement part 313 in the right-left direction. The linear movement part 313 has a protruding shape that protrudes in the distal end direction. Furthermore, a distal end portion of the linear movement part 313 has a curved shape being convex in the distal end direction. Therefore, the rear support part 3B is scratch resistant.

The linear movement part 313 presses the support part 3 by moving linearly along the extrusion axis A. The linear movement part 313 is formed to lean to a side where the proximal end of the rear support part 3B of the intraocular lens 1 installed in the installation part 130 is positioned, as viewed from the distal end side of the extrusion axis A. In other words, an end portion on the distal end side of the linear movement part 313 of the embodiment is placed to lean to the proximal end side (left side) of the rear support part 3B with respect to the extrusion axis A. Therefore, the linear movement part 313 can press a position, which is closer to the proximal end side, of the rear support part 3B. Hence, the deformation and movement of the rear support part 3B is stabilized and the amount of movement can be easily secured as compared with a case where a position close to the distal end side is pressed. The end portion on the distal end side of the linear movement part 313 may be placed at the same position as an end portion on the distal end side of the optical part contact part 314 or at a position closer to the distal end side than the end portion on the distal end side of the optical part contact part 314 in the axial direction of the extrusion axis A. In this case, the rear support part 3B can be extended far toward the distal end side. Accordingly, it is easy to make excellent tacking. In the embodiment, the end portion on the distal end side of the linear movement part 313 is formed at a position closer to the distal end side than the end portion on the distal end side of the optical part contact part 314. Thus, tacking can be made more accurately.

The length of a ridge of the linear movement part 313 as viewed from the side of the extrusion axis A is longer than the thickness of the support part 3 that is in abutment with the linear movement part 313. In other words, the distance of the distal end inclined surface 317 of the linear movement part 313 in the up-down direction (the direction parallel to the optical axis of the optical part 2) is longer than the thickness of the support part 3 in the up-down direction. Moreover, the length of a ridge of the optical part contact part 314 as viewed from the side of the extrusion axis A is longer than the thickness of an optical part side surface 2C that is in abutment with the optical part contact part 314.

A surface 321 of the linear movement part 313, which faces the optical part contact part 314 side (i.e., a bottom face of the linear movement part 313), is inclined to face the distal end direction of the extrusion axis A (forward). Since the bottom face of the linear movement part 313 is inclined, the optical part 2 in abutment with the bottom face of the linear movement part 313 is guided in the direction of the optical part contact part 314. Moreover, right and left end portions of the linear movement part 313 are smoothly connected to the distal end inclined surface 317 and the left depressed part 319.

A distal end surface of the optical part contact part 314 is formed to be a flat surface substantially orthogonal to the extrusion axis A. Each of the right and left end portions of the optical part contact part 314 has a curved surface, and is smoothly connected to the right depressed part 318 and the left depressed part 319. Therefore, the optical part 2 is scratch resistant.

The protruding part 315 is connected to an upper end of the linear movement part 313. The shape of the protruding part 315 is a protruding shape that extends in the distal end direction of the extrusion axis A (forward). The protruding part 315 prevents the upward movement of the rear support part 3B in abutment with the linear movement part 313. The lower end protrusion 316 is formed at a lower end of the optical part contact part 314. The shape of the lower end protrusion 316 is a protruding shape that extends in the distal end direction of the extrusion axis A. The lower end protrusion 316 prevents the downward movement of the optical part 2 in abutment with the optical part contact part 314.

The distal end inclined surface 317 at the distal end portion of the linear movement part 313 is inclined in the direction away from the extrusion axis A with respect to the plane orthogonal to the extrusion axis A. In other words, the distal end inclined surface 317 of the embodiment is inclined to face either the right or left direction orthogonal to both the optical axis of the optical part 2 and the extrusion axis A. More specifically, the distal end inclined surface 317 extends from the end portion on the distal end side of the linear movement part 313 to an opposite direction (to the right side in the embodiment) to the direction where the root portion 4 of the rear support part 3B is located. Moreover, a distal end of the distal end inclined surface 317 is connected to the right end of the linear movement part 313. A proximal end of the distal end inclined surface 317 is connected to a distal end of the right depressed part 318. The distal end inclined surface 317 increases the rigidity of the linear movement part 313.

The right depressed part 318 that is depressed from a right end of the distal end inclined surface 317 in the proximal end direction is formed on a right side surface at the distal end of the distal end part 312. Moreover, the left depressed part 319 that is depressed from the left ends of the linear movement part 313 and the optical part contact part 314 in the proximal end direction is formed on a left side surface at the distal end of the distal end part 312.

Upon insertion of the intraocular lens 1, the root portion 4 of the rear support part 3B is sandwiched between a side wall of the left depressed part 319 and the inner wall of the main body 100. The folded intraocular lens 1 is discharged from the nozzle part 182 in a state where the root portion 4 of the rear support part 3B is secured by the left depressed part 319. Since the folded intraocular lens 1 is discharged in the state where the root portion 4 of the rear support part 3B is secured, the behavior of the intraocular lens 1 upon the restoration in the patient's eye is stabilized.

<1-4. Intraocular Lens>

Figure 11A:
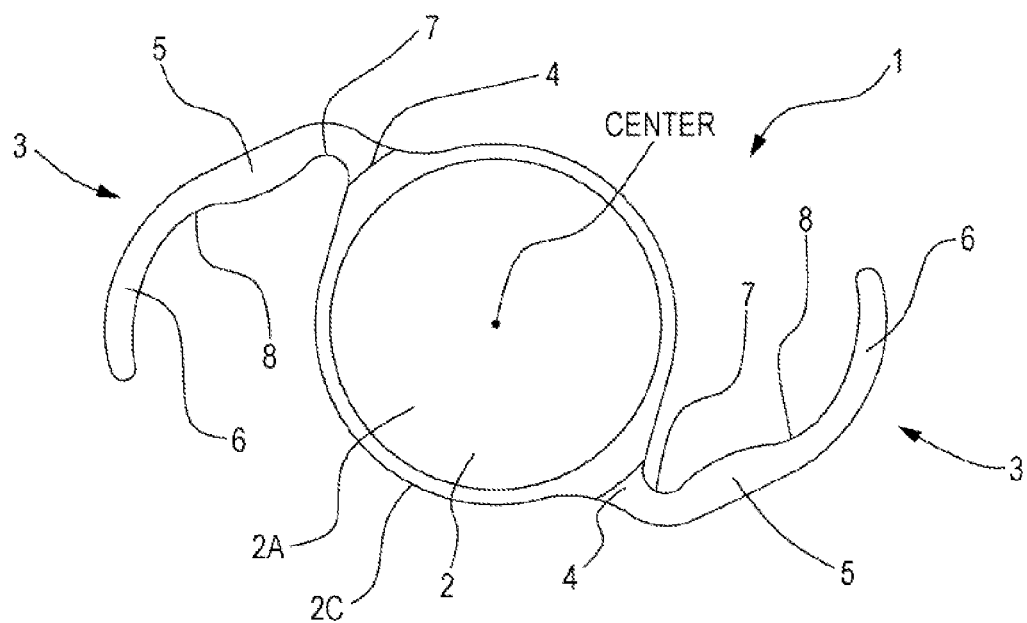
Figure 11B:
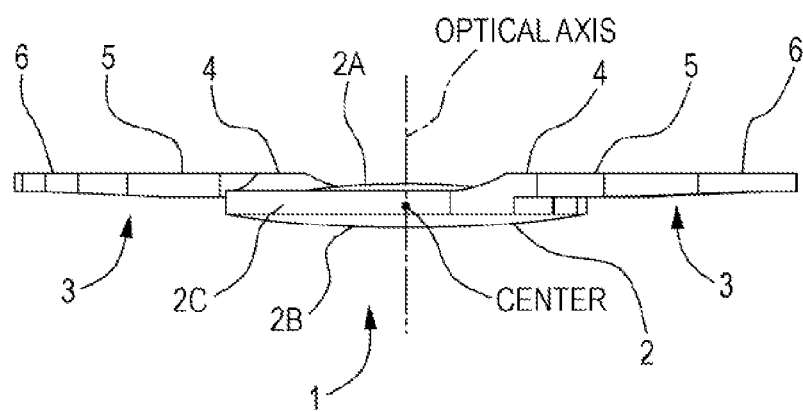

As illustrated in FIGS. 11A and 11B, the intraocular lens 1 of the embodiment includes the optical part 2 and the support part 3. Moreover, the optical part 2 and the support part 3 are integrally molded. The material of the intraocular lens 1 may be a material generally used as a bendable soft intraocular lens, such as a simple substance including HEMA (hydroxy ethyl methacrylate) or a composite material of acrylic ester and methacrylic ester.

The optical part 2 offers a predetermined refractive power to the patient's eye. The support part 3 is formed to support the optical part 2 in the eye. The intraocular lens 1 of the embodiment includes a pair of support parts 3. In the embodiment, when the intraocular lens 1 is installed in the installation part 130, the support part 3 that faces the direction of the nozzle part 182 from the optical part 2 is referred to as the front support part 3A, and the support part 3 that faces the direction of the plunger 300 as the rear support part 3B.

The pair of support parts 3 extends outward from the periphery of the optical part 2. The support part 3 has a loop shape that is curved in the circumferential direction. A distal end of the support part 3 is a free end. A proximal end of each support part 3 (3A, 3B) extends outward from the periphery of the optical part 2. Moreover, the pair of support parts 3 has a shape symmetric with respect to the center of the optical part 2 and extends in the same circumferential direction.

The optical part 2 of the intraocular lens 1 of the embodiment includes the optical surface 2A, an optical surface 2B, and the optical part side surface 2C. In the intraocular lens 1 illustrated in FIGS. 11A and 11B as an example, the optical surface 2A and the optical surface 2B have different refractive powers. The optical surface 2A is caused to face the cornea side in the eye. The optical surface 2B is caused to face the retina side in the eye. The optical part side surface 2C connects the optical surface 2A to the optical surface 2B.

The optical surfaces 2A and 2B of the embodiment are curved surfaces whose center portions bulge outward. Moreover, in the embodiment, a transition slope is formed around the entire outer circumference of the optical surface 2A. The transition slope is provided outside the refractive power region of the optical surface 2A which provides a refractive power.

The transition slope of the optical surface 2A faces the direction of the refractive power region from an end portion of the refractive power region toward the optical part side surface 2C. Therefore, the optical part side surface 2C is thicker than the optical part 2 at a position of the outer edge of the refractive power region of the optical surface 2A in cross section (not illustrated) as viewed from the side of the intraocular lens 1.

The support part 3 includes the root portion 4, a first arm portion 5, a second arm portion 6, a first constricted portion 7, and a second constricted portion 8. The root portion 4 is connected to the optical part side surface 2C. The root portion 4 extends in a direction away from the center of the optical part 2 along a straight line passing the center of the optical part 2. Moreover, the root portion 4 is formed to have a width that is progressively reduced toward its distal end.

The first arm portion 5 is connected to the distal end of the root portion 4. The first arm portion 5 is inclined with respect to a straight line extending sideward from the center of the optical part 2. An inner surface side, which faces the optical part 2, of the first arm portion 5 has a curved shape that is convex in the direction of the optical part 2. Therefore, the narrow first constricted portion 7 is formed at the position where the root portion 4 is connected to the first arm portion 5. In other words, the cross-sectional area of a cross section, which is perpendicular to the extension direction of the support part 3, of the first constricted portion 7 is smaller than the cross-sectional area of a cross section, which is perpendicular to the extension direction of the support part 3, of the portion (the root portion 4) adjacent to the proximal end side of the first constricted portion 7. Furthermore, in the embodiment, the cross-sectional area of the first constricted portion 7 is smaller than the cross-sectional area of a cross section, which is perpendicular to the extension direction of the support part 3, of the portion (the first arm portion 5) adjacent to a distal end side of the first constricted portion 7. In other words, the portion of the first constricted portion 7 is constricted (becomes narrower). The first constricted portion 7 allows the support part 3 to bend largely at a proximal end of the support part 3 in the direction approaching the optical part 2 to have a suitable shape. In other words, the first constricted portion 7 is a constricted portion for bending the support part 3 at a predetermined position in the direction of the optical part 2.

The second arm portion 6 is connected to a distal end of the first arm portion 5. The second arm portion 6 has a loop shape that is increasingly curved in the direction of the optical part 2 toward its distal end. The width of the second arm portion 6 is shorter than that of the first arm portion 5. Therefore, the narrow second constricted portion 8 is formed at an end, in the direction approaching the optical part 2, of the point where the first arm portion 5 is connected to the second arm portion 6. The second constricted portion 8 allows the second arm portion 6 to crawl suitably along the outer edge of the capsule of the patient's eye when the intraocular lens 1 is installed in the capsule of the patient's eye.

The support part 3 of the intraocular lens 1 of the embodiment is formed to become increasingly thinner toward the distal end. Therefore, the intraocular lens 1 can be folded small, so that the inner diameter of the nozzle part 182 can be reduced.

In the intraocular lens insertion device 10 of the embodiment, the intraocular lens 1 is installed in the installation part 130 such that the optical surface 2A faces upward when the intraocular lens 1 is pressed out.

<2. Usage>
<2-1. Manufacture of Intraocular Lens Insertion Device>

The intraocular lens insertion device 10 of the embodiment is manufactured by assembling the top plate part 150, the setting part 170, and the plunger 300 to a base member formed by integrally molding the main body cylindrical part 110, the right and left wall part 140, the holding part 160, and the insertion part 180. Upon the assembly of the intraocular lens insertion device 10, the intraocular lens 1 is held by the holding part 160 to dispose the intraocular lens 1 in the intraocular lens insertion device 10. In other words, in the embodiment, a preset type intraocular lens insertion system is built with the intraocular lens insertion device 10 and the intraocular lens 1 disposed in advance in the intraocular lens insertion device 10. In other words, the intraocular lens insertion system includes the intraocular lens insertion device 10, and the intraocular lens 1 installed in the installation part 130 of the intraocular lens insertion device 10. However, the technique exemplified in the embodiment can be also applied to an intraocular lens insertion device to be shipped without the intraocular lens 1 disposed in advance therein. Moreover, lubrication coating is performed on the inner wall of the cylindrical main body 100.

The intraocular lens insertion device 10 disposed in the intraocular lens 1 is accommodated in a casing, such as a blister pack, obtained by deforming one resin sheet to be uneven. The movement regulating protrusions for regulating the movement of the intraocular lens 1 are assembled to the casing. A flexible sheet that allows gas for sterilization to pass therethrough is affixed to an opening portion of the casing after the intraocular lens insertion device 10 is accommodated in the casing. Accordingly, the casing is sealed. A sterilization treatment is performed on the casing sealed with the flexible sheet. The sterilized casing is transferred to a site of use.

<2-2. Removal from Casing>

At the site of use, a user (for example, an operator or assistant) peels off the flexible sheet, and takes out the intraocular lens insertion device 10 from the casing. The casing accommodates the intraocular lens insertion device 10 such that the setting part 170 is oriented upward (toward the direction of the opening of the casing) (i.e., in an up-side-down state). After taking out the intraocular lens insertion device 10 disposed in the intraocular lens 1 from the casing, the user changes the manner of holding the intraocular lens insertion device 10 to orient the setting part 170 downward.

In the embodiment, when the intraocular lens insertion device 10 is accommodated in the casing, the plunger 300 is at the initial position, and the rear engagement part 113 of the main body 100 is engaged with the front blade part 351 of the plunger 300. When the plunger 300 is at the initial position, the distal end of the plunger 300 is placed slightly closer to the distal end side than the proximal end of the installation part 130.

<2-3. Press-in of Setting Part>

Next, the user presses the proximal end side of the setting part 170 in the direction approaching the extrusion axis A (i.e., upward) from below the setting part 170. The proximal end side of the setting part 170 is pressed in the direction of the extrusion axis A, so that the proximal end side of the setting part 170 rotates in the direction approaching the extrusion axis A with the pivot part 167 (see FIGS. 8A and 8B) on the distal end side of the setting part 170 as a pivot.

The setting part 170 rotates to cancel the regulation of the movement of the intraocular lens 1 by the holding protruding part 166 (see FIGS. 8A and 8B) of the holding part 160. Moreover, the setting part 170 rotates to be in abutment with the intraocular lens 1 held by the holding part 160. Consequently, the setting part 170 causes the intraocular lens 1 to start moving to be onto the extrusion axis A. The user presses the setting part 170 to rotate the setting part 170 up to a rotation angle that allows the proximal end of the setting part 170 to abut against the holding part 160.

As described above, the setting part 170 rotates and presses the intraocular lens 1, and accordingly the intraocular lens 1 is moved onto the extrusion axis A. More specifically, when the setting part 170 rotates, the second contact part 176A and the second contact part 176B (see FIGS. 7, 8A, and 8B) abut against the optical part 2. Even after the second contact part 176A and the second contact part 176B is in abutment with the optical part 2, the setting part 170 continues being pressed in. Hence, the setting part 170 places the optical part 2 substantially on the extrusion axis A.

Moreover, when the setting part 170 rotates, the first contact parts 175A and 175B abut against the rear support part 3B. Moreover, when the setting part 170 rotates, part of the setting part 170 comes into contact (interferes) with the off-axis movement part 177. The off-axis movement part 177 deforms and abuts against the rear support part 3B. The setting part 170 is further pressed in a state where the rear support part 3B is in abutment with the first contact parts 175A and 175B, the second contact parts 176A and 176B, and the off-axis movement part 177. As a result, deformation in a first direction approaching the optical part 2 and deformation in an upward second direction substantially orthogonal to the first direction (i.e., a direction parallel to the optical axis of the optical part 2) occur in the rear support part 3B. The front support part 3A is placed substantially on the extrusion axis A under almost no stress with the movement of the optical part 2 (see FIG. 7). In the embodiment, the off-axis movement part 177 does not complete the tacking of the rear support part 3B. However, the off-axis movement part 177 may be moved until the completion of the tacking of the rear support part 3B.

Figure 13A:
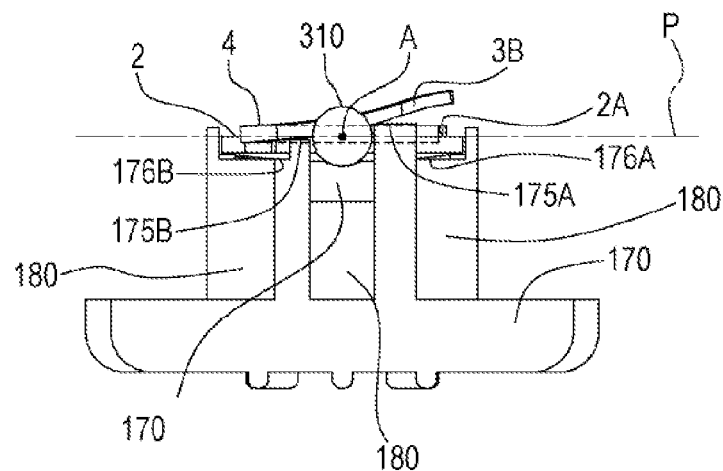
FIGS. 13A and 13B are explanatory schematic views for explaining deformation of a rear support part.
Figure 13B:
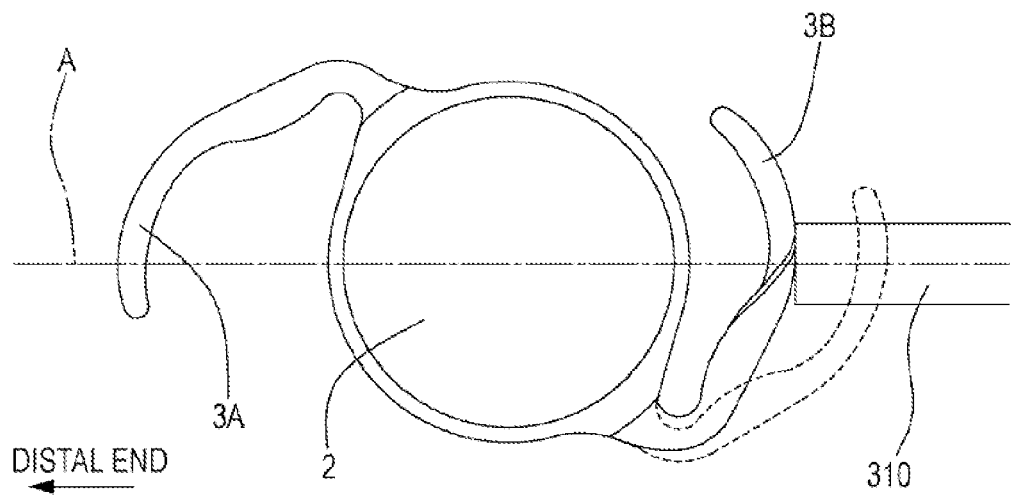

The deformation of the rear support part 3B in the first direction will be described. As illustrated in FIGS. 13A and 13B, when the setting part 170 is pressed in and rotated, the first contact parts 175A and 175B of the setting part 170 abut against the rear support part 3B of the intraocular lens 1 held by the holding part 160. Moreover, the second contact parts 176A and 176B (see FIGS. 7, and 8A and 8B) abut against the optical part 2 of the intraocular lens 1.

As illustrated in FIGS. 8A and 8B, the portions (parts of the upper end portions), which come into contact with the rear support part 3B, of the first contact parts 175A and 175B (only 175A is illustrated in FIGS. 8A and 8B) are higher than the portions (parts of the upper end portions), which come into contact with the optical part 2, of the second contact parts 176A and 176B (only 176B is illustrated in FIGS. 8A and 8B). Therefore, when the proximal end of the setting part 170 abuts against the holding part 160, a first guide part 178A and a second guide part 178B apply stresses to the rear support part 3B and the rear support part 3B becomes bent. In this state, the distal end side of the rear support part 3B is placed above the extrusion axis A as viewed from the side of the extrusion axis A. In other words, as illustrated in FIGS. 13A and 13B, the rear support part 3B is positioned in a state of being displaced upward from the central plane P passing the center of the optical part 2.

Moreover, in the embodiment, a plurality of (two in the embodiment) first contact parts 175 that comes into contact with the rear support part 3B is provided. Therefore, the position of the rear support part 3B is determined more smoothly than a case where one first contact part 175 is provided. Specifically, as illustrated in FIGS. 13A and 13B, the first contact part 175 includes the right first contact part 175A that comes into contact with part of the rear support part 3B, and the first contact part 175B that comes into contact with a portion on the root side of the portion, which comes into contact with the first contact part 175A, of the rear support part 3B. In the right-left direction perpendicular to the extrusion axis A and parallel to the central plane P, one of the first contact parts 175A and 175B is located to the right side of the extrusion axis A and the other is located to the left side of the extrusion axis A. Therefore, the first contact part 175 comes into contact with the rear support part 3B in a more stable state. Furthermore, the distance between the first contact part 175A on the distal end side and the central plane P is longer than the distance between the first contact part 175B on the root side and the central plane P. As a result, when the rear support part 3B is viewed from the proximal end side of the extrusion axis A, the rear support part 3B is inclined and the distal end side of the rear support part 3B is placed above the root portion 4. Therefore, the first contact parts 175A and 175B can bend the rear support part 3B gradually.

Figure 17A:
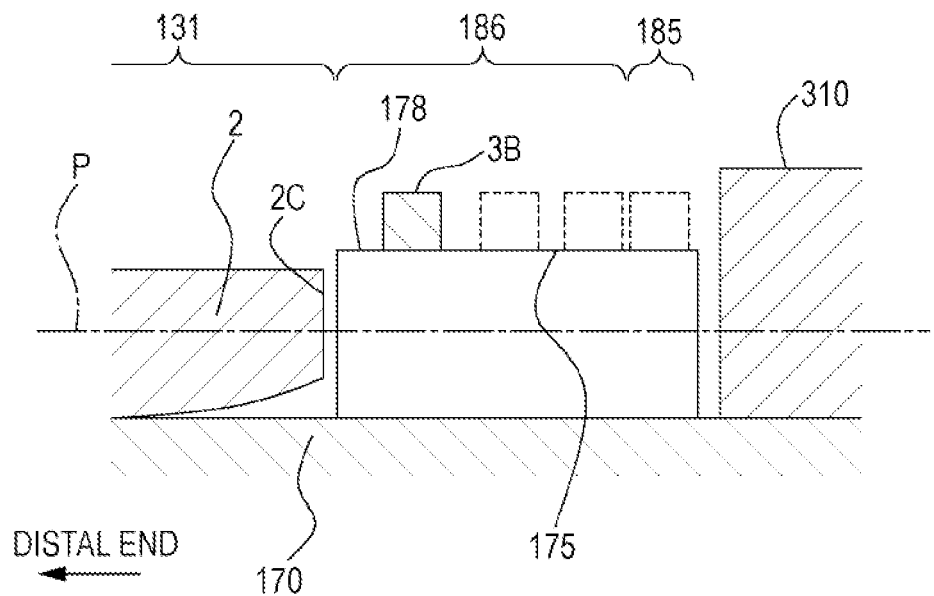
FIGS. 17A and 17B are explanatory schematic views for explaining a movement guide part.
Figure 17B:
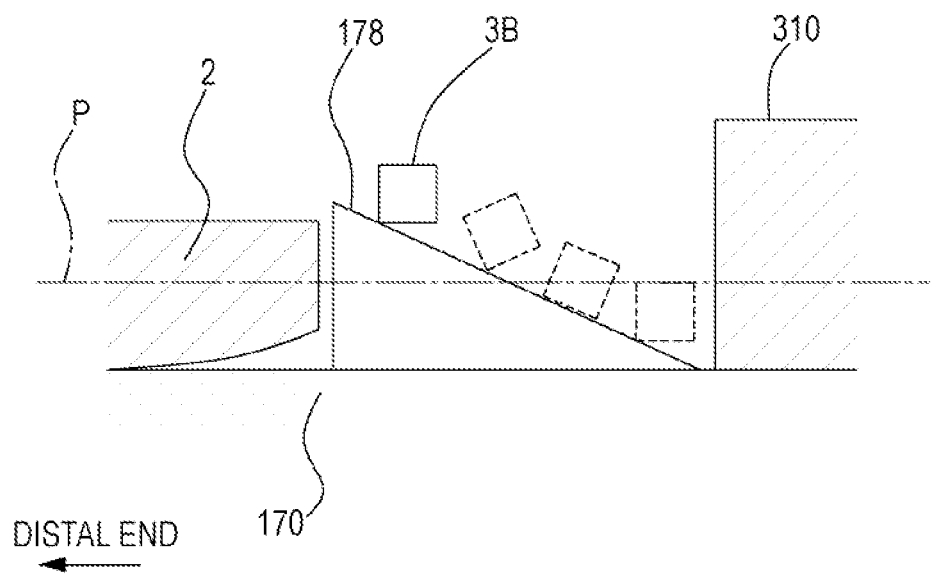

Since the rear support part 3B is bent upward with the application of stress, the rear support part 3B can be suitably bent above the optical part 2. Specifically, as illustrated in FIG. 17B, when the rear support part 3B is gradually bent above the optical part 2 while being brought closer to the optical part 2, unintended deformation may occur in the rear support part 3B due to the stress that brings the rear support part 3B closer to the optical part 2. For example, part of the rear support part 3B may be twisted (see FIG. 13B). Moreover, for example, part of the rear support part 3B may bend toward the proximal end side. Moreover, while the extrusion member 310 presses the rear support part 3B bent upward with the application of stress, the optical part 2 receives downward stress (in a direction away from the central plane P and an opposite direction to the direction to which the rear support part 3B is displaced by positioning parts 185), and is pressed against the second contact part 176. In other words, the rear support part 3B is displaced upward with the application of stress and pressed by the extrusion member 310 in the direction parallel to the extrusion axis A. Consequently, the upward movement (deformation) of the optical part 2 can be prevented. In other words, the possibility that the optical part 2 rises and the rear support part 3B collides with the optical part side surface 2C when the rear support part 3B is bent toward the direction of the optical part 2. Therefore, the rear support part 3B can tack suitably onto the optical surface 2A of the optical part 2.

In the intraocular lens insertion device 10 of the embodiment, while the intraocular lens 1 is held with little stress upon storage, the rear support part 3B is bent upward with the application of stress upon insertion. The distal end side of the rear support part 3B is bent upward from the lower side substantially orthogonal to the direction in which the rear support part 3B extends. Hence, an unintended twist and bending of the rear support part 3B that may occur when the distal end side of the rear support part 3B is lifted up can be made difficult to occur. In the intraocular lens insertion device 10 of the embodiment, as illustrated in FIG. 17A, the rear support part 3B is deformed and moved in the direction approaching the optical part 2 after being displaced upward of the central plane P to tack the rear support part 3B. Therefore, the intraocular lens insertion device 10 can bend the rear support part 3B in a suitable shape toward the direction approaching the optical part 2 while the possibility that such an unintended deformation as illustrated by example in FIG. 13B occurs is reduced.

In the intraocular lens insertion device 10 of the embodiment, the first contact parts 175A and 175B bend the rear support part 3B upward. Instead, the optical part 2 of the intraocular lens 1 under no stress may be bent downward. Moreover, the inclination angle of the optical part 2 with respect to the rear support part 3B may be changed between upon storage and upon insertion to bend the rear support part 3B upward. In the intraocular lens insertion device 10 of the embodiment, the rear support part 3B is bent upward. Instead, the front support part 3A may be bent upward. Needless to say, the direction in which the support part 3 is bent may be not upward but downward. More specifically, in the intraocular lens insertion device 10 of the embodiment, the rear support part 3B is tacked with the positioning parts 185 toward the optical surface 2A side where its center portion is valley-folded. Instead, for example, the rear support part 3B may be tacked with the positioning parts 185 toward the optical surface 2B side that is to be valley-folded. Moreover, the distal end inclined surface 317 of the plunger 300 may be inclined not only rightward but also upward. In this case, stress in the opposite direction to the twisted direction is applied by the distal end inclined surface 317 to the rear support part 3B. As a result, the possibility that unintended deformation occurs in the rear support part 3B is further reduced.

The deformation of the rear support part 3B in the second direction will be described with reference to FIGS. 14A to 14C and 15. The setting part 170 is pressed in the direction of the extrusion axis A and accordingly the off-axis movement part 177 of the setting part 170 abuts against the stress generation part 156 of the top plate part 150. The off-axis movement part 177 is made of an elastic material. The off-axis movement part 177 is deformed by abutting against the stress generation part 156. In other words, the stress generation part 156 comes into contact with the off-axis movement part 177 and accordingly the off-axis movement part 177 deforms and then presses the support part 3 (the rear support part 3B).

Figure 14A:
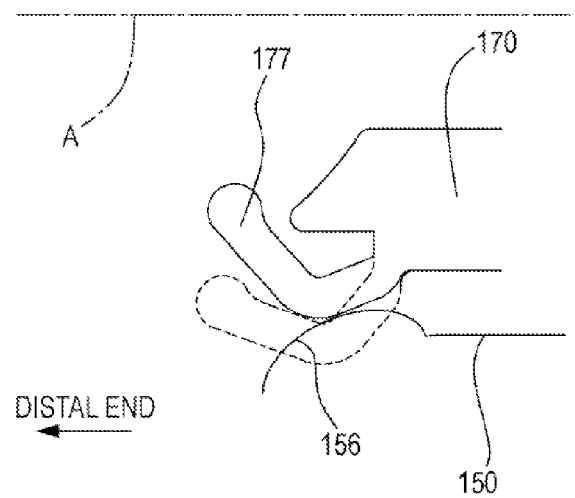
FIGS. 14A to 14C are explanatory schematic views for explaining the deformation of the rear support part by an off-axis movement part.
Figure 14B:
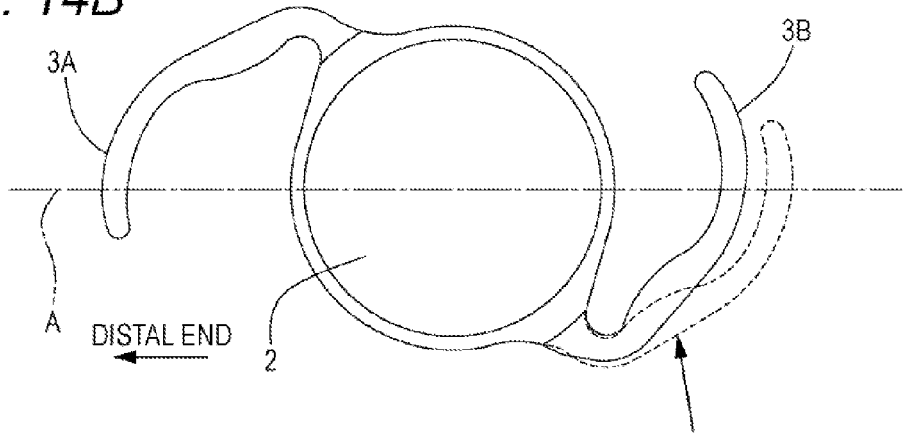
Figure 14C:
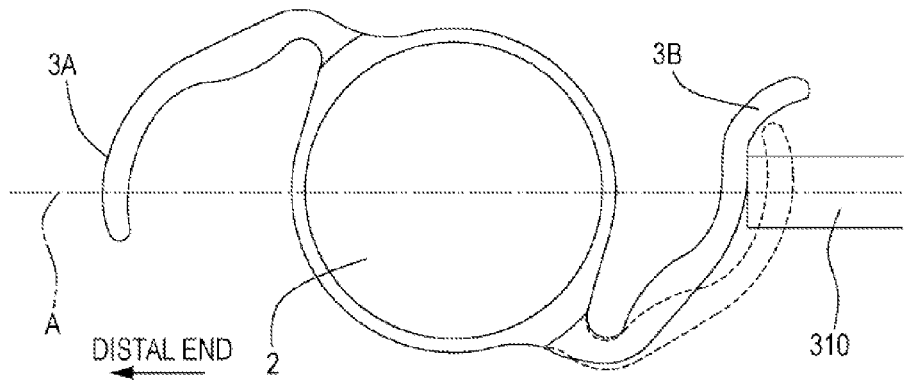
Figure 15:
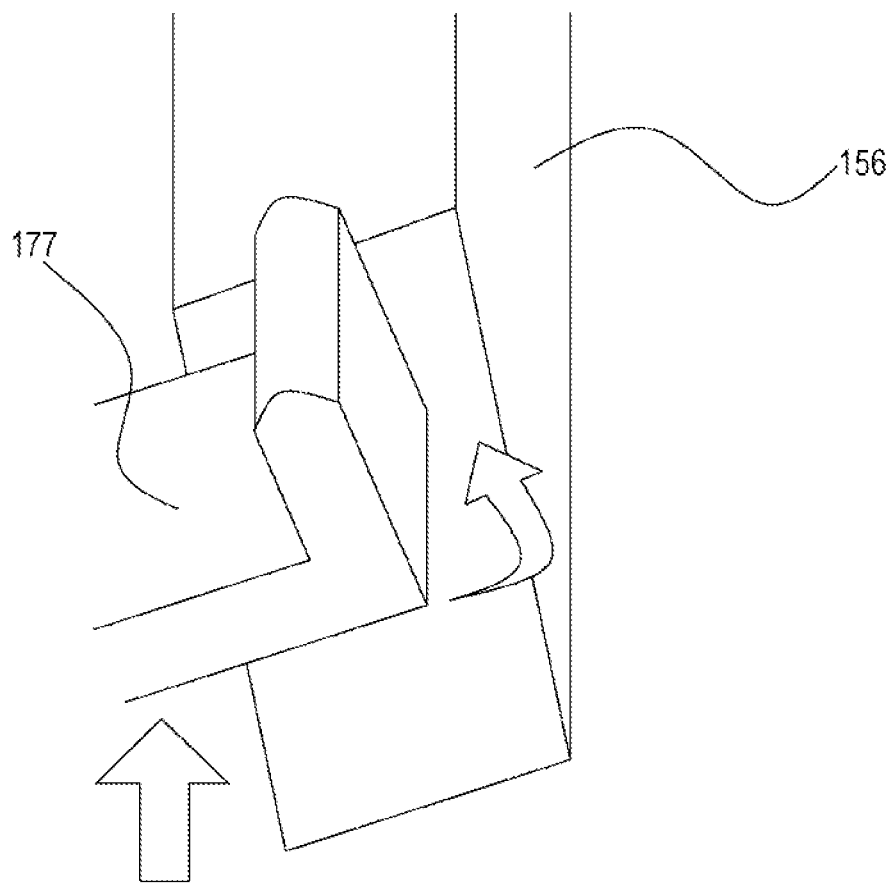
FIG. 15 is an explanatory schematic view for explaining deformation of the off-axis movement part by a stress generation part.

Specifically, as illustrated in FIG. 15, a bottom face of the stress generation part 156 of the embodiment has a tapered shape. The off-axis movement part 177 ascends while sliding over the tapered surface of the stress generation part 156. As a result, the off-axis movement part 177 rotates frontward on the paper of FIG. 15 as the off-axis movement part 177 moves up. In other words, as illustrated in FIG. 14A, when the setting part 170 moves up, the off-axis movement part 177 rotates in the direction approaching the extrusion axis A. Moreover, as illustrated in FIGS. 4 and 7, the intraocular lens 1 in a state where the rear support part 3B is placed in such a manner to be pointed to the proximal end side with respect to the optical part 2 is installed in the installation part 130. The off-axis movement part 177 rotates and accordingly the distal end of the off-axis movement part 177 presses, in a direction intersecting with the extrusion axis A, the side surface of the rear support part 3B of the intraocular lens 1 installed in the installation part 130. Therefore, the rear support part 3B pressed by the off-axis movement part 177 is bent toward the direction approaching the optical part 2 (see FIG. 14B).

Since the side surface of the rear support part 3B is pressed from the direction intersecting with the extrusion axis A as described above, the rear support part 3B can be suitably bent. More specifically, if the rear support part 3B is brought closer to the optical part 2 by simply moving the extrusion member 310 linearly in the direction parallel to the extrusion axis A, the rear support part 3B may be unintentionally deformed due to the stress that brings the rear support part 3B closer to the optical part 2. For example, part of the rear support part 3B may bend toward the proximal end side (see FIG. 14C).

In the intraocular lens insertion device 10 of the embodiment, the rear support part 3B can be pressed from a direction different from the extrusion axis A. Hence, in the intraocular lens insertion device 10, the rear support part 3B can be bent in a suitable shape. Moreover, in the intraocular lens insertion device 10, the intraocular lens 1 is bent by a combination of the off-axis movement part 177 and the extrusion member 310. Hence, in the intraocular lens insertion device 10, the intraocular lens 1 can be folded small and suitably inserted into the patient's eye. In the intraocular lens insertion device 10 of the embodiment, the off-axis movement part 177 presses the rear support part 3B in the direction intersecting with the extrusion axis A. The off-axis movement part 177 may be provided on the front support part 3A side. In this case, the off-axis movement part 177 may bend the front support part 3A toward the direction approaching the optical part 2 by pressing the front support part 3A in a direction different from the extrusion axis A.

As illustrated in FIGS. 7 and 11A, the off-axis movement part 177 of the embodiment abuts against the distal end side, with respect to the first constricted portion 7, of the rear support part 3B and presses the rear support part 3B. Therefore, the off-axis movement part 177 can bend the rear support part 3B suitably with the first constricted portion 7. Moreover, the off-axis movement part 177 of the embodiment abuts against the proximal end side (the root side of the support part 3), with respect to the middle of the total length, of the rear support part 3 and presses the rear support part 3B. Therefore, the off-axis movement part 177 can bend the entire rear support part 3B easily.

The stress generation part 156 of the embodiment is formed of a member different from the off-axis movement part 177. The stress generation part 156 provides the off-axis movement part 177 with stress for allowing the off-axis movement part 177 to press the support part 3 (the rear support part 3B). In other words, the stress generation part 156 uses the stress to move, onto the extrusion axis A, the intraocular lens 1 held by the holding part 160 off the extrusion axis A to come into contact with the off-axis movement part 177 and provide the stress to the off-axis movement part 177. The off-axis movement part 177 deforms due to the provided stress and presses the support part 3 (the rear support part 3B). Therefore, the user does not need to perform an operation for moving only the off-axis movement part 177. Moreover, the off-axis movement part 177 of the embodiment is connected (fixed) to the setting part 170 forming the installation part 130. Therefore, with a simple configuration, the off-axis movement part 177 can be accurately pressed against the support part 3. Moreover, at least part of the portion, which comes into contact with the support part 3, of the off-axis movement part 177 is formed in a curved surface (see FIG. 14A). Therefore, the off-axis movement part 177 can follow the deformation of the support part 3 to come into contact with the support part 3, and bend the support part 3 suitably. The possibility that the support part 3 is, for example, scratched also reduces.

Moreover, in the intraocular lens insertion device 10 of the embodiment, the rear support part 3B is pressed from the side of the rear support part 3B where the root portion 4 is located. Instead, the rear support part 3B may be pressed in the direction intersecting with the extrusion axis A from the side where a distal end of the rear support part 3B is located. Moreover, in the intraocular lens insertion device 10 of the embodiment, the off-axis movement part 177 is provided to the setting part 170 that moves the intraocular lens 1 onto the extrusion axis A. However, the off-axis movement part 177 may be formed to apply, to the support part 3, stress from a direction different from the extrusion axis A by the user operating a different member from the setting part 170.

Moreover, in the intraocular lens insertion device 10 of the embodiment, the rear support part 3B is bent toward the direction approaching the optical part 2 by the combination of the off-axis movement part 177 and the extrusion member 310. Instead, the off-axis movement part 177 may bend the rear support part 3B without using the extrusion member 310.

<2-4. Injection of Viscoelastic Substance>

Next, the user holds an injector, such as a syringe, where a lubricant (viscoelastic substance) is filled. Next, the user inserts an injection needle of the injector into the injection port 154 of the top plate part 150. More specifically, the user brings the injection needle into abutment within the area of the needle guide part 153 (see FIG. 4) formed on the outer wall surface of the top plate part 150. The user moves a distal end of the injection needle in the direction of the injection port 154 while being in abutment with the outer wall surface of the top plate part 150. The width of the area surrounded by the needle guide part 153 is progressively reduced toward the injection port 154. In other words, in the embodiment, the injection port 154 is formed at the inner vertex of the inverted V shape. Therefore, the needle guide part 153 guides the injection needle to the injection port 154. Accordingly, the injection needle is inserted into the injection port 154.

In the intraocular lens insertion device 10 of the embodiment, the movement regulating holes 152 to be penetrated by the movement regulating protrusions (not illustrated) provided to the casing are formed in the outer wall surface of the top plate part 150 (see FIG. 4). The inverted V-shaped needle guide part 153 is formed in such a manner as to intersect with the straight lines linking the injection port 154 to the movement regulating holes 152. Therefore, it is possible to prevent the injection needle from being wrongly inserted into the movement regulating holes 152.

Next, the user discharges the viscoelastic substance or the like that is filled in the injector from the distal end of the injection needle to fill the viscoelastic substance in the intraocular lens insertion device 10. After completing the injection of the viscoelastic substance, the user extracts the injection needle from the intraocular lens insertion device 10.

Figure 16A:
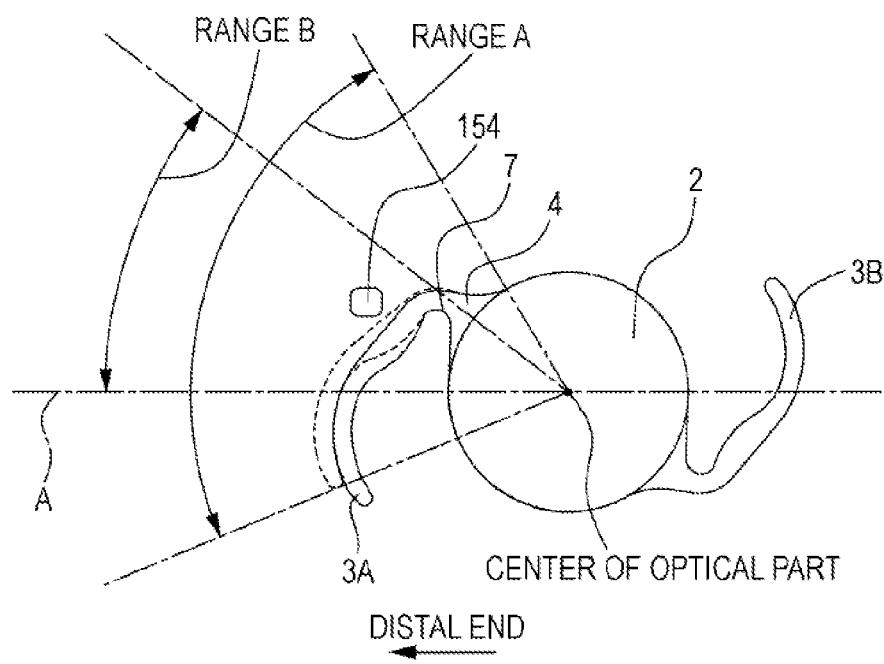
FIGS. 16A and 16B are explanatory schematic views for explaining an insertion port.
Figure 22A:
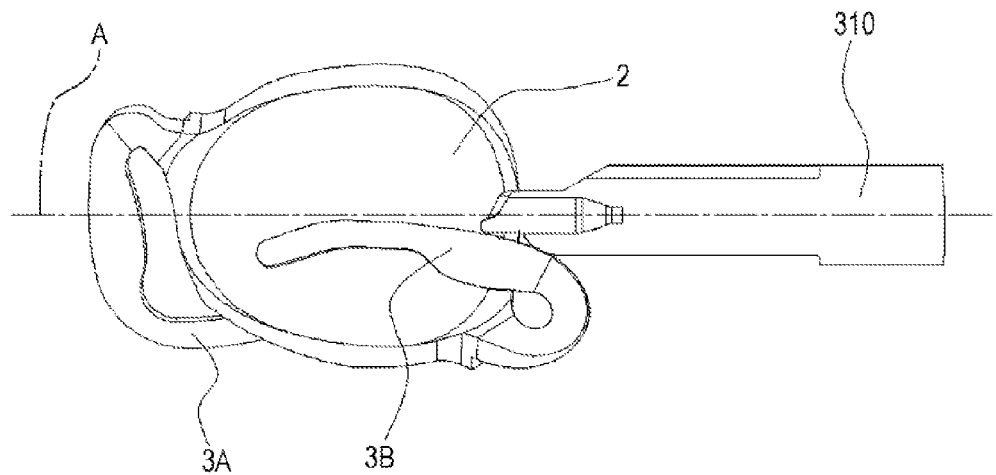
FIGS. 22A and 22B are explanatory schematic views for explaining deformation of a front support part.

As illustrated in FIGS. 4, 5, 16A, and 16B, in the embodiment, the injection port 154 is provided outward of the portion where the outer surface of the front support part 3A is placed (in other words, within a range A of FIG. 16A). As illustrated in FIG. 16A, when the viscoelastic substance is injected from the injection port 154, the front support part 3A is pressed by the injected viscoelastic substance and bent toward the direction approaching the optical part 2 (see a solid line of FIG. 16A). For example, when the injection port 154 is placed directly above the support part 3, the support part 3 is bent downward by the injected viscoelastic substance. As a result, when the intraocular lens 1 is being advanced, it becomes easy for the front support part 3A to enter between the optical surface 2B and the bottom wall, which may lead to a tacking failure in the front support part 3A (see FIG. 22A). In the intraocular lens insertion device 10 of the embodiment, the injection port 154 is provided at the position displaced from directly above the support part 3. Hence, it is possible to suppress downward deformation of the front support part 3A due to the injection of the viscoelastic substance.

Figure 16B:
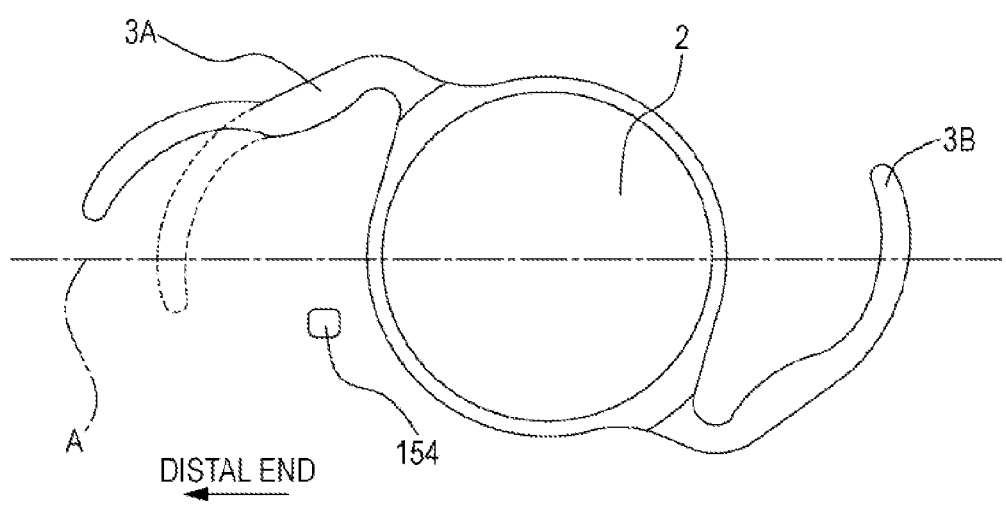

For example, as illustrated in FIG. 16B, if the injection port 154 is provided inward of the front support part 3A, the front support part 3A may be bent toward a direction away from the optical part 2 due to the injected viscoelastic substance. If the intraocular lens 1 is pressed by the extrusion member 310 in the distal end direction while the front support part 3A is bent toward the direction away from the optical part 2, the front support part 3A may be bent toward an unintended direction.

In the intraocular lens insertion device 10 of the embodiment, the front support part 3A can be bent by the viscoelastic substance in a direction in accordance with the shape of the intraocular lens 1 bent upon discharge into the patient's eye. Therefore, the intraocular lens 1 can be suitably bent and discharged into the patient's eye.

Moreover, as illustrated in FIG. 16A, the injection port 154 of the embodiment is provided in a range B surrounded by the straight line passing both the center of the optical part 2 and the proximal end of the front support part 3A, and the extrusion axis A. Therefore, the loop-shaped front support part 3A is pressed by the viscoelastic substance from the proximal end side. Hence, the front support part 3A bends more suitably than a case of being pressed from the distal end side. Moreover, the injection port 154 of the embodiment is located on the distal end side with respect to the optical part 2 installed in the installation part 130. Therefore, while unintended deformation is suppressed from occurring in the front support part 3A, the viscoelastic substance is efficiently filled in an area where the intraocular lens 1 advances.

Moreover, in the embodiment, the injection port 154 is provided to the passage part 132 (see FIG. 7) between the distal end in the extrusion axis A direction of the optical part 2 to be installed and the proximal end of the insertion part 180. Therefore, the viscoelastic substance spreads from the injection port 154, and is efficiently applied onto the optical part 2 having a large volume and to the passage part 132 where the entire intraocular lens 1 slides. Therefore, the intraocular lens 1 can be suitably slid, for example, without using a large amount of expensive viscoelastic substance.

In the intraocular lens insertion device 10 of the embodiment, the injection port 154 is provided outward of the front support part 3A. Instead, the injection port 154 may be provided outward of the rear support part 3B. Alternatively, the intraocular lens insertion device 10 may include a plurality of injection ports 154. The injection ports 154 may be provided outward of both the front support part 3A and the rear support part 3B. In other words, the injection port 154 is simply required to be provided outward of the support part 3. The injection port 154 is provided outward of the support part 3. Accordingly, it is possible to prevent deformation failure in the support part 3 and to bend the support part 3 suitably with stress generated upon the injection of the viscoelastic substance. The viscoelastic substance may be injected before the setting part 170 is pressed in (in a state where the intraocular lens 1 is held by the holding part 160). More specifically, the viscoelastic substance may be injected from the injection port 154 placed outward of the support part 3 of the intraocular lens 1 held by the holding part 160 to bend the support part 3 toward the direction approaching the optical part 2. The setting part 170 may be pressed in afterward to place, on the extrusion axis A, the intraocular lens 1 whose support part 3 has been bent by the viscoelastic substance.

<2-5. Press-in to Standby Position>

The user sets the orientation of the intraocular lens insertion device 10 in such a manner as to point downward the opening of the bevel part 183 (see FIGS. 12A to 12E) and holds the main body cylindrical part 110 at a point, which is slightly closer to the distal end side than the overhanging part 11, with the fingers from the up-down direction. Next, the user presses the pressing part 370 with the finger different from the fingers that are holding the main body cylindrical part 110. Consequently, the plunger 300 is pressed forward from the initial position where the rear engagement part 113 is engaged with the front blade part 351 to the standby position where the front engagement part 112 is engaged with the front blade part 351. At this point in time, as illustrated in FIGS. 13A and 13B, the rear support part 3B is positioned by the first contact parts 175A and 175B at the position displaced from the central plane P of the intraocular lens 1. In other words, as illustrated in FIG. 17A, the portions of the first contact parts 175A and 175B, the portions being in contact with the rear support part 3B immediately before tacking, function as the positioning parts 185 that position the rear support part 3B.

Figure 12A:
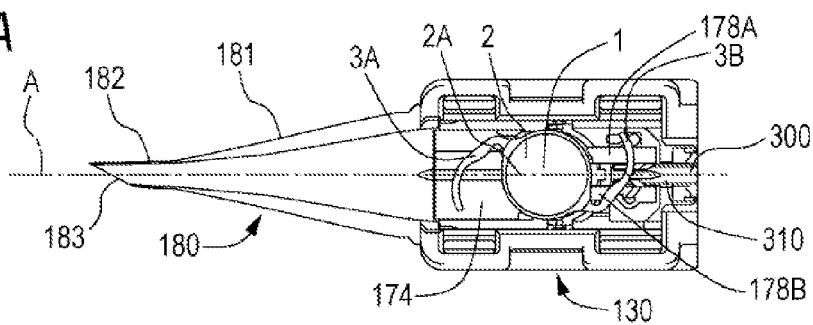
FIGS. 12A to 12E are explanatory schematic views for explaining a deformed state of the intraocular lens upon extrusion.

When the plunger 300 is further pressed from the initial position, the linear movement part 313 of the plunger 300 abuts against the rear support part 3B positioned by the positioning parts 185 (see FIG. 12A). When the plunger 300 is further advanced in the distal end direction, the rear support part 3B slides over the first contact parts 175A and 175B and is bent toward the direction approaching the optical part 2. In other words, as illustrated in FIG. 17A, a portion of each of the first contact parts 175A and 175B between the positioning part 185 and the optical part installation part 131 functions as a movement guide part 186. The two movement guide parts 186 come into contact with the rear support part 3B in the middle of the movement of the rear support part 3B by the linear movement part 313 to guide the movement of the rear support part 3B by the linear movement part 313. The linear movement part 313 deforms and moves the rear support part 3B in the direction approaching the optical part 2. Meanwhile, the movement guide parts 186 abut against the rear support part 3B. Therefore, the movement guide parts 186 prevent or suppress the rear support part 3B from moving from the linear movement part 313 to the optical part contact part 314. In this state, the movement of the optical part 2 in the distal end direction is stopped by the abutment parts 157A and 157B (see FIGS. 5, 6A and 6B).

In the intraocular lens insertion device 10 of the embodiment, the rear support part 3B is positioned at the position displaced from the central plane P passing the center in the thickness direction of the optical part 2 and being perpendicular to the optical axis of the optical part 2. Next, as illustrated in FIG. 17A, the rear support part 3B is slid along surfaces or ridges parallel to the extrusion axis A (the surfaces of the upper ends of the movement guide parts 186 in the embodiment) to bend the rear support part 3B toward the direction approaching the optical part 2. Therefore, the rear support part 3B can be suitably bent toward the direction approaching the optical part 2.

More specifically, for example, if the rear support part 3B is slid on a steep slope, a front side of the rear support part 3B may be caught on the slope and accordingly the rear support part 3B may be twisted (see FIG. 17B). On the other hand, as illustrated in FIG. 17A, the movement guide parts 186 of the embodiment guide the movement of the rear support part 3B while maintaining the distance between the rear support part 3B and the central plane P constant. In other words, in the intraocular lens insertion device 10 of the embodiment, the movement guide parts 186 where the surface or ridge parallel to the extrusion axis A is formed slide the rear support part 3B. Hence, a twist of the rear support part 3B can be prevented.

The movement guide parts 186 may guide the movement of the rear support part 3B in such a manner as that the rear support part 3B approaches the central plane P as the rear support part 3B approaches the optical part installation part 131. For example, the parallel surface or ridge forming the movement guide part 186 may be inclined with respect to the extrusion axis A. Moreover, the movement guide part 186 may be formed into a staircase that descends stepwise toward the distal end direction. Moreover, the expression of "maintaining the distance between the rear support part 3B and the central plane P constant" does not simply indicate that the rear support part 3B moves strictly parallel to the central plane P. In other words, the surface or ridge of the movement guide part 186 may be formed in such a manner as that the rear support part 3B rises slightly (in other words, moves gradually away from the central plane P) as the rear support part 3B approaches the optical part installation part 131. In this case, the climb gradient (the angle with respect to the extrusion axis A) of the surface or ridge of the movement guide part 186 is set to eight degrees or less and accordingly the occurrence of such a twist as illustrated by example in FIG. 17B can be reduced, which was confirmed by the inventor in an experiment. A distal end of the movement guide part 186 is simply required to be provided at a position higher than the height of the end portion on the proximal end side of the optical part 2.

The surface of the movement guide part 186 may be a curved surface. The ridge may be a curve. Moreover, the movement guide part 186 having the flat or curved surface may be inclined in the horizontal direction as viewed from the direction of the extrusion axis A. Moreover, the intraocular lens insertion device 10 of the embodiment includes a plurality of movement guide parts 186 (a first movement guide part 186 formed on the upper surface of the right first contact part 175A, and a second movement guide part 186 formed on the upper surface of the left first contact part 175B).

The left second movement guide part 186 comes into contact with a portion of the rear support part 3B, the portion being closer to the root side than the portion that comes into contact with the right first movement guide part 186. Therefore, the guidance of the rear support part 3B is further stabilized. Furthermore, as illustrated in FIG. 7, the right first movement guide part 186 (the upper surface of the first contact part 175A) is located on the right side of the extrusion axis A. On the other hand, the left second movement guide part 186 (the upper surface of the first contact part 175B) is located on the left side of the extrusion axis A. Therefore, in the intraocular lens insertion device 10 of the embodiment, tacking can be made by pressing out the rear support part 3B from the right and left sides of the extrusion axis A. Accordingly, the tacking is further stabilized. Moreover, as illustrated in FIGS. 13A and 13B, the distance between the right first movement guide part 186 and the central plane P is longer than the distance between the left first movement guide part 186 and the central plane P. Therefore, the first and second movement guide parts 186 of the embodiment can guide deformation and movement upon tacking with the rear support part 3B bent gradually. In the embodiment, the two movement guide parts 186 are used. However, the number of movement guide parts 186 may be one, or three or more.

In the intraocular lens insertion device 10 of the embodiment, the intraocular lens 1 is stored off the extrusion axis A without applying stress to the support part 3. Furthermore, the intraocular lens 1 is placed on the extrusion axis A in a state where the support part 3 is under stress, and then is pressed toward the distal end direction of the extrusion axis A. Instead, stress may be applied to the support part 3 to store the intraocular lens 1. The support part 3, to which stress has been applied and which is stored in the deformed state, is not immediately restored from the deformed state even if the stress is released. For example, for a short time (for example, 20 minutes) after the stress is released, the support part 3 maintains the deformed state. Therefore, if the intraocular lens 1 is stored with the support part 3 under stress, the intraocular lens 1 may be placed at an insertion start position on the extrusion axis A while the support part 3 maintains the deformed state, and the intraocular lens 1 (the support part 3 and the optical part 2) may be pressed out by the extrusion member 310. In other words, the holding part 160 may include the positioning parts 185 that displace and position the rear support part 3B.

Moreover, in the intraocular lens insertion device 10 of the embodiment, the setting part 170 is rotated to form the positioning parts 185 in the installation part 130. Instead, the intraocular lens insertion device 10 may be configured including the positioning parts 185 regardless of the rotation of the setting part 170. For example, the installation part 130 of a non-preset type intraocular lens insertion device may include the positioning parts 185. In this case, for example, when the user loads (installs) the intraocular lens 1 in the installation part 130, the positioning parts 185 provided to the installation part 130 deforms the support part 3.

When the user advances the plunger 300 further in the distal end direction, the rear support part 3B pops out of the distal ends of the first contact parts 175A and 175B to the direction approaching the optical part 2 (the distal end side). The rear support part 3B is bent by the linear movement part 313 toward the direction approaching the optical part 2.

In the intraocular lens insertion device 10 of the embodiment, the distal ends of the first contact parts 175A and 175B (in other words, the distal ends of the two movement guide parts 186) are adjacent to the optical part installation part 131. Therefore, more than a half of the total length of the rear support part 3B is placed above the optical part 2 in the state where the rear support part 3B has popped out of the distal ends of the first contact parts 175A and 175B. The intraocular lens 1 of the embodiment includes the first constricted portion 7. Hence, the rear support part 3B can be bent largely and easily with the position of the first constricted portion 7 as a pivot.

Figure 12B:
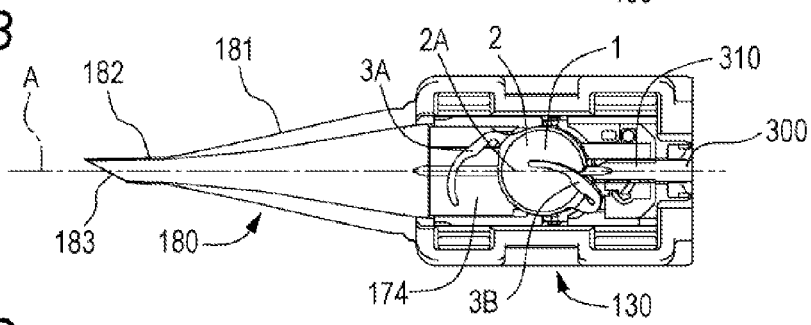

When the plunger 300 is still pressed forward, the optical part contact part 314 of the extrusion member 310 abuts against the optical part side surface 2C of the optical part 2 (see FIGS. 11A and 11B). As illustrated in FIGS. 10A to 10E, the extrusion member 310 of the embodiment includes the linear movement part 313 that presses the rear support part 3B toward the distal end side, and the optical part contact part 314 that presses the optical part 2 toward the distal end side. Therefore, the user can easily perform both appropriate tacking of the rear support part 3B and extrusion of the intraocular lens 1 by simply pressing the extrusion member 310 toward the distal end side. Moreover, in the intraocular lens insertion device 10 of the embodiment, the linear movement part 313 is placed closer to the distal end side than the optical part contact part 314. Hence, it is possible to press the rear support part 3B toward the distal end direction of the extrusion axis A on the distal end side with respect to the end portion on the proximal end side of the optical part 2. Therefore, as illustrated in FIG. 12B, the rear support part 3B can be further bent toward the distal end direction than immediately after popping out of the first contact parts 175A and 175B toward the distal end side. In other words, the distal end of the rear support part 3B is bent toward the distal end direction of the extrusion axis A.

Moreover, the distal end of the linear movement part 313 is provided closer to the distal end side than the distal end of the optical part contact part 314. Accordingly, the distal end of the rear support part 3B can be further extended in the distal end direction. In other words, when the intraocular lens insertion device 10 is viewed from above, more of the rear support parts 3B can be placed above the optical surface 2A of the optical part 2. More of the rear support parts 3B are placed above the optical surface 2A to reduce the size of a portion of the support part 3, the portion lying off the optical part 2 when the optical part 2 is folded. As a result, deformation failure of the intraocular lens 1 during extrusion is reduced. Furthermore, also when the intraocular lens 1 is ejected into the patient's eye, unintended behavior of the support part 3 that restores in the capsule of the patient's eye can be suppressed.

Figure 18A:
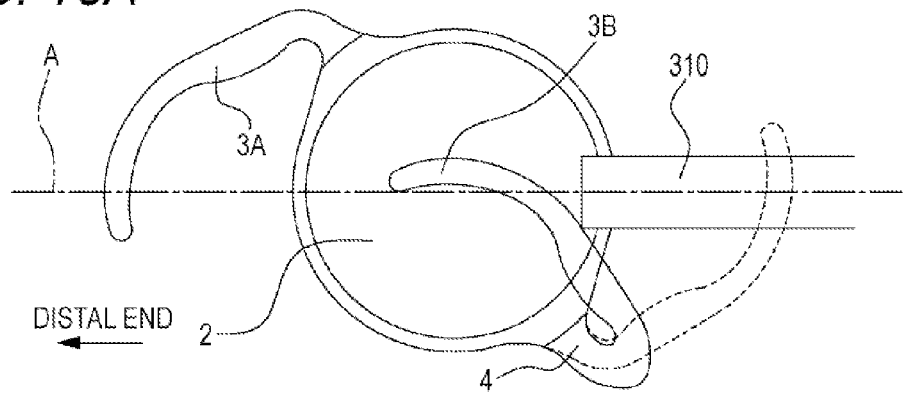
FIGS. 18A to 18C are explanatory schematic views for explaining a deformation suppression part.

As illustrated in FIG. 6B, the intraocular lens insertion device 10 of the embodiment includes the deformation suppression part (the sideward deformation suppression part 149 and the upward deformation suppression part 159) to suppress deformation of part of the rear support part 3B. The deformation suppression part (the sideward deformation suppression part 149 and the upward deformation suppression part 159) suppresses deformation of at least part of the support part 3 of the intraocular lens 1 to be deformed by the movement part 301. As a result, the rear support part 3B is bent in a suitable shape. If the deformation suppression part is not included, part of the rear support part 3B may deform in a direction different from the direction approaching the optical part 2, when the extrusion member 310 presses out the support part 3B. For example, as illustrated in FIG. 18A, the root portion 4 of the rear support part 3B of the intraocular lens 1 may deform in a direction moving away from the extrusion axis A (in other words, a direction away from the linear movement part 313 in the embodiment).

In the intraocular lens insertion device 10 of the embodiment, the optical part 2 is deformed in the insertion part 180 in such a manner as to hug the rear support part 3B. Unless the rear support part 3B is suitably bent toward the direction approaching the optical part 2, when the optical part 2 is folded small in the insertion part 180, a large part of the rear support part 3B may lie off the end of the optical part 2 folded small. If the intraocular lens 1 is pressed out with a large part of the rear support part 3B lying off the optical part 2, the rear support part 3B may be restored in an unintended direction in the patient's eye. In this case, the operator may adjust the orientation of the intraocular lens 1.

Figure 18B:
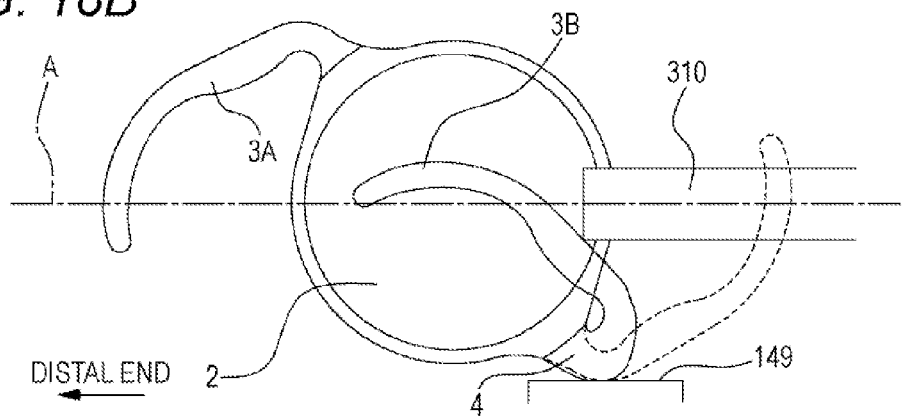
Figure 18C:
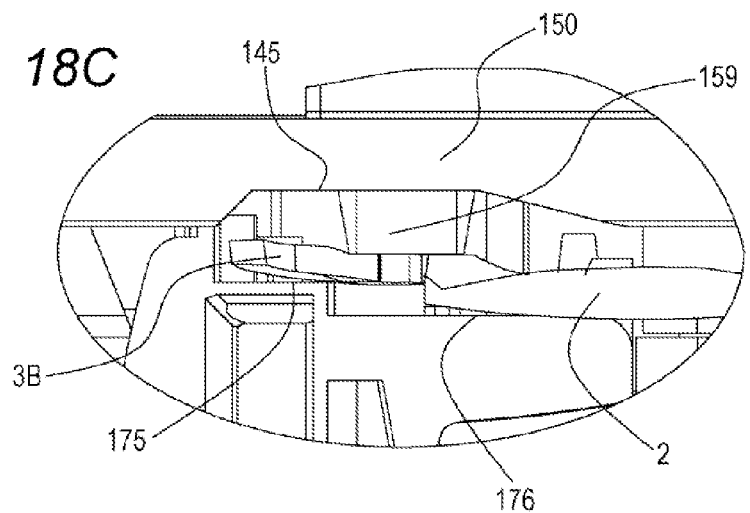

As illustrated in FIG. 18B, in the intraocular lens insertion device 10 of the embodiment, the sideward deformation suppression part 149 is placed on the side of the root portion 4 of the rear support part 3B (in other words, the position facing the side surface side of the intraocular lens 1). The sideward deformation suppression part 149 suppresses deformation of the root portion 4 of the rear support part 3B in a direction away from the extrusion axis A. The sideward deformation suppression part 149 comes into contact with the first constricted portion 7 (see FIGS. 11A and 11B) of the rear support part 3B. Consequently, the deformation direction at the proximal end of the rear support part 3B is restricted to bend the rear support part 3B suitably. In other words, the sideward deformation suppression part 149 being part of the deformation suppression part comes into contact with the proximal end of the support part 3 to restrict the deformation direction of the support part 3 at the proximal end. Moreover, as illustrated in FIG. 18C, the upward deformation suppression part 159 is placed above the root portion 4 of the rear support part 3B (in other words, at the position facing at least one of the front surface side and the rear surface side of the intraocular lens 1). The upward deformation suppression part 159 suppresses deformation of the rear support part 3B toward above the root portion 4 (the proximal end) (a direction away from the central plane P). Therefore, the distal end of the rear support part 3B can be suitably bent toward the distal end direction of the extrusion axis A.

When the user presses the plunger 300 still further, the optical part 2 escapes from the stop of the movement in the distal end direction by the abutment parts 157A and 157B (see FIGS. 5, 6A and 6B). At this time, the optical part 2 advances under different stresses between the left side and the right side given by the two abutment parts 157A and 157B. More specifically, the intraocular lens 1 passes through the abutment parts 157A and 157B while the side, where the proximal end (the root portion 4) of the rear support part 3B is placed, of the intraocular lens 1 is placed is under larger stress.

Restoring stress by the rear support part 3B is applied to the intraocular lens 1 whose rear support part 3B is bent above the optical part 2. Therefore, as illustrated by example in FIG. 19A, the intraocular lens 1 may be bent toward a restoring direction (the proximal end side of the support part 3) due to the restoring stress of the rear support part 3B when the intraocular lens 1 passes through a narrower point than the width of the optical part 2. In this case, the intraocular lens 1 may be sandwiched between the extrusion member 310 and the left wall of the right and left wall part 140.

The intraocular lens insertion device 10 of the embodiment includes the two abutment parts 157A and 157B that abut against different points on the side surface of the optical part 2 respectively at the right and left positions of the passage part 132 which are away from the extrusion axis A (see FIG. 7). The stresses given by the two abutment parts 157A and 157B from the right and left directions to the intraocular lens 1 moving toward the distal end side are different between the right and left sides of the intraocular lens 1. Specifically, in the embodiment, the two abutment parts 157A and 157B are provided such that the stress from the left side where the root portion 4 of the bent rear support part 3B is located is larger than the stress from the right side. Therefore, the power in the opposite direction to the restoring rotation direction by the rear support part 3B is added to the intraocular lens 1. Hence, it is possible to prevent failure in which the intraocular lens 1 deforms largely in the middle of or immediately after the passage of the abutment parts 157A and 157B.

As illustrated in FIG. 6B, the two abutment parts 157A and 157B each include the slope 144 facing the proximal end direction. As illustrated in FIG. 19B, when the intraocular lens insertion device 10 is viewed from above, a distance LB of the slope of the left abutment part 157B between the distal end portion and the extrusion axis A is shorter than a distance LA of the slope of the right abutment part 157A between the distal end portion and the extrusion axis A. Consequently, with a simple configuration, it is possible to make a difference between stresses to be added to the intraocular lens 1 from the two abutment parts 157A and 157B.

Figure 20A:
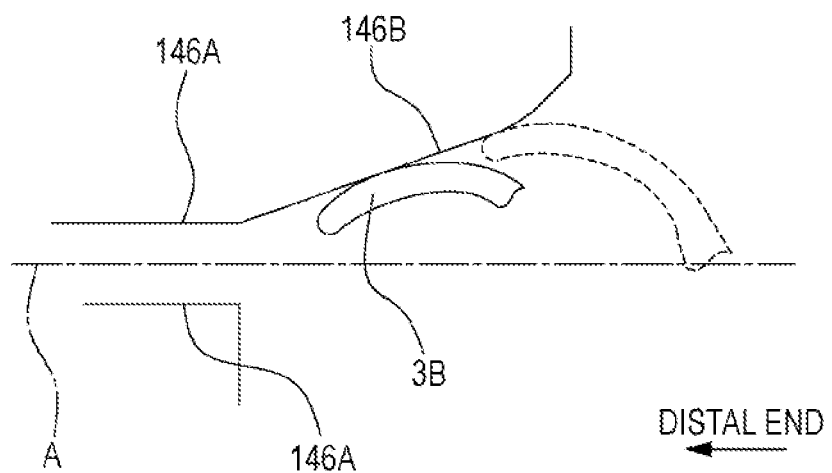
FIGS. 20A and 20B are explanatory schematic views for explaining a deformation guide part.

When the plunger 300 is pressed further forward, the intraocular lens 1 moves through the passage part 132 in the distal end direction. As illustrated in FIG. 20A, when the intraocular lens 1 moves in the distal end direction, the outer surface of the tacked rear support part 3B abuts against the inclined guide surface 146B formed on the inner surface of the top plate part 150 (see FIGS. 6A and 6B) (see a dotted line of FIG. 20A). When the plunger 300 is pressed while the outer surface of the rear support part 3B is in abutment with the inclined guide surface 146B, the rear support part 3B is bent toward the direction of the extrusion axis A by the slope of the inclined guide surface 146B that is inclined toward the proximal end direction (see a solid line of FIG. 20A).

When the plunger 300 is advanced further, the distal end of the rear support part 3B bent toward the direction of the extrusion axis A abuts against the parallel guide surfaces 146A. The parallel guide surfaces 146A provided on the right and left sides of the extrusion axis (center axis) A prevent the distal end of the rear support part 3B from being displaced leftward or rightward. As a result, while the deformed state of the rear support part 3B having the distal end pointed toward the distal end direction (the front-back direction) is maintained, the intraocular lens 1 moves in the distal end direction. As illustrated in FIG. 6B, the deformation guide part 146 of the embodiment is formed on an inner wall on the side facing the optical surface of the optical part 2 of the intraocular lens 1. Therefore, the deformation guide part 146 can appropriately guide the movement of the rear support part 3B, which is made in a state of being laid over the optical part 2.

The intraocular lens insertion device 10 of the embodiment can extrude the tacked rear support part 3B with the deformation guide part 146 (the inclined guide surface 146B and the parallel guide surfaces 146A) while maintaining the rear support part 3B in a suitable shape. More specifically, the inclined guide surface 146B and the parallel guide surfaces 146A can point the distal end of the rear support part 3B suitably toward the distal end direction.

Figure 20B:
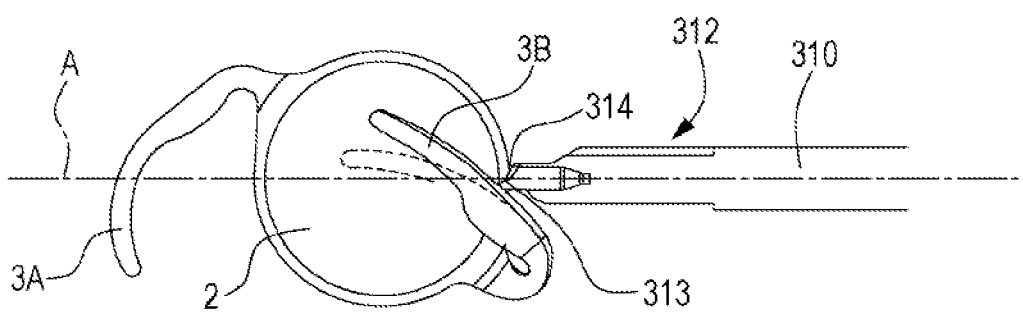

For example, as in a solid line of FIG. 201B, if the distal end of the rear support part 3B is not appropriately pointed toward the direction of the extrusion axis A (the distal end of the rear support part 3B is largely displaced from the direction of the extrusion axis A), there are possibilities that the distal end of the rear support part 3B bends toward the proximal end direction and that the rear support part 3B shifts off from above the optical part 2, due to the viscoelastic substance during the advance. The intraocular lens insertion device 10 of the embodiment bends the distal end of the rear support part 3B toward the distal end direction of the extrusion axis A with the inclined guide surface 146B and the parallel guide surfaces 146A as in a dotted line of FIG. 20B. Hence, the intraocular lens insertion device 10 can extrude the rear support part 3B while maintaining the suitable shape. The deformation guide part 146 may include only one of the inclined guide surface 146B and the parallel guide surface 146A. The intraocular lens insertion device 10 of the embodiment includes the deformation guide part 146 to bend the rear support part 3B suitably. Instead, the intraocular lens insertion device 10 may be provided with the deformation guide part 146 to bring the front support part 3A close to the optical part 2.

Figure 21A:
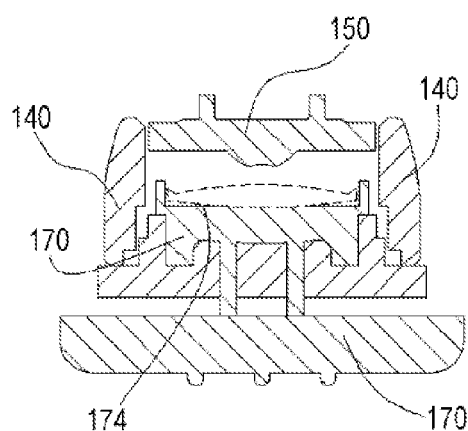
FIG. 21A is a cross-sectional view taken along line XII-XII in FIG. 8A.
Figure 21B:
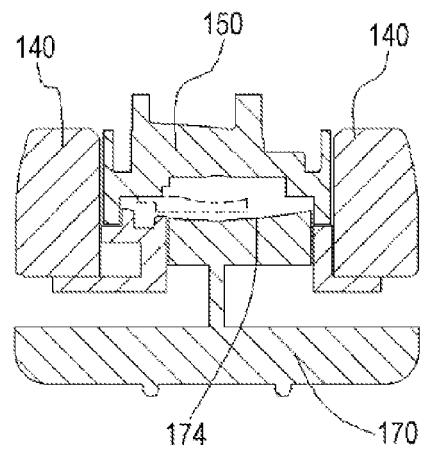
FIG. 21B is a cross-sectional view taken along line XIII-XII in FIG. 8A.
Figure 21C:
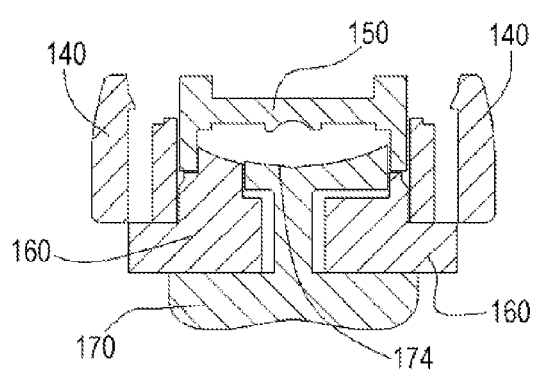
FIG. 21C is a cross-sectional view taken along line XIV-XIV in FIG. 8A.
Figure 21D:
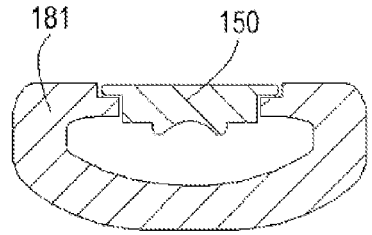
FIG. 21D is a cross-sectional view taken along line XV-XV in FIG. 8A.
Figure 21E:
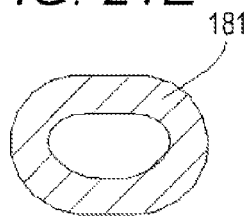
FIG. 21E is a cross-sectional view taken along line XVI-XVI in FIG. 8A.
Figure 21F:
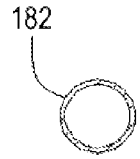
FIG. 21F is a cross-sectional view taken along line XVII-XVII in FIG. 8A.

The user presses the plunger 300 still further, and moves the intraocular lens 1 to the passage part 132. The distorted part 174 is provided to the bottom face of the passage part 132. In the embodiment, the distorted part 174 is distorted having a downward concave shape. FIGS. 21A to 21F illustrate cross-sectional views of the intraocular lens insertion device 10 in the direction perpendicular to the extrusion axis A. FIG. 21A is a cross-sectional view of the distal end portion of the optical part installation part 131 (see FIG. 7). FIGS. 21B, 21C, 21D, 21E, and 21F are cross-sectional views created by displacing the cross-sectional position gradually from the position of FIG. 21A toward the distal end side. As illustrated in FIGS. 21A to 21F, the distortion (curvature) the distorted part 174 is progressively increased toward the distal end. Therefore, the optical part 2 is deformed by the surface tension of the viscoelastic substance in a shape along the distortion of the surface of the distorted part 174. Moreover, as the intraocular lens 1 advances in the distal end direction, the amount of deformation of the optical part 2 increases. As illustrated in FIG. 21A, the bottom passage wall of the proximal end portion of the passage part 132 (in other words, the distal end portion of the optical part installation part 131) is formed flat. Therefore, the unbent optical part 2 supported by the optical part installation part 131 is gradually bent as moving over the distorted part 174 toward the distal end side. Moreover, as illustrated in FIG. 7, when the optical part 2 is installed in the optical part installation part 131, the front support part 3A is placed in the passage part 132 where the distorted part 174 is formed. Therefore, the passage part 132 of the embodiment has both functions of bending the optical part 2 with the distorted part 174, and of storing the front support part 3A before being tacked. Hence, the passage part 132 has a simple configuration. Moreover, the injection port 154 (see FIG. 4) for injecting the viscoelastic substance is provided to the passage part 132. Therefore, the intraocular lens 1 passes smoothly through the passage part 132 having the distorted part 174. Furthermore, a possibility that the surface tension is weakened due to lack of the viscoelastic substance is also reduced.

Figure 12C:
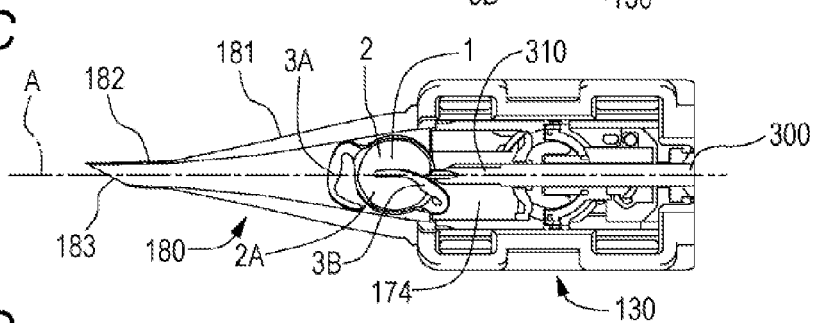

As illustrated in FIG. 12C, when the plunger 300 is pressed further, the distal end side of the intraocular lens 1 enters the tapered part 181. The proximal end of the tapered part 181 is smoothly connected to the passage part 132. Therefore, the intraocular lens 1 moves smoothly to the tapered part 181. When the plunger 300 is pressed further, the distal end of the front support part 3A abuts against the inner wall of the tapered part 181. When the plunger 300 is pressed further, the front support part 3A is bent toward the direction approaching the optical part 2 (toward the proximal end side). At this point in time, the optical part 2 is deformed along the distorted shape smoothly continuous from the passage part 132.

Figure 22B:
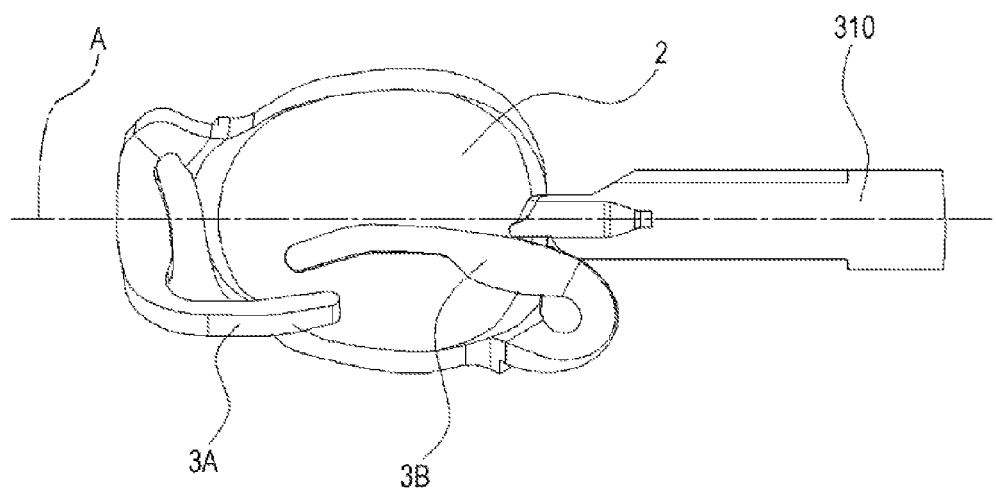

When the plunger 300 is pressed further, the distal end of the front support part 3A runs up onto the optical part 2. The right and left end portions of the optical part 2 start being deformed upward by the inner wall of the taper. The intraocular lens insertion device 10 of the embodiment bends the optical part 2 along the shape of the distorted part 174 by making the distorted part 174 deformed. Furthermore, since the distorted part 174 and the tapered part 181 are smoothly connected, it is possible to prevent the entry of the front support part 3A between the optical part 2 and the inner wall of the main body 100 (see FIG. 22A). As a result, the front support part 3A can be suitably placed on the optical part 2 (see FIG. 22B).

<2-6. Standby Position>

Figure 12D:
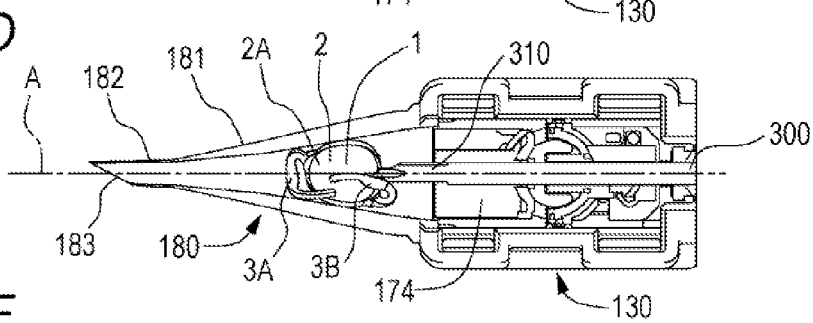
Figure 12E:
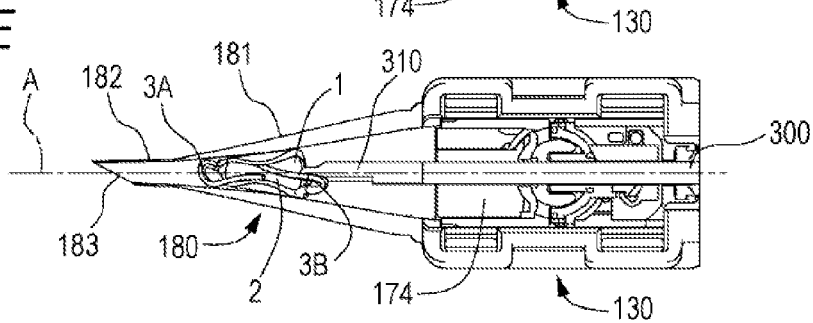

When the plunger 300 is advanced further, the front engagement part 112 (see FIG. 2) of the main body 100 is engaged with the front blade part 351 (see FIG. 9) of the plunger 300. Consequently, the plunger 300 reaches the standby position. At this point in time, as illustrated in FIG. 12D, the distal end of the intraocular lens 1 has reached almost immediately before the nozzle part 182, and more of the front support part 3A is placed above the optical part 2. Moreover, the right and left end portions of the intraocular lens 1 are rolled up toward the direction of the center of the optical part 2.

<2-7. Insertion into Incision>

When the intraocular lens insertion device 10 is put in the standby state, the user inserts the nozzle part 182 into an incision provided in the cornea of the patient's eye. Next, the user turns the intraocular lens insertion device 10 in the circumferential direction of the extrusion axis A in such a manner as to point the direction of the opening of the bevel part 183 toward the crystalline lens capsule of the patient's eye. Next, the user advances the entire intraocular lens insertion device 10 in the direction of the crystalline lens capsule. The user stops the insertion of the intraocular lens insertion device 10 when it enters a state where the opening of the bevel part 183 faces the crystalline lens capsule at a position slightly closer to the cornea side than the crystalline lens capsule.

<2-8. Ejection of Intraocular Lens>

Next, the user resumes the press of the plunger 300 at the standby position. When the plunger 300 is pressed forward from the standby position, the right and left end portions of the optical part 2 are further rolled up. The optical part 2 is rolled up until the area of a transverse section of the optical part 2 becomes substantially equal to the diameter of the opening of the nozzle part 182 (see FIG. 12E). When the plunger 300 is further advanced, the intraocular lens 1 folded small passes through the nozzle part 182.

The user continues the press of the plunger 300 up to the position where the inclined surface 353 (see FIG. 9) of the plunger 300 abuts against the front inclined part 114 (see FIGS. 3A and 3B) of the main body 100. When the distal end of the plunger 300 reaches the proximal end of the nozzle part 182, the rear blade part 352 (see FIG. 9) of the plunger 300 abuts against the proximal end of the main body 100. As the plunger 300 advances, sliding resistance increases.

When the plunger 300 continues being pressed forward, and the intraocular lens 1 starts exposing itself from the distal end of the nozzle part 182, the intraocular lens 1 starts spilling out in the direction where the bevel part 183 faces. When the plunger 300 advances further, the intraocular lens 1 is gradually restored while the root portion 4 of the rear support part 3B is sandwiched between the inner wall of the nozzle part 182 and the plunger 300.

More specifically, the intraocular lens 1 is gradually restored while the root portion 4 of the rear support part 3B is sandwiched between the inner wall of the nozzle part 182 and the left depressed part 319 of the plunger 300 facing downward. Therefore, the optical part 2 is restored in such a manner as to spread onto a plane parallel to the right and left planes orthogonal to the opening of the bevel part 183 facing downward. In other words, the intraocular lens 1 is gradually restored from the state of being disposed in the installation part 130 to a state of being rotated approximately 90° with respect to the extrusion axis A. In other words, the intraocular lens 1 is gradually restored in such a manner as that the optical axis of the optical part 2 of the intraocular lens 1 coincides with the visual axis (the line connecting the retina to the cornea) of the patient's eye. Moreover, upon the restoration, the optical surface 2A faces the cornea side of the patient's eye.

When the plunger 300 is advanced further, substantially the entire left depressed part 319 is exposed from the nozzle part 182. Consequently, the holding of the root portion 4 of the rear support part 3B is cancelled to discharge the intraocular lens 1 completely from the intraocular lens insertion device 10. When the inclined surface 353 of the plunger 300 abuts against the front inclined part 114 of the main body 100, the advance of the plunger 300 stops. The extrusion member 310 pops out of the distal end of the nozzle part 182 in a state where the inclined surface 353 of the plunger 300 abuts against the front inclined part 114 of the main body 100.

The user (operator) brings the extrusion member 310 that has popped out of the bevel part 183 into abutment with the intraocular lens 1 discharged into the capsule to adjust the position of the intraocular lens 1. When the position adjustment of the intraocular lens 1 in the capsule is finished, the user retrieves the intraocular lens insertion device 10 form the incision of the patient's eye. With the above processes, the ejection of the intraocular lens 1 is complete.

<3-1. Operation and Effect: 1>

In the intraocular lens insertion device 10 of the embodiment, the off-axis movement part 177 presses the support part 3 of the intraocular lens 1 from a direction different from the extrusion axis A. Consequently, the support part 3 can be suitably bent toward the direction of the optical part 2. For example, while a twist of the support part 3 can be reduced, the bending of the support part 3 in an unintended shape can be reduced. Therefore, the intraocular lens 1 can be bent in a suitable shape and ejected into the eye.

Moreover, in the intraocular lens insertion device 10 of the embodiment, the off-axis movement part 177 that presses the support part 3 from a direction different from the extrusion axis A is assembled with the extrusion member 310 that presses the support part 3 by moving linearly in a direction parallel to the extrusion axis A (along the extrusion axis A). The off-axis movement part 177 and the extrusion member 310 press the support part 3. The support part 3 can be pressed from a plurality of directions. Accordingly, the support part 3 can be bent in a suitable shape.

Moreover, in the intraocular lens insertion device 10 of the embodiment, the off-axis movement part 177 abuts against the portion closer to the distal end side than the first constricted portion 7, for bending at a predetermined position toward the direction of the optical part 2, of the support part 3, and accordingly the support part 3 is pressed. As a result, the support part 3 becomes easier to bend at the first constricted portion 7. Accordingly, the support part 3 can be bent in a suitable shape.

Moreover, in the intraocular lens insertion device 10 of the embodiment, the off-axis movement part 177 abuts against the portion of the support part 3, the portion being closer to the proximal end side (the root portion 4 side of the support part 3) than the middle of the total length, and accordingly the support part 3 is pressed. Therefore, the entire support part 3 becomes easier to bend so that the support part 3 can be bent in a suitable shape.

Moreover, the off-axis movement part 177 of the embodiment comprises an elastic member. Furthermore, the stress generation part 156 comes into contact with the off-axis movement part 177. The stress generation part 156 is a member different from the off-axis movement part 177, and provides stress to the off-axis movement part 177 to press the support part 3. The stress generation part 156 comes into contact with the off-axis movement part 177 to deform the off-axis movement part 177. Accordingly, the support part 3 can be pressed. Therefore, the intraocular lens insertion device 10 of the embodiment can press the support part 3 from a direction different from the extrusion axis A with a simple mechanism.

Moreover, in the embodiment, the stress that moves, onto the extrusion axis A, the intraocular lens 1 held off the extrusion axis A is used to provide the stress from the stress generation part 156 to the off-axis movement part 177. As a result, the off-axis movement part 177 presses the support part 3. In other words, the support part 3 can be pressed from a direction different from the extrusion axis A, using the stress that moves the intraocular lens 1 to the extrusion axis A. In other words, the movement of the entire intraocular lens 1 and the bending of the support part 3 toward the direction of the optical part 2 can be performed in one operation. As a result, the intraocular lens 1 can be ejected simply and quickly.

Moreover, in the embodiment, the off-axis movement part 177 is connected to the member (the setting part 170)

forming the installation part 130. In other words, the off-axis movement part 177 is connected to the installation part 130. Therefore, the support part 3 can be accurately pressed by the off-axis movement part 177 without a complicated or precise mechanism.

Moreover, in the embodiment, at least part of the point, which comes into contact with the support part 3, of the off-axis movement part 177 has a curved surface. Therefore, the support part 3 to be deformed can be suitably pressed by the off-axis movement part 177.

Moreover, in the intraocular lens insertion device 10 of the embodiment, the distal end of the off-axis movement part 177 is rotated in the direction approaching the extrusion axis A. Therefore, the off-axis movement part 177 can change the direction to press the support part 3 while pressing the support part 3. For example, the off-axis movement part 177 can bend the support part 3 toward the direction of the optical part 2 while moving along the side surface of the support part 3.

Moreover, in the intraocular lens insertion device 10 of the embodiment, the off-axis movement part 177 can press the support part 3, using the stress applied in a direction different from the direction in which the off-axis movement part 177 presses the support part 3. Therefore, with the configuration for pressing the support part 3 from the direction different from the extrusion axis A, it is possible to avoid upsizing of the intraocular lens insertion device 10.

Moreover, in the embodiment, the width of the distal end of the off-axis movement part 177 is larger than that of the support part 3 in the direction perpendicular to the optical part 2. Therefore, even if the support part 3 deforms, the off-axis movement part 177 can press the support part 3 suitably. For example, even if the support part 3 swings up and down during the deformation, the distal end of the off-axis movement part 177 can press the support part 3 suitably.

<3-2. Operation and Effect: 2>

The intraocular lens insertion device 10 of the embodiment includes the deformation suppression part (the sideward deformation suppression part 149 and the upward deformation suppression part 159 in the embodiment). The deformation suppression part (deformation control part) suppresses deformation of at least part of the support part 3 that is moved by the movement part 301 in the direction approaching the optical part 2. The deformation suppression part is included and accordingly the support part 3 can be bent in a suitable shape. For example, it is possible to prevent a failure that part of the support part 3 deforms excessively and cannot be bent fully toward the direction of the optical part 2.

Moreover, in the intraocular lens insertion device 10 of the embodiment, the sideward deformation suppression part 149 suppresses deformation of the support part 3 pressed by the linear movement part 313 in the direction away from the extrusion axis A. Therefore, it is possible to prevent a failure that the support part 3 deforms in the direction away from the extrusion axis A.

Moreover, in the intraocular lens insertion device 10 of the embodiment, the sideward deformation suppression part 149 suppresses deformation of the support part 3 pressed by the linear movement part 313 in the direction away from the linear movement part 313. Therefore, it is possible to prevent a failure that the support part 3 deforms in the direction away from the linear movement part 313.

Moreover, in the intraocular lens insertion device 10 of the embodiment, the sideward deformation suppression part 149 is brought into contact with the first constricted portion 7 for bending the support part 3 at the predetermined position to restrict the deformation direction of the support part 3 at the first constricted portion 7. In other words, the sideward deformation suppression part 149 being part of the deformation suppression part comes into contact with the first constricted portion 7 to restrict the deformation direction of the support part 3 at the first constricted portion 7. Therefore, it is possible to prevent a failure that the support part 3 deforms excessively at the first constricted portion 7.

Moreover, in the intraocular lens insertion device 10 of the embodiment, the upward deformation suppression part 159 is brought into contact with the proximal end of the support part 3 to restrict the deformation direction of the proximal end of the support part 3. Therefore, for example, it is possible to prevent a failure that the optical part 2 rises due to deformation of the root portion 4 of the support part 3. For example, the plunger 300 can press the optical part 2 suitably.

Moreover, the intraocular lens insertion device 10 of the embodiment includes the sideward deformation suppression part 149 at the position facing the side surface side of the intraocular lens 1. Therefore, sideward deformation of the intraocular lens 1 can be suppressed.

Moreover, the intraocular lens insertion device 10 of the embodiment includes upward deformation suppression part 159 at the position facing at least one of the front surface side and the rear surface side of the intraocular lens 1. Therefore, it is possible to prevent a failure that the support part 3 does not bend suitably. For example, it is possible to prevent a failure that the optical part 2 rises due to deformation of the proximal end portion of the support part 3. For example, the plunger 300 can press the optical part 2 suitably.

Moreover, in the intraocular lens insertion device 10 of the embodiment, the upward deformation suppression part 159 is formed on the optical surface side of the optical part 2 that mounts at least part of the support part 3 thereon. Therefore, the support part 3 can be suitably bent above the optical part 2.

<3-3. Operation and Effect: 3>

In the embodiment, the injection port 154 is located outward of the outer surface of the loop-shaped support part 3 when the intraocular lens 1 is installed in the installation part 130. Therefore, even if the viscoelastic substance is injected, the support part 3 can be suitably bent. For example, the support part 3 can be bent toward the direction approaching the optical part 2 due to the stress generated upon the injection of the viscoelastic substance.

Moreover, in the embodiment, the injection port 154 is located in the predetermined range sandwiched between the straight line passing both the center of the optical part 2 and the proximal end of the support part 3 and the straight line extending parallel to the extrusion axis A from the center of the optical part 2 when the intraocular lens 1 is installed in the installation part 130. Therefore, even if the viscoelastic substance is injected, the support part 3 can be suitably bent.

Moreover, in the embodiment, the injection port 154 is located closer to the distal end side than the optical part 2 installed in the installation part 130. Therefore, the front support part 3A can be suitably bent. Moreover, the viscoelastic substance can be suitably filled in the insertion part 180 and the installation part 130 without injecting a large amount of the viscoelastic substance.

Moreover, the intraocular lens insertion device 10 of the embodiment includes the injection port 154 in the area of the passage part 132 from the distal end of the area (the optical part installation part 131) where the optical part 2 is installed in the installation part 130, up to the proximal end of the insertion part 180. Therefore, the viscoelastic substance can be suitably filled in the insertion part 180 and the installation part 130 without injecting a large amount of the viscoelastic substance.

Moreover, in the embodiment, the intraocular lens 1 is installed in the installation part 130 in a state where at least one of the support parts 3 is pointed toward the distal end direction of the extrusion axis A. Therefore, even if the breadth of the installation part 130 is narrow, the viscoelastic substance can be suitably injected.

Moreover, the intraocular lens insertion device 10 of the embodiment includes the needle guide part 153. The needle guide part 153 is formed on the wall portion of the main body 100 in such a manner as to surround the injection port 154. The needle guide part 153 guides the movement of a needle for injecting the viscoelastic substance. Therefore, even if the needle abuts against the wall portion, the user can move the needle easily to the injection port 154.

Moreover, in the embodiment, the width of the area surrounded by the needle guide part 153 is formed in such a manner as to become increasingly narrower toward the injection port 154. Therefore, the user can move the needle in abutment with the wall easily to the injection port 154.

Moreover, in the embodiment, the needle guide part 153 extends in such a manner as to intersect with the straight lines linking the movement regulating holes 152 to the injection port 154. Therefore, it is possible to prevent the needle from being wrongly inserted into the movement regulating hole 152.

Moreover, in the embodiment, the injection port 154 is provided in the inner wall (in other words, the upper wall portion) of the passage part 132 on the side facing the front surface side of the optical part 2. Therefore, the viscoelastic substance is prevented from entering below the optical part 2 too much. Hence, a possibility that the position of the intraocular lens 1 in the up-down direction is displaced can be reduced.

<3-4. Operation and Effect: 4>

In the embodiment, the passage having a width larger than the width of the optical part 2 is formed in the passage part 132. The distorted part 174 is included in the passage wall of the passage part 132, the passage wall facing the optical surface 2B being one side of the optical part 2. The distorted part 174 distorts in a concave shape toward the direction away from the extrusion axis A as viewed from the direction of the extrusion axis A. The amount of distortion of the distorted part 174 increases progressively from the proximal end side toward the distal end side.

The distorted part 174 prevents sudden application of stress to the intraocular lens 1 due to the shape of the inner wall of the insertion part 180 upon the movement of the intraocular lens 1 from the passage part 132 to the insertion part 180. Hence, the intraocular lens 1 can be suitably bent. Moreover, the intraocular lens 1 deforms along the distorted shape due to the surface tension generated by the viscoelastic substance filled in the main body 100. In other words, it becomes difficult to create a gap between the upper surface of the distorted part 174 and the optical part 2. Therefore, the entry of the distal end of the front support part 3A between the optical part 2 and the inner wall can be reduced so that the intraocular lens 1 can be suitably bent.

Moreover, in the embodiment, the proximal end portion of a bottom wall of the passage part 132 is formed flat as viewed from the direction of the extrusion axis A. Therefore, as the optical part 2 proceeds toward the distal end in the intraocular lens insertion device 10, it can be gradually deformed. As a result, deformation failure of the intraocular lens 1 can be prevented. For example, the flat passage wall and stronger surface tension of the viscoelastic substance are used to enable the optical part 2 before deformation can be stuck on the passage wall.

Moreover, in the intraocular lens insertion device 10 of the embodiment, the optical part 2 is installed in the installation part 130 in a state where the support part 3 is placed in the passage part 132. The support part 3 is placed in the passage part 132 having the distorted part 174. Accordingly, while a suitable bend in the optical part 2 due to the distorted shape is maintained, the total length of the intraocular lens insertion device 10 can be reduced.

Moreover, the intraocular lens insertion device 10 of the embodiment includes the injection port 154 at the passage part 132. Therefore, the effect of the surface tension of the viscoelastic substance injected from the injection port 154 can be suitably utilized.

Moreover, in the embodiment, the proximal end of the tapered part 181 is smoothly connected to the passage part 132. Therefore, it is possible to reduce the occurrence of unintended behavior in the intraocular lens 1 due to the projections and depressions of the inner wall upon the movement of the intraocular lens 1 pressed by the plunger 300 from the passage part 132 to the tapered part 181. For example, it is possible to prevent the failure that the optical part 2 rises due to the projections and depressions of the inner wall, a gap is created below the optical part 2, and the front support part 3A ends up entering the gap.

<3-5. Operation and Effect: 5>

In the embodiment, the end portion on the distal end side of the linear movement part 313 is placed offset to the direction where the proximal end of the support part 3 of the intraocular lens 1 installed in the installation part 130 is located, as viewed from the distal end side of the extrusion axis A. Therefore, in the intraocular lens insertion device 10, the portion, which is closer to the proximal end side than the extrusion axis A, of the support part 3 can be pressed. Hence, the support part 3 can be suitably bent toward the direction approaching the optical part 2.

Moreover, the intraocular lens insertion device 10 of the embodiment includes, in the extrusion member 310, both the linear movement part 313 that moves linearly in the direction parallel to the extrusion axis A (along the extrusion axis A), and the optical part contact part 314 that extrudes the optical part 2 in contact with the optical part 2. Therefore, the support part 3 and the optical part 2 can be pressed with a simple structure. Moreover, the intraocular lens insertion device 10 can be provided at a moderate price without increasing its size.

Moreover, in the embodiment, the cross-sectional area of the distal end part 312 of the extrusion member 310 in the direction perpendicular to the extrusion axis A is set to a cross-sectional area that allows passage through the nozzle part 182. Since the extrusion member 310 can pass through the nozzle part 182, the support part 3 can be suitably bent without making the structure of the intraocular lens insertion device 10 complicated.

Moreover, in the embodiment, the linear movement part 313 is placed closer to the distal end side than the optical part contact part 314. Therefore, the intraocular lens insertion device 10 can press in the support part 3 up to the position closer to the distal end side than the end portion on the proximal end side of the outer surface of the optical part 2. Hence, the distal end of the support part 3 can be suitably bent.

Moreover, in the embodiment, the end portion on the distal end side of the linear movement part 313 that is offset to the proximal end direction of the support part 3 has a curved surface. Therefore, during the time when the linear movement part 313 is pressing the support part 3 in the intraocular lens insertion device 10, the support part 3 can be bent while being slid to the end portion on the distal end side of the linear movement part 313.

Moreover, the linear movement part 313 of the embodiment includes the slope inclined toward the direction away from the extrusion axis A (leftward or rightward) with respect to the plane orthogonal to the extrusion axis A. The slope is formed extending from the end portion on the distal end side of the linear movement part 313 to the opposite direction to the direction where the proximal end of the support part 3 is located, as viewed from the extrusion axis A.

Moreover, the intraocular lens insertion device 10 of the embodiment includes the left depressed part 319. The left depressed part 319 is connected to the proximal end of the linear movement part 313, and depressed in the proximal end direction of the extrusion axis A. The left depressed part 319 is included and accordingly, an ejection can be made while the support part 3 is sandwiched between the plunger 300 and the inner wall of the main body 100. The intraocular lens 1 can be restored in a fixed direction. Accordingly, the intraocular lens 1 can be suitably ejected.

<3-6. Operation and Effect: 6>

The intraocular lens insertion device 10 of the embodiment includes the abutment parts 157A and 157B. The abutment parts 157A and 157B are provided at at least the right and left positions apart from the extrusion axis A. The abutment parts 157A and 157B abut against the different points on the side surface of the optical part 2 passing over the passage. The stresses given to the intraocular lens 1 by the two abutment parts 157A and 157B from the right and left directions are different between the right and left sides of the intraocular lens 1. Therefore, the two abutment parts 157A and 157B can prevent, for example, the intraocular lens 1 that is being extruded from rotating largely with the restoring force of the rear support part 3B.

The stress given to the intraocular lens 1 is made different between the right side and the left side. Accordingly, when the intraocular lens 1 whose support part 3 has been bent is pressed, unintended deformation of the intraocular lens 1 is suppressed. For example, it is possible to reduce a phenomenon that the intraocular lens 1 moves over to an inner wall on one side when the intraocular lens 1 is moved in the distal end direction of the extrusion axis A. Therefore, it is possible to prevent a failure that, in the installation part 130, the intraocular lens 1 is sandwiched between the plunger 300 and the inner wall. Moreover, for example, the intraocular lens 1 is brought into abutment with the abutment parts 157A and 157B that respectively give different stresses. Accordingly, the intraocular lens 1 in abutment with the abutment parts 157A and 157B can be guided in a direction that reduces the stresses. Therefore, the travelling direction of the intraocular lens 1 can be locally changed to the opposite direction to the direction to which the intraocular lens 1 whose support part 3 has been bent tends to move over (in the embodiment, the direction of the inner wall on the side where the root portion 4 of the rear support part 3B is placed). As a result, it is possible to prevent a failure that, in the installation part 130, the intraocular lens 1 is sandwiched between the plunger 300 and the inner wall.

Moreover, in the embodiment, at least any of the shape, size, and distance from the extrusion axis A is different between the right abutment part 157A and the left abutment part 157B. Therefore, the right stress and the left stress can be generated in such a manner as to be different from each other. Different stresses from the right and left may be given to the intraocular lens 1 by changing, between the abutment parts 157A and 157B, the surface roughness or surface coating of the surfaces of the abutment parts 157A and 157B, the surfaces abutting against the intraocular lens 1.

Moreover, the abutment parts 157A and 157B of the embodiment each include the slope whose distance to the extrusion axis A is progressively reduced toward the distal end. Therefore, the intraocular lens insertion device 10 can extrude the intraocular lens 1 while sliding the intraocular lens 1 on the slopes. Hence, the intraocular lens 1 can be extruded in the distal end direction with a small extrusion force. Moreover, the structures of the abutment parts 157A and 157B can be made simple.

Moreover, in the embodiment, the slope is placed on each of the right and left sides of the extrusion axis A. These slopes are on the same plane orthogonal to the extrusion axis A. Therefore, both the stop of the intraocular lens 1 and the advance of the intraocular lens 1 can be performed without providing a complicated structure.

Moreover, in the embodiment, the distance from the extrusion axis A to the slope is different between the right slope and the left slope. Therefore, different stresses from the right and left can be generated.

Moreover, in the intraocular lens insertion device 10 of the embodiment, the stress from the side where the proximal end of the bent support part 3 is located is larger than the stress from the other side. Therefore, it is possible to prevent the occurrence of unintended deformation of the intraocular lens 1 when the intraocular lens 1 whose support part 3 has been bent is being extruded.

Moreover, in the embodiment, the abutment parts 157A and 157B have an asymmetric shape with respect to the extrusion axis A. Hence, the rotation of the intraocular lens 1 can be prevented during extrusion without providing a complicated structure.

<3-7. Operation and Effect: 7>

The intraocular lens insertion device 10 of the embodiment includes the deformation guide part 146. The deformation guide part 146 bends, in a predetermined shape, the support part 3 to be deformed and moved by the movement part 301. Therefore, the intraocular lens insertion device 10 can suppress variations in deformed shapes when bending the support part 3, or when extruding the intraocular lens 1 whose support part 3 has been bent. Therefore, the support part 3 can be bent in a suitable shape.

Moreover, the deformation guide part 146 of the embodiment is formed depressing or protruding the inner wall of the main body 100. Therefore, the deformation guide part 146 can be provided without providing a complicated mechanism. For example, the deformation guide part 146 can be easily manufactured by resin molding.

The intraocular lens insertion device 10 of the embodiment includes the deformation guide part 146 on the inner wall of the main body 100 on the side facing the optical surface 2A. Therefore, the support part 3 can be suitably bent toward the position facing the optical surface 2A (above the optical surface 2A in the embodiment).

Moreover, the deformation guide part 146 of the embodiment is formed extending in the distal end direction of the extrusion axis A. Therefore, the intraocular lens insertion device 10 can bend, in a suitable shape, the support part 3 that moves in the distal end direction of the extrusion axis A.

Moreover, the deformation guide part 146 of the embodiment includes the inclined guide surface 146B inclined facing the proximal end direction of the extrusion axis A. Therefore, the deformation guide part 146 can easily bend, in a suitable shape, the support part 3 that moves in the distal end direction of the extrusion axis A.

Moreover, the deformation guide part 146 of the embodiment includes the parallel guide surfaces 146A extending parallel to the extrusion axis A. Therefore, the deformation guide part 146 can bend the support part 3 in a suitable shape by abutting against the support part 3 that moves in the distal end direction of the extrusion axis A.

Moreover, in the embodiment, the inclined guide surface 146B is coupled to the parallel guide surface 146A. Therefore, the deformation guide part 146 can bend the support part 3 in a suitable shape and correct the deformed shape, in accordance with the advanced position of the intraocular lens 1.

<3-8. Operation and Effect: 8>

The intraocular lens insertion device 10 of the embodiment includes the deformed part (in the embodiment, the first contact parts 175A and 175B), and the movement part 301. The deformed part is movable in the direction intersecting with the central plane P of the intraocular lens 1 to position at least any of one or a plurality of support parts 3 extending from the optical part 2 at the standby position in a state of being displaced from the central plane P. The movement part 301 moves the support part 3 positioned by the deformed part at the standby position, in the direction approaching the optical part 2.

In other words, the deformed part of the embodiment is movable in the direction intersecting with the mounting surface (in the embodiment, the upper surfaces of the second contact parts 176A and 176B) to position at least any of the support parts 3 extending from the optical part 2 at its standby position different in height from the mounting surface.

In the intraocular lens insertion device 10 of the embodiment, the deformed part and the movement part 301 can easily bend the support part 3 extending outward from the periphery of the optical part 2. Moreover, the support part 3 can be easily displaced from the central plane P and positioned at the standby position.

Moreover, the intraocular lens insertion device 10 of the embodiment includes the first contact parts 175A and 175B. The first contact parts 175A and 175B move the support part 3 while in contact with at least part of the support part 3 to move the support part 3 to the standby position. Therefore, the support part 3 can be stably located at the standby position.

Moreover, the intraocular lens insertion device 10 of the embodiment includes the second contact parts 176A and 176B. The second contact parts 176A and 176B move the optical part 2 while in contact with at least part of the optical part 2 to position the optical part 2. Therefore, the optical part 2 can be stably positioned.

Moreover, the second contact part 176 of the embodiment moves the optical part 2 on the extrusion axis A. The deformation of the support part 3 coordinates with the movement of the optical part 2. Accordingly, the optical part 2 of the intraocular lens 1 having the displaced support part 3 can be easily placed on the extrusion axis A.

Moreover, the intraocular lens insertion device 10 of the embodiment includes the holding part 160 that holds the optical part 2 at a position away from the extrusion axis A. Moreover, the second contact part 176 moves the optical part 2 held by the holding part 160 while in contact to move the optical part 2 onto the extrusion axis A. Therefore, the intraocular lens insertion device 10 can position the support part 3 at an appropriate position (in other words, a position displaced from the central plane P) while moving the optical part 2 onto the extrusion axis A.

Moreover, the intraocular lens insertion device 10 of the embodiment includes the base part 171 that holds both the first contact part 175 and the second contact part 176. Therefore, the user can move the intraocular lens 1 by simply making the base part 171 movable.

Moreover, in the embodiment, the portion, which comes into contact with the support part 3, of the first contact part 175, and the portion, which comes into contact with the optical part 2, of the second contact part 176 are displaced in the direction intersecting with the central plane P. Therefore, when the support part 3 is placed at the standby position, the optical part 2 is placed at the displaced position.

Moreover, the base part 171 of the embodiment rotates about the rotation axis to move in the direction intersecting with the central plane P. Therefore, the user can displace the support part 3 with respect to the optical part 2 by simply rotating the base part 171. The manufacturer can provide the intraocular lens insertion device 10 at a moderate price.

<3-9. Operation and Effect: 9>

The intraocular lens insertion device 10 of the embodiment includes the positioning parts 185 and the movement guide parts 186. The positioning parts 185 position the support part 3 at a position displaced from the central plane P. The movement guide parts 186 guide the movement of the support part 3 by the movement part 301. Specifically, the movement guide parts 186 guide the movement of the support part 3 while maintaining the distance between the support part 3 and the central plane P constant. Alternatively, the movement guide parts 186 guide the movement of the support part 3 in such a manner as that the support part 3 approaches the central plane P as the support part 3 approaches the installation part 130. Therefore, it is possible to prevent a failure that the support part 3 deforms in an unintended shape in the middle of moving closer to the optical part 2.

Moreover, the movement part 301 of the embodiment includes the linear movement part 313. The linear movement part 313 moves along a straight line (for example, the extrusion axis A) to press the support part 3 and accordingly moves the support part 3. In other words, the linear movement part 313 moves linearly along the extrusion axis A to move the support part 3 in the direction approaching the optical part 2. Therefore, the intraocular lens insertion device 10 can bend the support part 3 with a simple mechanism.

Moreover, the extrusion member 310 of the intraocular lens insertion device 10 of the embodiment includes the linear movement part 313 and the optical part contact part 314. Therefore, the user can perform both tacking and press-in of the optical part 2 by simply pressing in the extrusion member 310.

Moreover, in the embodiment, the contact portion, which comes into contact with the support part 3, of the movement guide part 186 is formed in a surface or ridge. Therefore, the movement guide part 186 can guide the movement of the support part 3 smoothly.

Moreover, the movement guide part 186 of the embodiment includes the first guide part 178A that comes into contact with part of the support part 3, and the second guide part 178B. The second guide part 178B comes into contact with the portion of the support part 3, the portion being closer to the proximal end side than the portion that comes into contact with the first guide part 178A. Therefore, the movement guide part 186 can guide the movement of the support part 3 at a plurality of points. The shape of the support part 3 displaced from the central plane P is stabilized.

Moreover, in the embodiment, one of the first guide part 178A and the second guide part 178B is located on the right side of the extrusion axis A and the other is located on the left side of the extrusion axis A in the right-left direction perpendicular to the extrusion axis A and parallel to the central plane P. Therefore, the movement guide part 186 can come into contact with the support part 3 at the positions on the right and left sides of the extrusion axis A. Thus, tacking is stabilized.

Moreover, in the embodiment, the distance between the first guide part 178A and the central plane P is longer than the distance between the second guide part 178B and the central plane P. Therefore, the support part 3 can be positioned at the position displaced from the optical part 2 while being appropriately inclined.

<4. Others>

In the embodiment, one example of the technology of the present disclosure has been described using the preset-type intraocular lens insertion device 10 into which the intraocular lens 1 is preloaded upon manufacture. However, the technology illustrated by example in the embodiment is not applied only to the preset-type intraocular lens insertion device 10. The intraocular lens insertion device 10 of the embodiment may be, for example, the non-preset type intraocular lens insertion device 10 into which the intraocular lens 1 is loaded on a site of use.

Moreover, a cartridge including the distal end of the insertion part 180 to the proximal end of the installation part 130 may be formed. The cartridge may be combined with extrusion means for pressing the intraocular lens 1 to manufacture the intraocular lens insertion device 10. In this case, the extrusion member 310 illustrated by example in the embodiment may be used as the extrusion means. Moreover, the extrusion member 310 illustrated by example in the embodiment may be attached to the cartridge. The extrusion member 310 of the cartridge may be pressed by the extrusion means.

The expression that "the linear movement part 313 that moves linearly in a direction parallel to the extrusion axis A" does not simply indicate that the linear movement part 313 moves strictly linearly in all the sections. For example, the plunger 300 may move in the direction away from the extrusion axis A in a predetermined section when heading to the distal end of the insertion part 180. Moreover, the distal end of the plunger 300 may advance along the curved surface (for example, through an arc).

The above-mentioned embodiment is an exemplification in all aspects. It should not be considered that all the configurations of the above-mentioned embodiment need to be applied (used). In other words, only part of the configurations of the above-mentioned embodiment may be applied (in other words, only part of a plurality of technical features included in the above-mentioned embodiment may be carried out). For example, only the deformation guide part 146 may be applied.

Moreover, it should be considered that the above-mentioned embodiment is an exemplification in all the aspects and is not restrictive. The technical scope of the present disclosure is indicated not by the above-mentioned description but by the claims. The technical scope of the present disclosure is intended to include the claims, and meanings equivalent to the claims, and all amendments within the scope.

The dotted lines of FIGS. 4, 5, and 6B indicates the contour of the intraocular lens 1, and it can also be said that the position of the intraocular lens 1 in a state where an extrusion by the plunger 300 becomes possible is illustrated as the insertion state of the intraocular lens insertion device 10.

The intraocular lens storage part 163 and the holding protruding part 166 may be formed on the substantially plate-shaped base. A through hole may be formed in the base, the through hole penetrating the base in such a manner as that the first contact parts 175A and 175B and the second contact parts 176A and 176B (see FIG. 7) of the setting part 170 can be moved in the up-down direction.

The linear movement part 313 has a protruding shape that protrudes toward the distal end direction, and may be formed in a curved shape being convex in the distal end direction.

In the embodiment, the intraocular lens insertion device 10 may be accommodated in the casing by locating the plunger 300 at the initial position where the rear engagement part 113 of the main body 100 is engaged with the front blade part 351 of the plunger 300. At the initial position, the distal end of the plunger 300 may be located slightly closer to the distal end side than the proximal end of the installation part 130.

The stress generation part 156 of the embodiment may provide stress to the off-axis movement part 177 using the stress that moves the intraocular lens 1 held by the holding part 160 onto the extrusion axis A.

The left depressed part 319 may be connected to the proximal end of the support part 3 of the linear movement part 313, and depressed in the proximal end direction of the extrusion axis A.

The embodiment may be the following first to eighth intraocular lens insertion devices and first intraocular lens insertion system.

The first intraocular lens insertion device is an intraocular lens insertion device that advances a rod-like extrusion member along an extrusion axis to insert, into the eye, a deformable intraocular lens having an optical part and one or a plurality of support parts extending outward from the periphery of the optical part, and includes an installation part where the intraocular lens is installed in a state where at least one support part is placed closer to a proximal end side than the optical part, and an off-axis movement part that is a member different from the extrusion member and that presses the support part of the intraocular lens installed in the installation part from a direction different from the extrusion axis to deform and move the support part.

In the second intraocular lens insertion device according to the first intraocular lens insertion device, the extrusion member has a linear movement part that moves linearly in a direction parallel to the extrusion axis to move the support part in a direction approaching the optical part.

In the third intraocular lens insertion device according to the first or second intraocular lens insertion device, the support part has a constricted portion for bending the support part at a predetermined position toward the direction of the optical part, and the off-axis movement part abuts against a portion of the support part, the portion being closer to a distal end side than the constricted portion, and presses the support part.

In the fourth intraocular lens insertion device according to any of the first to third intraocular lens insertion devices, the off-axis movement part is brought into abutment with a portion closer to the proximal end side than the middle of the total length of the support part, and presses the support part.

The fifth intraocular lens insertion device according to any of the first to fourth intraocular lens insertion devices further includes a stress generation part that is formed of a member different from the off-axis movement part, and provides stress for allowing the off-axis movement part to press the support part, wherein the off-axis movement part is made of an elastic material, and the stress generation part comes into contact with the off-axis movement part to deform the off-axis movement part and press the support part.

In the sixth intraocular lens insertion device according to the fifth intraocular lens insertion device, the stress generation part uses the stress that moves, onto the extrusion axis, the intraocular lens held off the extrusion axis to provide the stress to the off-axis movement part, and accordingly presses the support part.

In the seventh intraocular lens insertion device according to the fifth or sixth intraocular lens insertion device, the off-axis movement part is connected to a member forming the installation part.

In the eighth intraocular lens insertion device according to any of the first to seventh intraocular lens insertion devices, at least part of a portion, which comes into contact with the support part, of the off-axis movement part is formed in a curved surface.

The first intraocular lens insertion system is an intraocular lens insertion system that advances a rod-like extrusion member along an extrusion axis to insert, into the eye, a preloaded deformable intraocular lens having an optical part and one or a plurality of support parts extending outward from the periphery of the optical part, and includes an installation part where the intraocular lens is installed in a state where at least one support part is placed closer to a proximal end side than the optical part, and an off-axis movement part that is a member different from the extrusion member, presses the support part of the intraocular lens installed in the installation part from a direction different from the extrusion axis to deform and move the support part.

These intraocular lens insertion devices and intraocular lens insertion system can eject the intraocular lens easily.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An intraocular lens insertion device comprising:
   a deformable intraocular lens including an optical part and one or a plurality of support parts extending outward from a periphery of the optical part, the support parts comprising a distal end and a proximal end, the distal end being a free end;
   a plunger that extrudes the deformable intraocular lens into an eye along an extrusion axis;
   an installation part in which the intraocular lens is installed in a state where at least one support part is placed closer to a proximal end side of the extrusion axis than the optical part; and
   an off-axis movement part that presses a portion adjacent to the proximal end of the support part of the intraocular lens installed in the installation part from a direction different from the extrusion axis, the off-axis movement part deforming and moving only the support part in a direction approaching the optical part,
   wherein the plunger pushes the support part which is deformed by the off-axis movement part.

2. The intraocular lens insertion device according to claim 1, wherein the plunger includes a linear movement part that moves linearly along the extrusion axis to move the support part in a direction approaching the optical part.

3. The intraocular lens insertion device according to claim 1, wherein
   the support part includes a constricted portion for bending the support part at a predetermined position toward a direction of the optical part, and
   the off-axis movement part abuts against a portion of the support part, which is closer to a distal end side than the constricted portion, to press the support part.

4. The intraocular lens insertion device according to claim 1, wherein the off-axis movement part is configured to abut against a portion of the support part, which is closer to a proximal end side than a middle of a total length of the support part, to press the support part.

5. The intraocular lens insertion device according to claim 1, further comprising a stress generation part that provides the off-axis movement part with stress for allowing the off-axis movement part to press the support part, wherein
   the off-axis movement part is made of an elastic material, and
   the off-axis movement part is deformed by contact of the stress generation part with the off-axis movement part to press the support part.

6. The intraocular lens insertion device according to claim 5, wherein
   the stress generation part comes into contact with the off-axis movement part using stress for moving, onto the extrusion axis, the intraocular lens held off the extrusion axis, and provides the stress to the off-axis movement part, and
   the off-axis movement part is deformed by the provided stress and presses the support part.

7. The intraocular lens insertion device according to claim 5, wherein the off-axis movement part is connected to the installation part.

8. The intraocular lens insertion device according to claim 1, wherein at least part of a portion, which is configured to contact with the support part, of the off-axis movement part is a curved surface.

9. An intraocular lens insertion system comprising:
   deformable means for refracting a light beam including an optical part and one or a plurality of support parts extending outward from a periphery of the optical part, the support parts comprising a distal end and a proximal end, the distal end being a free end;
   means for extruding the deformable means for refracting into an eye along an extrusion axis;
   means for installing the deformable means for refracting in a state where at least one support part is placed closer to a proximal end side of the extrusion axis than the optical part; and
   means for pressing the support part of the installed deformable means for refracting from a direction different from the extrusion axis to deform and rotate the support part, a rotational axis of the support part being parallel to an optical axis of the optical part.

10. An intraocular lens insertion device comprising:
means for extruding a deformable intraocular lens into an eye along an extrusion axis, the deformable intraocular lens including an optical part and one or a plurality of support parts extending outward from a periphery of the optical part;
means for installing the intraocular lens in a state where at least one support part is placed closer to a proximal end side of the extrusion axis than the optical part; and
means for pressing the support part of the installed intraocular lens from a direction different from the extrusion axis to deform and move the support part,
wherein the means for extruding comprises a distal end part, in a direction of the extrusion axis, having a linear movement part at an upper side of the distal end part and an optical part contact part at a lower side of the distal end part, a distal end, in the direction of the extrusion axis, of the linear movement part being misaligned in the direction of the extrusion axis with a distal end, in the direction of the extrusion axis, of the optical part contact part.

11. The intraocular lens insertion device according to claim 10, wherein the linear movement part is configured to move, by linearly moving along the extrusion axis, the support part in a direction approaching the optical part.

12. The intraocular lens insertion device according to claim 10, wherein
the support part includes a constricted portion for bending the support part at a predetermined position toward a direction of the optical part, and
the means for pressing abuts against a portion of the support part, which is closer to a distal end side than the constricted portion, to press the support part.

13. The intraocular lens insertion device according to claim 10, wherein the means for pressing is configured to abut against a portion of the support part, which is closer to a proximal end side than a middle of a total length of the support part, to press the support part.

14. The intraocular lens insertion device according to claim 10, further comprising means for providing the means for pressing with stress for allowing the means for pressing to press the support part, wherein
the means for pressing is made of an elastic material, and
the means for pressing is deformed by contact of the means for providing with the means for pressing to press the support part.

15. The intraocular lens insertion device according to claim 14, wherein
the means for providing comes into contact with the means for pressing by using stress for moving, onto the extrusion axis, the intraocular lens held off the extrusion axis, and provides the stress to the means for pressing, and
the means for pressing is deformed by the provided stress and presses the support part.

16. The intraocular lens insertion device according to claim 14, wherein the means for pressing is connected to the means for installing.

17. The intraocular lens insertion device according to claim 10, wherein at least part of a portion, which is configured to contact with the support part, of the means for pressing is a curved surface.

* * * * *